(12) United States Patent
Turner et al.

(10) Patent No.: US 8,822,639 B2
(45) Date of Patent: Sep. 2, 2014

(54) TRANSFERRIN FUSION PROTEIN LIBRARIES

(75) Inventors: Andrew John Turner, Durham, NC (US); Baiyang Wang, Washington Crossing, PA (US)

(73) Assignee: Biorexis Pharmaceutical Corporation, New York, NY (US)

( * ) Notice: Subject to any disclaimer, the term of this patent is extended or adjusted under 35 U.S.C. 154(b) by 1223 days.

(21) Appl. No.: 12/517,855

(22) PCT Filed: Dec. 7, 2007

(86) PCT No.: PCT/IB2007/003908
§ 371 (c)(1),
(2), (4) Date: Dec. 16, 2010

(87) PCT Pub. No.: WO2008/072075
PCT Pub. Date: Jun. 19, 2008

(65) Prior Publication Data
US 2011/0086768 A1 Apr. 14, 2011

Related U.S. Application Data

(60) Provisional application No. 60/934,951, filed on Dec. 12, 2006.

(51) Int. Cl.
C07K 2/00 (2006.01)
C07K 19/00 (2006.01)
A61K 38/00 (2006.01)

(52) U.S. Cl.
USPC .......................................... 530/350; 514/21.2

(58) Field of Classification Search
None
See application file for complete search history.

(56) References Cited

U.S. PATENT DOCUMENTS

| | | | |
|---|---|---|---|
| 4,703,004 A | 10/1987 | Hopp et al. |
| 4,782,137 A | 11/1988 | Hopp et al. |
| 4,851,341 A | 7/1989 | Hopp et al. |
| 5,011,912 A | 4/1991 | Hopp et al. |
| 5,817,789 A | 10/1998 | Heartlein et al. |
| 6,114,147 A | 9/2000 | Frenken et al. |
| 6,300,065 B1 | 10/2001 | Keike et al. |
| 6,696,251 B1 | 2/2004 | Wittrup et al. |
| 6,759,243 B2 | 7/2004 | Kranz et al. |
| 7,176,278 B2 | 2/2007 | Prior |
| 2003/0226155 A1 | 12/2003 | Sadeghi et al. |
| 2004/0023334 A1 | 2/2004 | Prior |
| 2006/0105387 A1 | 5/2006 | Prior et al. |
| 2006/0130158 A1 | 6/2006 | Turner et al. |
| 2006/0205037 A1 | 9/2006 | Sadeghi et al. |
| 2007/0031440 A1 | 2/2007 | Prior et al. |
| 2007/0050855 A1 | 3/2007 | Prior et al. |
| 2007/0060512 A1 | 3/2007 | Sadeghi et al. |
| 2007/0066813 A1 | 3/2007 | Prior et al. |
| 2007/0275871 A1 | 11/2007 | Sadeghi et al. |
| 2008/0220002 A1 | 9/2008 | Sadeghi et al. |

FOREIGN PATENT DOCUMENTS

| | | | |
|---|---|---|---|
| WO | WO 01/46698 | 6/2001 |
| WO | WO 03/020746 | 3/2003 |
| WO | WO 2004/019872 | 3/2004 |
| WO | WO 2004/020404 | 3/2004 |
| WO | WO 2004/020405 | 3/2004 |
| WO | WO 2004/020454 | 3/2004 |
| WO | WO 2004/020588 | 3/2004 |
| WO | WO 2004/078777 | 9/2004 |
| WO | WO 2005/021579 | 3/2005 |
| WO | WO 2006/049983 | 5/2006 |
| WO | WO 2006/096515 | 9/2006 |
| WO | WO 2006/138700 | 12/2006 |
| WO | WO 2006/138700 A2 * | 12/2006 | .............. C40B 40/10 |
| WO | WO 2008/012629 | 1/2008 |

OTHER PUBLICATIONS

Definition of derivative, from http://cancerweb.ncl.ac.uk/cgi-bin/omd?query=derivative, pp. 1-5, accessed Jul. 7, 2005.*
Definition of fragment, from http://www.merriam-webster.com/dictionary/fragment, pp. 1-3, accessed May 1, 2013.*
Boder et al. "Yeast Display for Directed Evolution of Protein Expression, Affinity, and Stability" Methods in Enzymology, 2000, vol. 328, pp. 430-439.
Baker et al. 1992, FEBS Lett, 298:215-218.
Alemany et al., 1993, J. Cell Sci., 104:1155-1162.
Food et al., 1994, J. Biol. Chem., 274:7011-7017.
Girard et al., 1995, Immunity, 2:113-123.
Van Kinken et al., 1998, Anal. Biochem., 265:103-116.
Kok, 1990, FEMS Microbioloty Reviews 87:15-42.
Conzelmann et al., EMBO, 9:653-661, 1990.
Lipke and Ovalle, 1998, J. Bacteriol., 180:3735-3740.
Hamada et al., 1999, J. Bacteriol., 181:3886-3889.
Nuoffer et al., 1993, J. Biol. Chem., 268:10558-10563.
De Nobel et al., 1994, Trends, Cell Biol., 4:42-45.
Hamada et al., 1998, Mol. Gen. Genet., 258:53-59.
Van Der Vaart et al., 1998, Biotechnol. Genet Eng. Rev., 15:387-411.
Bush et al., 1991, J. biol. Chem., 266:13811-13814.
Berger et al., 1998, Gene, 66:1-10.
Elloumi et al., 2006, Bomaterials, 27:3451-3458.
Koivunen et al., 1995, Biotechnology, 13:265-270.
Ali et al., J of Biological Chemistry, 1999, 274/84:24066-73.
Hsu et al., J. of Biotechnology, 2004, 111:143-54.
Dubljevic et al., J of Biochem, 1999, 341:11-14.

* cited by examiner

*Primary Examiner* — Julie Ha
*Assistant Examiner* — Li Ni Komatsu
(74) *Attorney, Agent, or Firm* — Pfizer Inc.

(57) ABSTRACT

Fusion proteins comprising a transferrin moiety and integrin binding domain and peptide libraries thereof are disclosed. The present invention includes a method of screening transferrin and integrin peptide libraries displayed in fusion proteins expressed by host cells. The fusion proteins of the present invention include transferrin fusion proteins capable of expression in yeast.

4 Claims, 23 Drawing Sheets

SEQUENCE LISTING

```
<160> NUMBER OF SEQ ID NOS: 98

<210> SEQ ID NO 1
<211> LENGTH: 2318
<212> TYPE: DNA
<213> ORGANISM: Homo sapiens
<220> FEATURE:
<221> NAME/KEY: CDS
<222> LOCATION: (51)..(2147)
<223> OTHER INFORMATION: GenBank Acc. No. NM_001063, transferrin gene
      and protein
<220> FEATURE:
<221> NAME/KEY: sig_peptide
<222> LOCATION: (51)..(107)

<400> SEQUENCE: 1
gcacagaagc gagtccgact gtgctcgctg ctcagcgccg cacccggaag atg agg      56
```

```
                                        Met Arg
                                         1
ctc gcc gtg gga gcc ctg ctg gtc tgc gcc gtc ctg ggg ctg tgt ctg      104
Leu Ala Val Gly Ala Leu Leu Val Cys Ala Val Leu Gly Leu Cys Leu
         5                  10                  15 gct gtc cct gat aaa act gtg aga tgg tgt gca gtg tcg gag cat gag      152
Ala Val Pro Asp Lys Thr Val Arg Trp Cys Ala Val Ser Glu His Glu
     20                  25                  30 gcc act aag tgc cag agt ttc cgc gac cat atg aaa agc gtc att cca      200
Ala Thr Lys Cys Gln Ser Phe Arg Asp His Met Lys Ser Val Ile Pro
 35                  40                  45                  50 tcc gat ggt ccc agt gtt gct tgt gtg aag aaa gcc tcc tac ctt gat      248
Ser Asp Gly Pro Ser Val Ala Cys Val Lys Lys Ala Ser Tyr Leu Asp
                 55                  60                  65 tgc atc agg gcc att gcg gca aac gaa gcg gat gct gtg aca ctg gat      296
Cys Ile Arg Ala Ile Ala Ala Asn Glu Ala Asp Ala Val Thr Leu Asp
             70                  75                  80 gca ggt ttg gtg tat gat gct tac ctg gct ccc aat aac ctg aag cct      344
Ala Gly Leu Val Tyr Asp Ala Tyr Leu Ala Pro Asn Asn Leu Lys Pro
         85                  90                  95 gtg gtg gca gag ttc tat ggg tca aaa gag gat cca cag act ttc tat      392
Val Val Ala Glu Phe Tyr Gly Ser Lys Glu Asp Pro Gln Thr Phe Tyr
    100                 105                 110 tat gct gtt gct gtg gtg aag aag gat agt ggc ttc cag atg aac cag      440
Tyr Ala Val Ala Val Val Lys Lys Asp Ser Gly Phe Gln Met Asn Gln
115                 120                 125                 130 ctt cga ggc aag aag tcc tgc cac acg ggt cta ggc agg tcc gct ggg      488
Leu Arg Gly Lys Lys Ser Cys His Thr Gly Leu Gly Arg Ser Ala Gly
                135                 140                 145 tgg aac atc ccc ata ggc tta ctt tac tgt gac tta cct gag cca cgt      536
Trp Asn Ile Pro Ile Gly Leu Leu Tyr Cys Asp Leu Pro Glu Pro Arg
            150                 155                 160 aaa cct ctt gag aaa gca gtg gcc aat ttc ttc tcg ggc agc tgt gcc      584
Lys Pro Leu Glu Lys Ala Val Ala Asn Phe Phe Ser Gly Ser Cys Ala
        165                 170                 175 cct tgt gcg gat ggg acg gac ttc ccc cag ctg tgt caa ctg tgt cca      632
Pro Cys Ala Asp Gly Thr Asp Phe Pro Gln Leu Cys Gln Leu Cys Pro
    180                 185                 190 ggg tgt ggc tgc tcc acc ctt aac caa tac ttc ggc tac tcg gga gcc      680
Gly Cys Gly Cys Ser Thr Leu Asn Gln Tyr Phe Gly Tyr Ser Gly Ala
195                 200                 205                 210 ttc aag tgt ctg aag gat ggt gct ggg gat gtg gcc ttt gtc aag cac      728
Phe Lys Cys Leu Lys Asp Gly Ala Gly Asp Val Ala Phe Val Lys His
                215                 220                 225 tcg act ata ttt gag aac ttg gca aac aag gct gac agg gac cag tat      776
Ser Thr Ile Phe Glu Asn Leu Ala Asn Lys Ala Asp Arg Asp Gln Tyr
            230                 235                 240 gag ctg ctt tgc ctg gac aac acc cgg aag ccg gta gat gaa tac aag      824
Glu Leu Leu Cys Leu Asp Asn Thr Arg Lys Pro Val Asp Glu Tyr Lys
        245                 250                 255 gac tgc cac ttg gcc cag gtc cct tct cat acc gtc gtg gcc cga agt      872
Asp Cys His Leu Ala Gln Val Pro Ser His Thr Val Val Ala Arg Ser
    260                 265                 270 atg ggc ggc aag gag gac ttg atc tgg gag ctt ctc aac cag gcc cag      920
Met Gly Gly Lys Glu Asp Leu Ile Trp Glu Leu Leu Asn Gln Ala Gln
275                 280                 285                 290 gaa cat ttt ggc aaa gac aaa tca aaa gaa ttc caa cta ttc agc tct      968
Glu His Phe Gly Lys Asp Lys Ser Lys Glu Phe Gln Leu Phe Ser Ser
                295                 300                 305
```

| | | |
|---|---|---|
| cct cat ggg aag gac ctg ctg ttt aag gac tct gcc cac ggg ttt tta<br>Pro His Gly Lys Asp Leu Leu Phe Lys Asp Ser Ala His Gly Phe Leu<br>310 315 320 | | 1016 |
| aaa gtc ccc ccc agg atg gat gcc aag atg tac ctg ggc tat gag tat<br>Lys Val Pro Pro Arg Met Asp Ala Lys Met Tyr Leu Gly Tyr Glu Tyr<br>325 330 335 | | 1064 |
| gtc act gcc atc cgg aat cta cgg gaa ggc aca tgc cca gaa gcc cca<br>Val Thr Ala Ile Arg Asn Leu Arg Glu Gly Thr Cys Pro Glu Ala Pro<br>340 345 350 | | 1112 |
| aca gat gaa tgc aag cct gtg aag tgg tgt gcg ctg agc cac cac gag<br>Thr Asp Glu Cys Lys Pro Val Lys Trp Cys Ala Leu Ser His His Glu<br>355 360 365 370 | | 1160 |
| agg ctc aag tgt gat gag tgg agt gtt aac agt gta ggg aaa ata gag<br>Arg Leu Lys Cys Asp Glu Trp Ser Val Asn Ser Val Gly Lys Ile Glu<br>375 380 385 | | 1208 |
| tgt gta tca gca gag acc acc gaa gac tgc atc gcc aag atc atg aat<br>Cys Val Ser Ala Glu Thr Thr Glu Asp Cys Ile Ala Lys Ile Met Asn<br>390 395 400 | | 1256 |
| gga gaa gct gat gcc atg agc ttg gat gga ggg ttt gtc tac ata gcg<br>Gly Glu Ala Asp Ala Met Ser Leu Asp Gly Gly Phe Val Tyr Ile Ala<br>405 410 415 | | 1304 |
| ggc aag tgt ggt ctg gtg cct gtc ttg gca gaa aac tac aat aag agc<br>Gly Lys Cys Gly Leu Val Pro Val Leu Ala Glu Asn Tyr Asn Lys Ser<br>420 425 430 | | 1352 |
| gat aat tgt gag gat aca cca gag gca ggg tat ttt gct gta gca gtg<br>Asp Asn Cys Glu Asp Thr Pro Glu Ala Gly Tyr Phe Ala Val Ala Val<br>435 440 445 450 | | 1400 |
| gtg aag aaa tca gct tct gac ctc acc tgg gac aat ctg aaa ggc aag<br>Val Lys Lys Ser Ala Ser Asp Leu Thr Trp Asp Asn Leu Lys Gly Lys<br>455 460 465 | | 1448 |
| aag tcc tgc cat acg gca gtt ggc aga acc gct ggc tgg aac atc ccc<br>Lys Ser Cys His Thr Ala Val Gly Arg Thr Ala Gly Trp Asn Ile Pro<br>470 475 480 | | 1496 |
| atg ggc ctg ctc tac aat aag atc aac cac tgc aga ttt gat gaa ttt<br>Met Gly Leu Leu Tyr Asn Lys Ile Asn His Cys Arg Phe Asp Glu Phe<br>485 490 495 | | 1544 |
| ttc agt gaa ggt tgt gcc cct ggg tct aag aaa gac tcc agt ctc tgt<br>Phe Ser Glu Gly Cys Ala Pro Gly Ser Lys Lys Asp Ser Ser Leu Cys<br>500 505 510 | | 1592 |
| aag ctg tgt atg ggc tca ggc cta aac ctg tgt gaa ccc aac aac aaa<br>Lys Leu Cys Met Gly Ser Gly Leu Asn Leu Cys Glu Pro Asn Asn Lys<br>515 520 525 530 | | 1640 |
| gag gga tac tac ggc tac aca ggc gct ttc agg tgt ctg gtt gag aag<br>Glu Gly Tyr Tyr Gly Tyr Thr Gly Ala Phe Arg Cys Leu Val Glu Lys<br>535 540 545 | | 1688 |
| gga gat gtg gcc ttt gtg aaa cac cag act gtc cca cag aac act ggg<br>Gly Asp Val Ala Phe Val Lys His Gln Thr Val Pro Gln Asn Thr Gly<br>550 555 560 | | 1736 |
| gga aaa aac cct gat cca tgg gct aag aat ctg aat gaa aaa gac tat<br>Gly Lys Asn Pro Asp Pro Trp Ala Lys Asn Leu Asn Glu Lys Asp Tyr<br>565 570 575 | | 1784 |
| gag ttg ctg tgc ctt gat ggt acc agg aaa cct gtg gag gag tat gcg<br>Glu Leu Leu Cys Leu Asp Gly Thr Arg Lys Pro Val Glu Glu Tyr Ala<br>580 585 590 | | 1832 |
| aac tgc cac ctg gcc aga gcc ccg aat cac gct gtg gtc aca cgg aaa<br>Asn Cys His Leu Ala Arg Ala Pro Asn His Ala Val Val Thr Arg Lys<br>595 600 605 610 | | 1880 |
| gat aag gaa gct tgc gtc cac aag ata tta cgt caa cag cag cac cta<br>Asp Lys Glu Ala Cys Val His Lys Ile Leu Arg Gln Gln Gln His Leu<br>615 620 625 | | 1928 |

```
ttt gga agc aac gta act gac tgc tcg ggc aac ttt tgt ttg ttc cgg      1976
Phe Gly Ser Asn Val Thr Asp Cys Ser Gly Asn Phe Cys Leu Phe Arg
             630                 635                 640 tcg gaa acc aag gac ctt ctg ttc aga gat gac aca gta tgt ttg gcc      2024
Ser Glu Thr Lys Asp Leu Leu Phe Arg Asp Asp Thr Val Cys Leu Ala
             645                 650                 655 aaa ctt cat gac aga aac aca tat gaa aaa tac tta gga gaa gaa tat      2072
Lys Leu His Asp Arg Asn Thr Tyr Glu Lys Tyr Leu Gly Glu Glu Tyr
             660                 665                 670 gtc aag gct gtt ggt aac ctg aga aaa tgc tcc acc tca tca ctc ctg      2120
Val Lys Ala Val Gly Asn Leu Arg Lys Cys Ser Thr Ser Ser Leu Leu
675                 680                 685                 690 gaa gcc tgc act ttc cgt aga cct taa aatctcagag gtagggctgc            2167
Glu Ala Cys Thr Phe Arg Arg Pro
                    695 caccaaggtg aagatgggaa cgcagatgat ccatgagttt gccctggttt cactggccca    2227 agtggtttgt gctaaccacg tctgtcttca cagctctgtg ttgccatgtg tgctgaacaa    2287 aaaataaaaa ttattattga ttttatattt c                                   2318

<210> SEQ ID NO 2
<211> LENGTH: 698
<212> TYPE: PRT
<213> ORGANISM: Homo sapiens

<400> SEQUENCE: 2

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
                20                  25                  30

His Glu Ala Thr Lys Cys Gln Ser Phe Arg Asp His Met Lys Ser Val
            35                  40                  45

Ile Pro Ser Asp Gly Pro Ser Val Ala Cys Val Lys Lys Ala Ser Tyr
        50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240
```

-continued

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

```
Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
            690                 695

<210> SEQ ID NO 3
<211> LENGTH: 679
<212> TYPE: PRT
<213> ORGANISM: Homo sapiens
<220> FEATURE:
<221> NAME/KEY: MISC_FEATURE
<223> OTHER INFORMATION: Mature Transferrin Protein

<400> SEQUENCE: 3

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
    50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
                85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320
```

```
Thr Ala Ile Arg Asn Leu Arg Glu Gly Thr Cys Pro Glu Ala Pro Thr
            325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
            355                 360                 365

Val Ser Ala Glu Thr Thr Glu Asp Cys Ile Ala Lys Ile Met Asn Gly
370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
            405                 410                 415

Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
            435                 440                 445

Ser Cys His Thr Ala Val Gly Arg Thr Ala Gly Trp Asn Ile Pro Met
            450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
            485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
            515                 520                 525

Asp Val Ala Phe Val Lys His Gln Thr Val Pro Gln Asn Thr Gly Gly
            530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
            565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
            595                 600                 605

Gly Ser Asn Val Thr Asp Cys Ser Gly Asn Phe Cys Leu Phe Arg Ser
610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
            645                 650                 655

Lys Ala Val Gly Asn Leu Arg Lys Cys Ser Thr Ser Ser Leu Leu Glu
            660                 665                 670

Ala Cys Thr Phe Arg Arg Pro
            675

<210> SEQ ID NO 4
<211> LENGTH: 12
<212> TYPE: PRT
<213> ORGANISM: Artificial sequence
<220> FEATURE:
<223> OTHER INFORMATION: Neutrophil splice variant sequence

<400> SEQUENCE: 4
```

Glu Asp Cys Ile Ala Leu Lys Gly Glu Ala Asp Ala
1               5                   10

<210> SEQ ID NO 5
<211> LENGTH: 732
<212> TYPE: DNA
<213> ORGANISM: Homo sapiens
<220> FEATURE:
<221> NAME/KEY: misc_feature
<223> OTHER INFORMATION: Human MUCI

<400> SEQUENCE: 5

| | | | | | |
|---|---|---|---|---|---|
| acaggttctg | gtcatgcaag | ctctacccca | ggtggagaaa | aggagacttc | ggctacccag | 60 |
| agaagttcag | tgcccagctc | tactgagaag | aatgctgtga | gtatgaccag | cagcgtactc | 120 |
| tccagccaca | gccccggttc | aggctcctcc | accactcagg | acaggatgt | cactctggcc | 180 |
| ccggccacgg | aaccagcttc | aggttcagct | gccacctggg | gacaggatgt | cacctcggtc | 240 |
| ccagtcacca | ggccagccct | gggctccacc | accccgccag | cccacgatgt | cacctcagcc | 300 |
| ccggacaaca | agccagcccc | gggctccacc | gccccccag | cccacggtgt | cacctcggcc | 360 |
| ccggacaaca | ggcccgcctt | ggcgtccacc | gcccctccag | tccacaatgt | cacctcggcc | 420 |
| tcaggctctg | catcaggctc | agcttctact | ctggtgcaca | acggcacctc | tgccagggct | 480 |
| accacaaccc | cagccagcaa | gagcactcca | ttctcaattc | ccagccacca | ctctgatact | 540 |
| cctaccaccc | ttgccagcca | tagcaccaag | actgatgcca | gtagcactca | ccatagcacg | 600 |
| gtacctcctc | tcacctcctc | caatcacagc | acttctcccc | agttgtctac | tggggtctct | 660 |
| ttcttttttcc | tgtcttttca | catttcaaac | ctccagttta | attcctctct | ggaagatccc | 720 |
| agcaccgact | ac | | | | | 732 |

<210> SEQ ID NO 6
<211> LENGTH: 744
<212> TYPE: DNA
<213> ORGANISM: Artificial Sequence
<220> FEATURE:
<223> OTHER INFORMATION: hMUCI with SpeI and HindIII sites

<400> SEQUENCE: 6

| | | | | | |
|---|---|---|---|---|---|
| actagtacag | gttctggtca | tgcaagctct | accccaggtg | gagaaaagga | gacttcggct | 60 |
| acccagagaa | gttcagtgcc | cagctctact | gagaagaatg | ctgtgagtat | gaccagcagc | 120 |
| gtactctcca | gccacagccc | cggttcaggc | tcctccacca | ctcagggaca | ggatgtcact | 180 |
| ctggccccgg | ccacggaacc | agcttcaggt | tcagctgcca | cctggggaca | ggatgtcacc | 240 |
| tcggtcccag | tcaccaggcc | agccctgggc | tccaccaccc | cgccagccca | cgatgtcacc | 300 |
| tcagccccgg | acaacaagcc | agcccgggc | tccaccgccc | cccagccca | cggtgtcacc | 360 |
| tcggccccgg | acaacaggcc | cgccttggcg | tccaccgccc | ctccagtcca | caatgtcacc | 420 |
| tcggcctcag | gctctgcatc | aggctcagct | tctactctgg | tgcacaacgg | cacctctgcc | 480 |
| agggctacca | caaccccagc | cagcaagagc | actccattct | caattcccag | ccaccactct | 540 |
| gatactccta | ccacccttgc | cagccatagc | accaagactg | atgccagtag | cactcaccat | 600 |
| agcacggtac | ctcctctcac | ctcctccaat | cacagcactt | ctccccagtt | gtctactggg | 660 |
| gtctctttct | ttttcctgtc | ttttcacatt | tcaaacctcc | agtttaattc | ctctctggaa | 720 |
| gatcccagca | ccgactacaa | gctt | | | | 744 |

<210> SEQ ID NO 7

```
<211> LENGTH: 32
<212> TYPE: DNA
<213> ORGANISM: Artificial Sequence
<220> FEATURE:
<223> OTHER INFORMATION: Primer

<400> SEQUENCE: 7
tactagtatc aagcttatct ctagataata at                              32

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
agctattatt atctagagat aagcttgata ctagta                          36

<210> SEQ ID NO 9
<211> LENGTH: 86
<212> TYPE: DNA
<213> ORGANISM: Artificial Sequence
<220> FEATURE:
<223> OTHER INFORMATION: Primer

<400> SEQUENCE: 9
atcaagcttt ctggttctgc agtcgctaca tactctgttc cttctatctc gagtacttac   60
caaggtgctg ctaatatcaa ggttct                                      86

<210> SEQ ID NO 10
<211> LENGTH: 80
<212> TYPE: DNA
<213> ORGANISM: Artificial Sequence
<220> FEATURE:
<223> OTHER INFORMATION: Primer

<400> SEQUENCE: 10
ttatctagat tattagaata caactggaag agcgagtagc aaccacataa agtttccaag   60
aaccttgata ttagcagcac                                             80

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
gtagtcggtg ctgggatctt ccagag                                      26

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
gctgctcctc acagtgctta cagttg                                      26

<210> SEQ ID NO 13
<211> LENGTH: 32
<212> TYPE: DNA
<213> ORGANISM: Artificial Sequence
```

```
<220> FEATURE:
<223> OTHER INFORMATION: Primer

<400> SEQUENCE: 13
cgtactagta caggttctgg tcatgcaagc tc                                32

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
tctaagcttg tagtcggtgc tgggatcttc c                                 31

<210> SEQ ID NO 15
<211> LENGTH: 40
<212> TYPE: PRT
<213> ORGANISM: Saccharomyces cerevisiae
<220> FEATURE:
<221> NAME/KEY: MISC_FEATURE
<223> OTHER INFORMATION: Yeast YIR019C GPI anchor

<400> SEQUENCE: 15

Ser Gly Ser Ala Val Ala Thr Tyr Ser Val Pro Ser Ile Ser Ser Thr
1               5                   10                  15

Tyr Gln Gly Ala Ala Asn Ile Lys Val Leu Gly Asn Phe Met Trp Leu
            20                  25                  30

Leu Leu Ala Leu Pro Val Val Phe
        35                  40

<210> SEQ ID NO 16
<211> LENGTH: 2094
<212> TYPE: DNA
<213> ORGANISM: Homo sapiens
<220> FEATURE:
<221> NAME/KEY: misc_feature
<223> OTHER INFORMATION: Modified transferrin
<220> FEATURE:
<221> NAME/KEY: misc_feature
<223> OTHER INFORMATION: Tf expression cassette

<400> SEQUENCE: 16
atgaggctcg ccgtgggagc cctgctggtc tgcgccgtcc tggggctgtg tctggcggta      60
cctgataaaa ctgtgagatg gtgtgcagtg tcggagcatg aggccactaa gtgccagagt     120
ttccgcgacc atatgaaaag cgtcattcca tccgatggtc ccagtgttgc ttgtgtgaag     180
aaagcctcct accttgattg catcagggcc attgcggcaa acgaagcgga tgctgtgaca     240
ctggatgcag gttggtgta tgatgcttac ctggctccca taacctgaa gcctgtggtg      300 gcagagttct atgggtcaaa agaggatcca cagactttct attatgctgt tgctgtggtg     360
aagaaggata gtggcttcca gatgaaccag cttcgaggca gaagtcctg ccacacgggt     420 ctaggcaggt ccgctgggtg gaacatcccc ataggcttac tttactgtga cttacctgag     480
ccacgtaaac tcttgagaa agcagtggcc aatttcttct cgggcagctg tgccccttgt     540
gcggatggga cggacttccc ccagctgtgt caactgtgtc cagggtgtgg ctgctccacc     600
cttaaccaat acttcggcta ctcgggagcc ttcaagtgtc tgaaggatgg tgctgggat      660 gtggcctttg tcaagcactc gactatattt gagaacttgg caaacaaggc tgacagggac     720
cagtatgagc tgctttgcct ggacaacacc cggaagccgg tagatgaata caaggactgc     780
```

| | |
|---|---|
| cacttggccc aggtcccttc tcataccgtc gtggcccgaa gtatgggcgg caaggaggac | 840 |
| ttgatctggg agcttctcaa ccaggcccag gaacattttg gcaaagacaa atcaaaagaa | 900 |
| ttccaactat tcagctctcc tcatgggaag gacctgctgt ttaaggactc tgcccacggg | 960 |
| ttttaaaag tccccccag gatggatgcc aagatgtacc tgggctatga gtatgtcact | 1020 |
| gccatccgga atctacggga aggcacatgc ccagaagccc aacagatga atgcaagcct | 1080 |
| gtgaagtggt gtgcgctgag ccaccacgag aggctcaagt gtgatgagtg gagtgttaac | 1140 |
| agtgtaggga aaatagagtg tgtatcagca gagaccaccg aagactgcat cgccaagatc | 1200 |
| atgaatggag aagctgatgc catgagcttg gatggagggt ttgtctacat agcgggcaag | 1260 |
| tgtggtctgg tgcctgtctt ggcagaaaac tacaataagg ctgataattg tgaggataca | 1320 |
| ccagaggcag ggtattttgc tgtagcagtg gtgaagaaat cagcttctga cctcacctgg | 1380 |
| gacaatctga aaggcaagaa gtcctgccat acggcagttg gcagaaccgc tggctggaac | 1440 |
| atccccatgg gcctgctcta caataagatc aaccactgca gatttgatga attttttcagt | 1500 |
| gaaggttgtg cccctgggtc taagaaagac tccagtctct gtaagctgtg tatgggctca | 1560 |
| ggcctaaaacc tctgtgaacc caacaacaaa gagggatact acggctacac aggcgctttc | 1620 |
| aggtgtctgg ttgagaaggg agatgtggcc tttgtgaaac accagactgt cccacagaac | 1680 |
| actggggaa aaaaccctga tccatgggct aagaatctga atgaaaaaga ctatgagttg | 1740 |
| ctgtgccttg atggtactag gaaacctgtg gaggagtatg cgaactgcca cctggccaga | 1800 |
| gccccgaatc acgctgtggt cacacggaaa gataaggaag catgcgtcca caagatatta | 1860 |
| cgtcaacagc agcaccctatt tggaagcaac gtagctgact gctcgggcaa cttttgtttg | 1920 |
| ttccggtcgg aaaccaagga ccttctgttc agagatgaca cagtatgttt ggccaaactt | 1980 |
| catgacagaa acacatatga aaaatactta ggagaagaat atgtcaaggc tgttggtaac | 2040 |
| ctgagaaaat gctccaccctc atcactcctg gaagcctgca ctttccgtcg acct | 2094 |

```
<210> SEQ ID NO 17
<211> LENGTH: 5
<212> TYPE: PRT
<213> ORGANISM: Unknown
<220> FEATURE:
<223> OTHER INFORMATION: Spacer peptide
<220> FEATURE:
<221> NAME/KEY: REPEAT
<222> LOCATION: (1)..(5)
<223> OTHER INFORMATION: Sequence may be repeated

<400> SEQUENCE: 17

Gly Gly Gly Gly Ser
1               5

<210> SEQ ID NO 18
<211> LENGTH: 6
<212> TYPE: PRT
<213> ORGANISM: Unknown
<220> FEATURE:
<223> OTHER INFORMATION: Linker peptide
<220> FEATURE:
<221> NAME/KEY: REPEAT
<222> LOCATION: (1)..(6)
<223> OTHER INFORMATION: May be repeated

<400> SEQUENCE: 18

Pro Glu Ala Pro Thr Asp
1               5
```

```
<210> SEQ ID NO 19
<211> LENGTH: 88
<212> TYPE: DNA
<213> ORGANISM: Artificial Sequence
<220> FEATURE:
<223> OTHER INFORMATION: P1172 primer
<220> FEATURE:
<221> NAME/KEY: misc_feature
<222> LOCATION: (20)..(64)
<223> OTHER INFORMATION: n is a, c, g, or t

<400> SEQUENCE: 19
ccaactattc agctctcctn nnnnnnnnnn nnnnnnnnnn nnnnnnnnnn nnnnnnnnn      60 nnnncatggg aaggacctgc tgtttaag                                        88

<210> SEQ ID NO 20
<211> LENGTH: 19
<212> TYPE: DNA
<213> ORGANISM: Artificial Sequence
<220> FEATURE:
<223> OTHER INFORMATION: P1173 primer

<400> SEQUENCE: 20
aggagagctg aatagttgg                                                  19

<210> SEQ ID NO 21
<211> LENGTH: 22
<212> TYPE: DNA
<213> ORGANISM: Artificial Sequence
<220> FEATURE:
<223> OTHER INFORMATION: P1174 primer

<400> SEQUENCE: 21
ctggatgcag gtttggtgta tg                                              22

<210> SEQ ID NO 22
<211> LENGTH: 22
<212> TYPE: DNA
<213> ORGANISM: Artificial Sequence
<220> FEATURE:
<223> OTHER INFORMATION: P1227 primer

<400> SEQUENCE: 22
tcatgatctt ggcgatgcag tc                                              22

<210> SEQ ID NO 23
<211> LENGTH: 8
<212> TYPE: PRT
<213> ORGANISM: Artificial Sequence
<220> FEATURE:
<223> OTHER INFORMATION: Flag-tag sequence

<400> SEQUENCE: 23

Asp Tyr Lys Asp Asp Asp Asp Lys
1               5

<210> SEQ ID NO 24
<211> LENGTH: 34
<212> TYPE: DNA
<213> ORGANISM: Artificial Sequence
<220> FEATURE:
<223> OTHER INFORMATION: PCR primer for yeast gene AGA1

<400> SEQUENCE: 24
cagatctaga acaaccgcta tcagctcatt atcc                                 34
```

```
<210> SEQ ID NO 25
<211> LENGTH: 32
<212> TYPE: DNA
<213> ORGANISM: Artificial Sequence
<220> FEATURE:
<223> OTHER INFORMATION: PCR primer for yeast gene AGA1

<400> SEQUENCE: 25
cagaaagctt agtagtggaa acttctgtag tg                                      32

<210> SEQ ID NO 26
<211> LENGTH: 40
<212> TYPE: PRT
<213> ORGANISM: Artificial Sequence
<220> FEATURE:
<223> OTHER INFORMATION: Modified huMDP GPI sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 26

Xaa Gln Xaa Gly Gly Ser Xaa Xaa Thr Ile Gly Gly Tyr Ser Gly Ala
1               5                   10                  15

Ala Ser Ser Leu Gln Arg Thr Ile Gly Leu Leu Leu Ala Ser Leu Ala
            20                  25                  30

Pro Leu Val Leu Ala Ser Leu Leu
        35                  40

<210> SEQ ID NO 27
<211> LENGTH: 83
<212> TYPE: DNA
<213> ORGANISM: Artificial Sequence
<220> FEATURE:
<223> OTHER INFORMATION: P2035 primer
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 27
ctacaagctt nnkcaannkg gtggttctnn knnkactatt ggtggttatt ctggtgctgc        60
ttcttccttg cagagaacta ttg                                               83

<210> SEQ ID NO 28
<211> LENGTH: 84
<212> TYPE: DNA
<213> ORGANISM: Artificial Sequence
<220> FEATURE:
<223> OTHER INFORMATION: P2036 primer
```

<400> SEQUENCE: 28
gatgtctaga ttattataac aaagaagcta aaccaatgg agctaaagaa gccaataaca    60
aaccaatagt tctctgcaag gaag    84

<210> SEQ ID NO 29
<211> LENGTH: 138
<212> TYPE: DNA
<213> ORGANISM: Artificial Sequence
<220> FEATURE:
<223> OTHER INFORMATION: DNA sequence resulting from restriction enzyme
      digestion of anneal and extend reaction of oligos P2035 and P2036
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 29
aagcttnnkc aannkggtgg ttctnnknnk actattggtg gttattctgg tgctgcttct    60
tccttgcaga gaactattgg tttgttattg gcttctttag ctccattggt tttagcttct   120
ttgttataat aatctaga   138

<210> SEQ ID NO 30
<211> LENGTH: 42
<212> TYPE: PRT
<213> ORGANISM: Artificial Sequence
<220> FEATURE:
<223> OTHER INFORMATION: Amino acid sequence of DNA sequence that
      resulted from anneal and extend reaction of oligos P2035 and P2036
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 30

Lys Leu Xaa Gln Xaa Gly Gly Ser Xaa Xaa Thr Ile Gly Gly Tyr Ser
1               5                   10                  15

Gly Ala Ala Ser Ser Leu Gln Arg Thr Ile Gly Leu Leu Leu Ala Ser
            20                  25                  30

Leu Ala Pro Leu Val Leu Ala Ser Leu Leu
        35                  40

<210> SEQ ID NO 31
<211> LENGTH: 24
<212> TYPE: DNA
<213> ORGANISM: Artificial Sequence
<220> FEATURE:
<223> OTHER INFORMATION: Consensus GPI anchor sequence

```
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 31
nnkcaannkg gtggttctnn knnk                                            24

<210> SEQ ID NO 32
<211> LENGTH: 24
<212> TYPE: DNA
<213> ORGANISM: Artificial Sequence
<220> FEATURE:
<223> OTHER INFORMATION: Clone 23 GPI anchor sequence

<400> SEQUENCE: 32
tgtcaatagg gtggttctag gcct                                            24

<210> SEQ ID NO 33
<211> LENGTH: 24
<212> TYPE: DNA
<213> ORGANISM: Artificial Sequence
<220> FEATURE:
<223> OTHER INFORMATION: Clone 8 GPI anchor sequence

<400> SEQUENCE: 33
tgtcaaattg gtggttctta gtgt                                            24

<210> SEQ ID NO 34
<211> LENGTH: 6
<212> TYPE: PRT
<213> ORGANISM: Artificial Sequence
<220> FEATURE:
<223> OTHER INFORMATION: Clone 8 GPI anchor sequence

<400> SEQUENCE: 34

Cys Gln Ile Gly Gly Ser
1               5

<210> SEQ ID NO 35
<211> LENGTH: 24
<212> TYPE: DNA
<213> ORGANISM: Artificial Sequence
<220> FEATURE:
<223> OTHER INFORMATION: Clone 15 GPI anchor sequence

<400> SEQUENCE: 35
cagcaatatg gtggttctgt ggat                                            24

<210> SEQ ID NO 36
<211> LENGTH: 8
<212> TYPE: PRT
<213> ORGANISM: Artificial Sequence
<220> FEATURE:
<223> OTHER INFORMATION: Clone 15 GPI anchor sequence

<400> SEQUENCE: 36
```

Glu Gln Tyr Gly Gly Ser Val Asp
1               5

<210> SEQ ID NO 37
<211> LENGTH: 24
<212> TYPE: DNA
<213> ORGANISM: Artificial Sequence
<220> FEATURE:
<223> OTHER INFORMATION: Clone 14 GPI anchor sequence

<400> SEQUENCE: 37
tctcaagttg gtggttctac ttgg                                          24

<210> SEQ ID NO 38
<211> LENGTH: 8
<212> TYPE: PRT
<213> ORGANISM: Artificial Sequence
<220> FEATURE:
<223> OTHER INFORMATION: Clone 14 GPI anchor sequence

<400> SEQUENCE: 38

Ser Gln Val Gly Gly Ser Thr Trp
1               5

<210> SEQ ID NO 39
<211> LENGTH: 24
<212> TYPE: DNA
<213> ORGANISM: Artificial Sequence
<220> FEATURE:
<223> OTHER INFORMATION: Clone 5 GPI anchor sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 39
nnkcaannkg gtggttctnn knnk                                          24

<210> SEQ ID NO 40
<211> LENGTH: 24
<212> TYPE: DNA
<213> ORGANISM: Artificial Sequence
<220> FEATURE:
<223> OTHER INFORMATION: Clone 2 GPI anchor sequence

<400> SEQUENCE: 40
catcaaggtg gtggttctat tcgg                                          24

<210> SEQ ID NO 41
<211> LENGTH: 8
<212> TYPE: PRT
<213> ORGANISM: Artificial Sequence
<220> FEATURE:
<223> OTHER INFORMATION: Clone 2 GPI anchor sequence

<400> SEQUENCE: 41

His Gln Gly Gly Gly Ser Ile Arg
1               5

<210> SEQ ID NO 42
<211> LENGTH: 24
<212> TYPE: DNA
<213> ORGANISM: Artificial Sequence
<220> FEATURE:
<223> OTHER INFORMATION: Clone 6 GPI anchor sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 42
nnkcaannkg gtggttctnn knnk                                      24

<210> SEQ ID NO 43
<211> LENGTH: 24
<212> TYPE: DNA
<213> ORGANISM: Artificial Sequence
<220> FEATURE:
<223> OTHER INFORMATION: Clone 12 GPI anchor sequence

<400> SEQUENCE: 43
catcaattgg gtggttctgt tacg                                      24

<210> SEQ ID NO 44
<211> LENGTH: 8
<212> TYPE: PRT
<213> ORGANISM: Artificial Sequence
<220> FEATURE:
<223> OTHER INFORMATION: Clone 12 GPI anchor sequence

<400> SEQUENCE: 44

His Gln Leu Gly Gly Ser Val Thr
1               5

<210> SEQ ID NO 45
<211> LENGTH: 24
<212> TYPE: DNA
<213> ORGANISM: Artificial Sequence
<220> FEATURE:
<223> OTHER INFORMATION: Clone 18 GPI anchor sequence

<400> SEQUENCE: 45
tatcaatcgg gtggttctgg gact                                      24

<210> SEQ ID NO 46
<211> LENGTH: 8
<212> TYPE: PRT
<213> ORGANISM: Artificial Sequence
<220> FEATURE:
<223> OTHER INFORMATION: Clone 18 GPI anchor sequence

<400> SEQUENCE: 46

Tyr Gln Ser Gly Gly Ser Gly Thr

<210> SEQ ID NO 47
<211> LENGTH: 24
<212> TYPE: DNA
<213> ORGANISM: Artificial Sequence
<220> FEATURE:
<223> OTHER INFORMATION: Clone 13 GPI anchor sequence

<400> SEQUENCE: 47
gggcaatatg gtggttctta gtgg                                          24

<210> SEQ ID NO 48
<211> LENGTH: 6
<212> TYPE: PRT
<213> ORGANISM: Artificial Sequence
<220> FEATURE:
<223> OTHER INFORMATION: Clone 13 GPI anchor sequence

<400> SEQUENCE: 48

Gly Gln Tyr Gly Gly Ser
1               5

<210> SEQ ID NO 49
<211> LENGTH: 24
<212> TYPE: DNA
<213> ORGANISM: Artificial Sequence
<220> FEATURE:
<223> OTHER INFORMATION: Clone 1 GPI anchor sequence

<400> SEQUENCE: 49
gtgcaagcgg gtggttctga ttag                                          24

<210> SEQ ID NO 50
<211> LENGTH: 7
<212> TYPE: PRT
<213> ORGANISM: Artificial Sequence
<220> FEATURE:
<223> OTHER INFORMATION: Clone 1 GPI anchor sequence

<400> SEQUENCE: 50

Val Gln Ala Gly Gly Ser Asp
1               5

<210> SEQ ID NO 51
<211> LENGTH: 24
<212> TYPE: DNA
<213> ORGANISM: Artificial Sequence
<220> FEATURE:
<223> OTHER INFORMATION: Clone 4 GPI anchor sequence

<400> SEQUENCE: 51
tagcaaatgg gtggttctac taag                                          24

<210> SEQ ID NO 52
<211> LENGTH: 24
<212> TYPE: DNA
<213> ORGANISM: Artificial Sequence
<220> FEATURE:
<223> OTHER INFORMATION: Clone 21 GPI anchor sequence

<400> SEQUENCE: 52
tagcaaacgg gtggttcttc ttat                                          24

<210> SEQ ID NO 53
<211> LENGTH: 24

```
<212> TYPE: DNA
<213> ORGANISM: Artificial Sequence
<220> FEATURE:
<223> OTHER INFORMATION: Clone 3 GPI anchor sequence

<400> SEQUENCE: 53
aagcaacggg gtggttctta gact                                               24

<210> SEQ ID NO 54
<211> LENGTH: 6
<212> TYPE: PRT
<213> ORGANISM: Artificial Sequence
<220> FEATURE:
<223> OTHER INFORMATION: Clone 3 GPI anchor sequence

<400> SEQUENCE: 54

Lys Gln Pro Gly Gly Ser
1               5

<210> SEQ ID NO 55
<211> LENGTH: 24
<212> TYPE: DNA
<213> ORGANISM: Artificial Sequence
<220> FEATURE:
<223> OTHER INFORMATION: Clone 7 GPI anchor sequence

<400> SEQUENCE: 55
ctgcaatgtg gtggttctta gtgg                                               24

<210> SEQ ID NO 56
<211> LENGTH: 6
<212> TYPE: PRT
<213> ORGANISM: Artificial Sequence
<220> FEATURE:
<223> OTHER INFORMATION: Clone 7 GPI anchor sequence

<400> SEQUENCE: 56

Leu Gln Lys Gly Gly Ser
1               5

<210> SEQ ID NO 57
<211> LENGTH: 24
<212> TYPE: DNA
<213> ORGANISM: Artificial Sequence
<220> FEATURE:
<223> OTHER INFORMATION: Clone 16 GPI anchor sequence

<400> SEQUENCE: 57
tagcaactgg gtggttcttt tggg                                               24

<210> SEQ ID NO 58
<211> LENGTH: 24
<212> TYPE: DNA
<213> ORGANISM: Artificial Sequence
<220> FEATURE:
<223> OTHER INFORMATION: Clone 17 GPI anchor sequence

<400> SEQUENCE: 58
tagcaatatg gtggttctgt tcta                                               24

<210> SEQ ID NO 59
<211> LENGTH: 24
<212> TYPE: DNA
<213> ORGANISM: Artificial Sequence
<220> FEATURE:
<223> OTHER INFORMATION: Clone 19 GPI anchor sequence
```

```
<400> SEQUENCE: 59
cttcaagtgg gtggttcttt gtag                                              24

<210> SEQ ID NO 60
<211> LENGTH: 7
<212> TYPE: PRT
<213> ORGANISM: Artificial Sequence
<220> FEATURE:
<223> OTHER INFORMATION: Clone 19 GPI anchor sequence

<400> SEQUENCE: 60

Leu Gln Val Gly Gly Ser Leu
1               5

<210> SEQ ID NO 61
<211> LENGTH: 24
<212> TYPE: DNA
<213> ORGANISM: Artificial Sequence
<220> FEATURE:
<223> OTHER INFORMATION: Clone 24 GPI anchor sequence

<400> SEQUENCE: 61
tagcaatttg gtggttctca tgcg                                              24

<210> SEQ ID NO 62
<211> LENGTH: 24
<212> TYPE: DNA
<213> ORGANISM: Artificial Sequence
<220> FEATURE:
<223> OTHER INFORMATION: Clone 9 GPI anchor sequence

<400> SEQUENCE: 62
cggcaacggg gtggttctaa gtgg                                              24

<210> SEQ ID NO 63
<211> LENGTH: 8
<212> TYPE: PRT
<213> ORGANISM: Artificial Sequence
<220> FEATURE:
<223> OTHER INFORMATION: Clone 9 GPI anchor sequence

<400> SEQUENCE: 63

Arg Gln Arg Gly Gly Ser Lys Trp
1               5

<210> SEQ ID NO 64
<211> LENGTH: 24
<212> TYPE: DNA
<213> ORGANISM: Artificial Sequence
<220> FEATURE:
<223> OTHER INFORMATION: Clone 20 GPI anchor sequence

<400> SEQUENCE: 64
tcgcaaactg gtggttctgt tgct                                              24

<210> SEQ ID NO 65
<211> LENGTH: 8
<212> TYPE: PRT
<213> ORGANISM: Artificial Sequence
<220> FEATURE:
<223> OTHER INFORMATION: Clone 20 GPI anchor sequence

<400> SEQUENCE: 65

Ser Gln Thr Gly Gly Ser Val Ala
1               5
```

```
<210> SEQ ID NO 66
<211> LENGTH: 2215
<212> TYPE: DNA
<213> ORGANISM: Homo sapiens
<220> FEATURE:
<221> NAME/KEY: sig_peptide
<222> LOCATION: (40)..(93)
<220> FEATURE:
<221> NAME/KEY: CDS
<222> LOCATION: (40)..(1866)
<220> FEATURE:
<221> NAME/KEY: mat_peptide
<222> LOCATION: (112)..(1866)

<400> SEQUENCE: 66 agctttctc ttctgtcaac cccacacgcc tttggcaca atg aag tgg gta acc         54
                                           Met Lys Trp Val Thr
                                                           -20 ttt att tcc ctt ctt ttt ctc ttt agc tcg gct tat tcc agg ggt gtg      102
Phe Ile Ser Leu Leu Phe Leu Phe Ser Ser Ala Tyr Ser Arg Gly Val
            -15                 -10                 -5 ttt cgt cga gat gca cac aag agt gag gtt gct cat cgg ttt aaa gat      150
Phe Arg Arg Asp Ala His Lys Ser Glu Val Ala His Arg Phe Lys Asp
         -1  1               5                  10 ttg gga gaa gaa aat ttc aaa gcc ttg gtg ttg att gcc ttt gct cag      198
Leu Gly Glu Glu Asn Phe Lys Ala Leu Val Leu Ile Ala Phe Ala Gln
 15                 20                  25 tat ctt cag cag tgt cca ttt gaa gat cat gta aaa tta gtg aat gaa      246
Tyr Leu Gln Gln Cys Pro Phe Glu Asp His Val Lys Leu Val Asn Glu
 30              35                  40                  45 gta act gaa ttt gca aaa aca tgt gtt gct gat gag tca gct gaa aat      294
Val Thr Glu Phe Ala Lys Thr Cys Val Ala Asp Glu Ser Ala Glu Asn
                 50                  55                  60 tgt gac aaa tca ctt cat acc ctt ttt gga gac aaa tta tgc aca gtt      342
Cys Asp Lys Ser Leu His Thr Leu Phe Gly Asp Lys Leu Cys Thr Val
                     65                  70                  75 gca act ctt cgt gaa acc tat ggt gaa atg gct gac tgc tgt gca aaa      390
Ala Thr Leu Arg Glu Thr Tyr Gly Glu Met Ala Asp Cys Cys Ala Lys
             80                  85                  90 caa gaa cct gag aga aat gaa tgc ttc ttg caa cac aaa gat gac aac      438
Gln Glu Pro Glu Arg Asn Glu Cys Phe Leu Gln His Lys Asp Asp Asn
 95                 100                 105 cca aac ctc ccc cga ttg gtg aga cca gag gtt gat gtg atg tgc act      486
Pro Asn Leu Pro Arg Leu Val Arg Pro Glu Val Asp Val Met Cys Thr
110                 115                 120                 125 gct ttt cat gac aat gaa gag aca ttt ttg aaa aaa tac tta tat gaa      534
Ala Phe His Asp Asn Glu Glu Thr Phe Leu Lys Lys Tyr Leu Tyr Glu
                130                 135                 140 att gcc aga aga cat cct tac ttt tat gcc ccg gaa ctc ctt ttc ttt      582
Ile Ala Arg Arg His Pro Tyr Phe Tyr Ala Pro Glu Leu Leu Phe Phe
            145                 150                 155 gct aaa agg tat aaa gct gct ttt aca gaa tgt tgc caa gct gct gat      630
Ala Lys Arg Tyr Lys Ala Ala Phe Thr Glu Cys Cys Gln Ala Ala Asp
        160                 165                 170 aaa gct gcc tgc ctg ttg cca aag ctc gat gaa ctt cgg gat gaa ggg      678
Lys Ala Ala Cys Leu Leu Pro Lys Leu Asp Glu Leu Arg Asp Glu Gly
    175                 180                 185 aag gct tcg tct gcc aaa cag aga ctc aag tgt gcc agt ctc caa aaa      726
Lys Ala Ser Ser Ala Lys Gln Arg Leu Lys Cys Ala Ser Leu Gln Lys
190                 195                 200                 205 ttt gga gaa aga gct ttc aaa gca tgg gca gta gct cgc ctg agc cag      774
Phe Gly Glu Arg Ala Phe Lys Ala Trp Ala Val Ala Arg Leu Ser Gln
```

-continued

```
                       210                 215                 220
aga ttt ccc aaa gct gag ttt gca gaa gtt tcc aag tta gtg aca gat       822
Arg Phe Pro Lys Ala Glu Phe Ala Glu Val Ser Lys Leu Val Thr Asp
            225                 230                 235 ctt acc aaa gtc cac acg gaa tgc tgc cat gga gat ctg ctt gaa tgt       870
Leu Thr Lys Val His Thr Glu Cys Cys His Gly Asp Leu Leu Glu Cys
        240                 245                 250 gct gat gac agg gcg gac ctt gcc aag tat atc tgt gaa aat caa gat       918
Ala Asp Asp Arg Ala Asp Leu Ala Lys Tyr Ile Cys Glu Asn Gln Asp
    255                 260                 265 tcg atc tcc agt aaa ctg aag gaa tgc tgt gaa aaa cct ctg ttg gaa       966
Ser Ile Ser Ser Lys Leu Lys Glu Cys Cys Glu Lys Pro Leu Leu Glu
270                 275                 280                 285 aaa tcc cac tgc att gcc gaa gtg gaa aat gat gag atg cct gct gac      1014
Lys Ser His Cys Ile Ala Glu Val Glu Asn Asp Glu Met Pro Ala Asp
                290                 295                 300 ttg cct tca tta gct gct gat ttt gtt gaa agt aag gat gtt tgc aaa      1062
Leu Pro Ser Leu Ala Ala Asp Phe Val Glu Ser Lys Asp Val Cys Lys
            305                 310                 315 aac tat gct gag gca aag gat gtc ttc ctg ggc atg ttt ttg tat gaa      1110
Asn Tyr Ala Glu Ala Lys Asp Val Phe Leu Gly Met Phe Leu Tyr Glu
        320                 325                 330 tat gca aga agg cat cct gat tac tct gtc gtg ctg ctg aga ctt           1158
Tyr Ala Arg Arg His Pro Asp Tyr Ser Val Val Leu Leu Arg Leu
    335                 340                 345 gcc aag aca tat gaa acc act cta gag aag tgc tgt gcc gct gca gat      1206
Ala Lys Thr Tyr Glu Thr Thr Leu Glu Lys Cys Cys Ala Ala Ala Asp
350                 355                 360                 365 cct cat gaa tgc tat gcc aaa gtg ttc gat gaa ttt aaa cct ctt gtg      1254
Pro His Glu Cys Tyr Ala Lys Val Phe Asp Glu Phe Lys Pro Leu Val
                370                 375                 380 gaa gag cct cag aat tta atc aaa caa aat tgt gag ctt ttt gag cag      1302
Glu Glu Pro Gln Asn Leu Ile Lys Gln Asn Cys Glu Leu Phe Glu Gln
            385                 390                 395 ctt gga gag tac aaa ttc cag aat gcg cta tta gtt cgt tac acc aag      1350
Leu Gly Glu Tyr Lys Phe Gln Asn Ala Leu Leu Val Arg Tyr Thr Lys
        400                 405                 410 aaa gta ccc caa gtg tca act cca act ctt gta gag gtc tca aga aac      1398
Lys Val Pro Gln Val Ser Thr Pro Thr Leu Val Glu Val Ser Arg Asn
    415                 420                 425 cta gga aaa gtg ggc agc aaa tgt tgt aaa cat cct gaa gca aaa aga      1446
Leu Gly Lys Val Gly Ser Lys Cys Cys Lys His Pro Glu Ala Lys Arg
430                 435                 440                 445 atg ccc tgt gca gaa gac tat cta tcc gtg gtc ctg aac cag tta tgt      1494
Met Pro Cys Ala Glu Asp Tyr Leu Ser Val Val Leu Asn Gln Leu Cys
                450                 455                 460 gtg ttg cat gag aaa acg cca gta agt gac aga gtc acc aaa tgc tgc      1542
Val Leu His Glu Lys Thr Pro Val Ser Asp Arg Val Thr Lys Cys Cys
            465                 470                 475 aca gaa tcc ttg gtg aac agg cga cca tgc ttt tca gct ctg gaa gtc      1590
Thr Glu Ser Leu Val Asn Arg Arg Pro Cys Phe Ser Ala Leu Glu Val
        480                 485                 490 gat gaa aca tac gtt ccc aaa gag ttt aat gct gaa aca ttc acc ttc      1638
Asp Glu Thr Tyr Val Pro Lys Glu Phe Asn Ala Glu Thr Phe Thr Phe
    495                 500                 505 cat gca gat ata tgc aca ctt tct gag aag gag aga caa atc aag aaa      1686
His Ala Asp Ile Cys Thr Leu Ser Glu Lys Glu Arg Gln Ile Lys Lys
510                 515                 520                 525 caa act gca ctt gtt gag ctc gtg aaa cac aag ccc aag gca aca aaa      1734
```

```
Gln Thr Ala Leu Val Glu Leu Val Lys His Lys Pro Lys Ala Thr Lys
                530                 535                 540 gag caa ctg aaa gct gtt atg gat gat ttc gca gct ttt gta gag aag       1782
Glu Gln Leu Lys Ala Val Met Asp Asp Phe Ala Ala Phe Val Glu Lys
                545                 550                 555 tgc tgc aag gct gac gat aag gag acc tgc ttt gcc gag gag ggt aaa       1830
Cys Cys Lys Ala Asp Asp Lys Glu Thr Cys Phe Ala Glu Glu Gly Lys
                560                 565                 570 aaa ctt gtt gct gca agt caa gct gcc tta ggc tta taacatctac            1876
Lys Leu Val Ala Ala Ser Gln Ala Ala Leu Gly Leu
                575                 580             585 atttaaaagc atctcagcct accatgagaa taagagaaag aaaatgaaga tcaaaagctt     1936
attcatctgt tttcttttc gttggtgtaa agccaacacc ctgtctaaaa aacataaatt      1996
tctttaatca ttttgcctct tttctctgtg cttcaattaa taaaaaatgg aaagaatcta    2056
atagagtggt acagcactgt tatttttcaa agatgtgttg ctatcctgaa aattctgtag    2116
gttctgtgga agttccagtg ttctctctta ttccacttcg gtagaggatt tctagtttct    2176
gtgggctaat taaataaatc actaatactc ttctaagtt                            2215

<210> SEQ ID NO 67
<211> LENGTH: 609
<212> TYPE: PRT
<213> ORGANISM: Homo sapiens

<400> SEQUENCE: 67

Met Lys Trp Val Thr Phe Ile Ser Leu Leu Phe Leu Phe Ser Ser Ala
                -20                 -15                 -10

Tyr Ser Arg Gly Val Phe Arg Arg Asp Ala His Lys Ser Glu Val Ala
             -5                  -1  1                   5

His Arg Phe Lys Asp Leu Gly Glu Glu Asn Phe Lys Ala Leu Val Leu
         10                  15                  20

Ile Ala Phe Ala Gln Tyr Leu Gln Gln Cys Pro Phe Glu Asp His Val
 25                  30                  35                  40

Lys Leu Val Asn Glu Val Thr Glu Phe Ala Lys Thr Cys Val Ala Asp
                 45                  50                  55

Glu Ser Ala Glu Asn Cys Asp Lys Ser Leu His Thr Leu Phe Gly Asp
                 60                  65                  70

Lys Leu Cys Thr Val Ala Thr Leu Arg Glu Thr Tyr Gly Glu Met Ala
         75                  80                  85

Asp Cys Cys Ala Lys Gln Glu Pro Glu Arg Asn Glu Cys Phe Leu Gln
 90                  95                 100

His Lys Asp Asp Asn Pro Asn Leu Pro Arg Leu Val Arg Pro Glu Val
105                 110                 115                 120

Asp Val Met Cys Thr Ala Phe His Asp Asn Glu Glu Thr Phe Leu Lys
                125                 130                 135

Lys Tyr Leu Tyr Glu Ile Ala Arg Arg His Pro Tyr Phe Tyr Ala Pro
            140                 145                 150

Glu Leu Leu Phe Phe Ala Lys Arg Tyr Lys Ala Ala Phe Thr Glu Cys
            155                 160                 165

Cys Gln Ala Ala Asp Lys Ala Cys Leu Leu Pro Lys Leu Asp Glu
        170                 175                 180

Leu Arg Asp Glu Gly Lys Ala Ser Ser Ala Lys Gln Arg Leu Lys Cys
185                 190                 195                 200

Ala Ser Leu Gln Lys Phe Gly Glu Arg Ala Phe Lys Ala Trp Ala Val
            205                 210                 215
```

```
Ala Arg Leu Ser Gln Arg Phe Pro Lys Ala Glu Phe Ala Glu Val Ser
            220                 225                 230

Lys Leu Val Thr Asp Leu Thr Lys Val His Thr Glu Cys Cys His Gly
            235                 240                 245

Asp Leu Leu Glu Cys Ala Asp Asp Arg Ala Asp Leu Ala Lys Tyr Ile
            250                 255                 260

Cys Glu Asn Gln Asp Ser Ile Ser Ser Lys Leu Lys Glu Cys Cys Glu
265                 270                 275                 280

Lys Pro Leu Leu Glu Lys Ser His Cys Ile Ala Glu Val Glu Asn Asp
                285                 290                 295

Glu Met Pro Ala Asp Leu Pro Ser Leu Ala Ala Asp Phe Val Glu Ser
            300                 305                 310

Lys Asp Val Cys Lys Asn Tyr Ala Glu Ala Lys Asp Val Phe Leu Gly
            315                 320                 325

Met Phe Leu Tyr Glu Tyr Ala Arg Arg His Pro Asp Tyr Ser Val Val
            330                 335                 340

Leu Leu Leu Arg Leu Ala Lys Thr Tyr Glu Thr Thr Leu Glu Lys Cys
345                 350                 355                 360

Cys Ala Ala Ala Asp Pro His Glu Cys Tyr Ala Lys Val Phe Asp Glu
                365                 370                 375

Phe Lys Pro Leu Val Glu Glu Pro Gln Asn Leu Ile Lys Gln Asn Cys
            380                 385                 390

Glu Leu Phe Glu Gln Leu Gly Glu Tyr Lys Phe Gln Asn Ala Leu Leu
            395                 400                 405

Val Arg Tyr Thr Lys Lys Val Pro Gln Val Ser Thr Pro Thr Leu Val
            410                 415                 420

Glu Val Ser Arg Asn Leu Gly Lys Val Gly Ser Lys Cys Cys Lys His
425                 430                 435                 440

Pro Glu Ala Lys Arg Met Pro Cys Ala Glu Asp Tyr Leu Ser Val Val
                445                 450                 455

Leu Asn Gln Leu Cys Val Leu His Glu Lys Thr Pro Val Ser Asp Arg
            460                 465                 470

Val Thr Lys Cys Cys Thr Glu Ser Leu Val Asn Arg Arg Pro Cys Phe
            475                 480                 485

Ser Ala Leu Glu Val Asp Glu Thr Tyr Val Pro Lys Glu Phe Asn Ala
            490                 495                 500

Glu Thr Phe Thr Phe His Ala Asp Ile Cys Thr Leu Ser Glu Lys Glu
505                 510                 515                 520

Arg Gln Ile Lys Lys Gln Thr Ala Leu Val Glu Leu Val Lys His Lys
                525                 530                 535

Pro Lys Ala Thr Lys Glu Gln Leu Lys Ala Val Met Asp Asp Phe Ala
            540                 545                 550

Ala Phe Val Glu Lys Cys Cys Lys Ala Asp Asp Lys Glu Thr Cys Phe
            555                 560                 565

Ala Glu Glu Gly Lys Lys Leu Val Ala Ala Ser Gln Ala Ala Leu Gly
            570                 575                 580

Leu
585

<210> SEQ ID NO 68
<211> LENGTH: 1507
<212> TYPE: DNA
<213> ORGANISM: Homo sapiens
```

<400> SEQUENCE: 68

```
tctactagta ctcccagcta cactacctca atcaccacca ccgagacccc ctcacacagt    60
actcccagct acactacctc aatcaccacc accgagaccc catcacacag tactcccagc   120
ttcacttctt caatcaccac caccgagacc acatcccaca gtactcccag cttcacttct   180
tcaatcagga ccaccgagac acatcctac agtactccca gcttcacttc ttcaaatacc   240
atcactgaga ccacctcaca cagtactccc agctacatta cctcaatcac caccaccgag   300
accccctcaa gcagtactcc cagcttcagt tcttcgatca ccaccactga ccacatcc    360
cacagtactc ccggcttcac ttcttcaatc accaccactg agactacatc ccacagtact   420
cccagcttca cttcttcgat caccaccact gagaccacct cacatgatac tcccagcttc   480
acttcttcaa tcaccaccag tgagaccccc tcacacagta ctcccagctc cacttcttta   540
atcaccacca ccaagaccac ctcacacagt actcccagct cacttcttc gatcaccacc   600
accgagacca cctcacacag tgctcgcagc ttcacttctt cgatcaccac caccgagacc   660
acctcacaca atactcggag cttcacttct tcgatcacca ccaccgagac caactctcac   720
agtactacca gcttcacttc ttcgatcacc accaccgaga ccacctcaca cagtactccc   780
agcttcagtt cttcaatcac caccactgag accccttac acagtactcc tggcctacct   840
tcgtgggtca ccaccaccaa gaccacctca cacattactc ctggcctcac ttcttcaatc   900
accaccactg agactacctc acacagtact cccggcttca cttcttcaat caccaccact   960
gagaccacct cagagagtac tcccagcctc agttcttcaa ccatctactc cacagtcagc  1020
acatccacaa ctgccatcac ctcacatttt actacctcag agactgcggt gactcccaca  1080
cctgtaaccc catcttctct gagtacagac atcccgacca caagcctacg aactctcacc  1140
ccttcgtctg tgggcaccag cacttcattg actacaacca cagactttcc ctctataccc  1200
actgatatca gtaccttacc aactcgaaca cacatcattt catcttctcc ctccatccaa  1260
agtacagaaa cctcatccct tgtgggcacc acctctccca ccatgtccac tgtgagaatg  1320
accctcagaa ttactgagaa cacccccaatc agttcctta gcacaagtat tgttgttata  1380
cctgaaaccc caacacagac ccctcctgta ctgacgtcag ccactgggac ccaaacatct  1440
cctgcaccta ctactgtcac ctttggaagt acggattcct ccacgtccac tcttcataag  1500
cttctct                                                            1507
```

<210> SEQ ID NO 69
<211> LENGTH: 502
<212> TYPE: PRT
<213> ORGANISM: Homo sapiens

<400> SEQUENCE: 69

```
Ser Thr Ser Thr Pro Ser Tyr Thr Thr Ser Ile Thr Thr Thr Glu Thr
1               5                   10                  15

Pro Ser His Ser Thr Pro Ser Tyr Thr Thr Ser Ile Thr Thr Thr Glu
            20                  25                  30

Thr Pro Ser His Ser Thr Pro Ser Phe Thr Ser Ser Ile Thr Thr Thr
        35                  40                  45

Glu Thr Thr Ser His Ser Thr Pro Ser Phe Thr Ser Ser Ile Arg Thr
    50                  55                  60

Thr Glu Thr Thr Ser Tyr Ser Thr Pro Ser Phe Thr Ser Ser Asn Thr
65                  70                  75                  80

Ile Thr Glu Thr Thr Ser His Ser Thr Pro Ser Tyr Ile Thr Ser Ile
                85                  90                  95
```

```
Thr Thr Thr Glu Thr Pro Ser Ser Thr Pro Ser Phe Ser Ser
            100                 105             110

Ile Thr Thr Thr Glu Thr Thr Ser His Ser Thr Pro Gly Phe Thr Ser
            115                 120                 125

Ser Ile Thr Thr Thr Glu Thr Thr Ser His Ser Thr Pro Ser Phe Thr
130                 135                 140

Ser Ser Ile Thr Thr Thr Glu Thr Thr Ser His Asp Thr Pro Ser Phe
145                 150                 155                 160

Thr Ser Ser Ile Thr Thr Ser Glu Pro Ser His Ser Thr Pro Ser
            165                 170                 175

Ser Thr Ser Leu Ile Thr Thr Thr Lys Thr Thr Ser His Ser Thr Pro
            180                 185                 190

Ser Phe Thr Ser Ser Ile Thr Thr Thr Glu Thr Thr Ser His Ser Ala
            195                 200                 205

Arg Ser Phe Thr Ser Ser Ile Thr Thr Thr Glu Thr Thr Ser His Asn
            210                 215                 220

Thr Arg Ser Phe Thr Ser Ser Ile Thr Thr Thr Glu Thr Asn Ser His
225                 230                 235                 240

Ser Thr Thr Ser Phe Thr Ser Ser Ile Thr Thr Thr Glu Thr Thr Ser
            245                 250                 255

His Ser Thr Pro Ser Phe Ser Ser Ile Thr Thr Thr Glu Thr Pro
            260                 265                 270

Leu His Ser Thr Pro Gly Leu Pro Ser Trp Val Thr Thr Lys Thr
            275                 280                 285

Thr Ser His Ile Thr Pro Gly Leu Thr Ser Ser Ile Thr Thr Thr Glu
290                 295                 300

Thr Thr Ser His Ser Thr Pro Gly Phe Thr Ser Ser Ile Thr Thr Thr
305                 310                 315                 320

Glu Thr Thr Ser Glu Ser Thr Pro Ser Leu Ser Ser Thr Ile Tyr
            325                 330                 335

Ser Thr Val Ser Thr Ser Thr Ala Ile Thr Ser His Phe Thr Thr
            340                 345                 350

Ser Glu Thr Ala Val Thr Pro Thr Pro Val Thr Pro Ser Ser Leu Ser
            355                 360                 365

Thr Asp Ile Pro Thr Thr Ser Leu Arg Thr Leu Thr Pro Ser Ser Val
370                 375                 380

Gly Thr Ser Thr Ser Leu Thr Thr Thr Asp Phe Pro Ser Ile Pro
385                 390                 395                 400

Thr Asp Ile Ser Thr Leu Pro Thr Arg Thr His Ile Ile Ser Ser Ser
            405                 410                 415

Pro Ser Ile Gln Ser Thr Glu Thr Ser Ser Leu Val Gly Thr Thr Ser
            420                 425                 430

Pro Thr Met Ser Thr Val Arg Met Thr Leu Arg Ile Thr Glu Asn Thr
            435                 440                 445

Pro Ile Ser Ser Phe Ser Thr Ser Ile Val Val Ile Pro Glu Thr Pro
            450                 455                 460

Thr Gln Thr Pro Pro Val Leu Thr Ser Ala Thr Gly Thr Gln Thr Ser
465                 470                 475                 480

Pro Ala Pro Thr Thr Val Thr Phe Gly Ser Thr Asp Ser Ser Thr Ser
            485                 490                 495

Thr Leu His Lys Leu Leu
            500
```

<210> SEQ ID NO 70
<211> LENGTH: 738
<212> TYPE: DNA
<213> ORGANISM: Homo sapiens

<400> SEQUENCE: 70

```
actagtacag gttctggtca tgcaagctct accccaggtg gagaaaagga gacttcggct    60
acccagagaa gttcagtgcc cagctctact gagaagaatg ctgtgagtat gaccagcagc   120
gtactctcca gccacagccc cggttcaggc tcctccacca ctcagggaca ggatgtcact   180
ctggccccgg ccacggaacc agcttcaggt tcagctgcca cctggggaca ggatgtcacc   240
tcggtcccag tcaccaggcc agccctgggc tccaccaccc cgccagccca cgatgtcacc   300
tcagccccgg acaacaagcc agcccgggc tccaccgccc cccagccca cggtgtcacc    360
tcggccccgg acaacaggcc cgccttggcg tccaccgccc ctccagtcca caatgtcacc   420
tcggcctcag gctctgcatc aggctcagct tctactctgg tgcacaacgg cacctctgcc   480
agggctacca caccccagc cagcaagagc actccattct caattcccag ccaccactct    540
gatactccta ccaccccttgc cagccatagc accaagactg atgccagtag cactcaccat   600
agcacggtac ctcctctcac ctcctccaat cacagcactt ctccccagtt gtctactggg   660
gtctctttct ttttcctgtc ttttcacatt tcaaacctcc agtttaattc ctctctggaa   720
gatcccagca ccgactac                                                  738
```

<210> SEQ ID NO 71
<211> LENGTH: 246
<212> TYPE: PRT
<213> ORGANISM: Homo sapiens

<400> SEQUENCE: 71

```
Thr Ser Thr Gly Ser Gly His Ala Ser Ser Thr Pro Gly Gly Glu Lys
 1               5                  10                  15

Glu Thr Ser Ala Thr Gln Arg Ser Ser Val Pro Ser Ser Thr Glu Lys
             20                  25                  30

Asn Ala Val Ser Met Thr Ser Ser Val Leu Ser Ser His Ser Pro Gly
         35                  40                  45

Ser Gly Ser Ser Thr Thr Gln Gly Gln Asp Val Thr Leu Ala Pro Ala
     50                  55                  60

Thr Glu Pro Ala Ser Gly Ser Ala Ala Thr Trp Gly Gln Asp Val Thr
 65                  70                  75                  80

Ser Val Pro Val Thr Arg Pro Ala Leu Gly Ser Thr Thr Pro Pro Ala
                 85                  90                  95

His Asp Val Thr Ser Ala Pro Asp Asn Lys Pro Ala Pro Gly Ser Thr
             100                 105                 110

Ala Pro Pro Ala His Gly Val Thr Ser Ala Pro Asp Asn Arg Pro Ala
         115                 120                 125

Leu Ala Ser Thr Ala Pro Pro Val His Asn Val Thr Ser Ala Ser Gly
     130                 135                 140

Ser Ala Ser Gly Ser Ala Ser Thr Leu Val His Asn Gly Thr Ser Ala
145                 150                 155                 160

Arg Ala Thr Thr Thr Pro Ala Ser Lys Ser Thr Pro Phe Ser Ile Pro
                165                 170                 175

Ser His His Ser Asp Thr Pro Thr Thr Leu Ala Ser His Ser Thr Lys
            180                 185                 190

Thr Asp Ala Ser Ser Thr His His Ser Thr Val Pro Pro Leu Thr Ser
```

195                 200                 205
Ser Asn His Ser Thr Ser Pro Gln Leu Ser Thr Gly Val Ser Phe Phe
        210                 215                 220

Phe Leu Ser Phe His Ile Ser Asn Leu Gln Phe Asn Ser Ser Leu Glu
225                 230                 235                 240

Asp Pro Ser Thr Asp Tyr
            245

<210> SEQ ID NO 72
<211> LENGTH: 1632
<212> TYPE: DNA
<213> ORGANISM: Saccharomyces sp.

<400> SEQUENCE: 72
agaacaaccg ctatcagctc attatccgaa gtaggaacta caaccgtggt atcatccagc    60
gccattgaac catcaagtgc ctctataatc tcacctgtca cctctacact ttcgagtaca   120
acatcgtcca atccaactac tacctcccta agttcgacat ctacatctcc aagctctaca   180
tctacatctc caagctctac atctacctca tcaagttcga catctacctc atcaagttcg   240
acatctacct catcaagttc gacatctaca tctccaagtt cgacatccac atcttcaagt   300
ttgacatcca catcttcaag ttctacatct acatcccaaa gttctacatc tacctcatca   360
agttcgacat ctacatctcc aagctctaca tctacctcat caagttcaac atctacatct   420
ccaagttcta aatctacttc tgcaagctcc acttccactt cttcatattc aacatctaca   480
tccccaagtt tgacttcttc atctccaact ttggcttcca cttctccaag ttcaacatct   540
attagctcta cttttactga ttcaacttca tcccttggct cctctatagc atcttcatca   600
acgtctgtgt cattatacag cccatccaca cctgtttact ccgtcccttc gacttcgtca   660
aatgttgcaa ctccttctat gacttcttca actgttgaaa caactgttag ttcacaaagt   720
tcgtctgaat atatcaccaa atcctcaatt tctactacta tcccatcatt ttccatgtct   780
acatatttca ccactgttag tggagtcact acaatgtata cgacatggtg tccttatagc   840
tctgaatctg agactagcac attaaccagt atgcatgaaa cggttacaac agacgctaca   900
gtctgcactc acgagtcttg catgccctcg cagacaacaa gtttgattac atcttctata   960
aaaatgtcca ctaaaaacgt cgcaacttct gtaagcacct caacggttga atcctcatat  1020
gcatgctcca catgtgctga acgtcacac tcgtattctt ccgtgcaaac agcttcatca  1080
agttctgtaa cacagcagac cacatccaca aagagttggg taagttcaat gacaacttcg  1140
gatgaagatt tcaataagca cgctaccggt aagtatcatg taacatcttc aggtacctca  1200
accatttcga ctagtgtaag tgaagccacg agtacatcaa gcattgactc agaatctcaa  1260
gaacaatcat cacacttatt atcgacatcg gtcctttcat cctcctcctt gtctgctaca  1320
ttatcctctg acagtactat tttgctattc agttctgtat catcactaag tgtcgaacag  1380
tcaccagtta ccacacttca aatttcttca acatcagaga ttttacaacc cacttcttcc  1440
acagctattg ctacaatatc tgcctctaca tcatcacttt ccgcaacatc tatctctaca  1500
ccatctacct ctgtggaatc gactattgaa tcttcatcat tgactccgac ggtatcttct  1560
attttcctct catcatcatc tgctccctct tctctacaaa catctgttac cactacagaa  1620
gtttccacta ct                                                      1632

<210> SEQ ID NO 73
<211> LENGTH: 544
<212> TYPE: PRT

<213> ORGANISM: Saccharomyces sp.

<400> SEQUENCE: 73

```
Arg Thr Thr Ala Ile Ser Ser Leu Ser Glu Val Gly Thr Thr Thr Val
1               5                   10                  15

Val Ser Ser Ser Ala Ile Glu Pro Ser Ser Ala Ser Ile Ile Ser Pro
            20                  25                  30

Val Thr Ser Thr Leu Ser Ser Thr Thr Ser Ser Asn Pro Thr Thr Thr
            35                  40                  45

Ser Leu Ser Ser Thr Ser Thr Ser Pro Ser Ser Thr Ser Thr Ser Pro
        50                  55                  60

Ser Ser Thr Ser Thr Ser Ser Ser Thr Thr Ser Ser Ser Ser Ser Ser
65                  70                  75                  80

Thr Ser Thr Ser Ser Ser Ser Ser Thr Ser Pro Ser Ser Thr Ser Ser
                85                  90                  95

Thr Ser Ser Ser Leu Thr Ser Thr Ser Ser Ser Thr Ser Thr Ser Ser
                100                 105                 110

Gln Ser Ser Thr Ser Thr Ser Ser Ser Thr Ser Thr Ser Pro Ser Ser
                115                 120                 125

Ser Thr Ser Thr Ser Ser Ser Thr Ser Thr Ser Pro Ser Ser Lys Ser
            130                 135                 140

Ser Thr Ser Ala Ser Ser Thr Ser Thr Ser Ser Tyr Ser Thr Ser Thr
145                 150                 155                 160

Ser Pro Ser Leu Thr Ser Ser Pro Thr Leu Ala Ser Thr Ser Pro Ser
                165                 170                 175

Ser Thr Ser Ile Ser Ser Thr Phe Thr Asp Ser Thr Ser Ser Leu Gly
                180                 185                 190

Ser Ser Ile Ala Ser Ser Ser Thr Ser Val Ser Leu Tyr Ser Pro Ser
            195                 200                 205

Thr Pro Val Tyr Ser Val Pro Ser Thr Ser Ser Asn Val Ala Thr Pro
    210                 215                 220

Ser Met Thr Ser Ser Thr Val Glu Thr Thr Val Ser Ser Gln Ser Ser
225                 230                 235                 240

Ser Glu Tyr Ile Thr Lys Ser Ser Ile Ser Thr Thr Ile Pro Ser Phe
                245                 250                 255

Ser Met Ser Thr Tyr Phe Ser Thr Val Ser Gly Val Thr Thr Met Tyr
            260                 265                 270

Thr Thr Trp Cys Pro Tyr Ser Ser Glu Ser Glu Thr Ser Thr Leu Thr
        275                 280                 285

Ser Met His Glu Thr Val Thr Thr Asp Ala Thr Val Cys Thr His Glu
    290                 295                 300

Ser Cys Met Pro Ser Gln Thr Thr Ser Leu Ile Thr Ser Ser Ile Lys
305                 310                 315                 320

Met Ser Thr Lys Asn Val Ala Thr Ser Val Ser Thr Ser Thr Val Glu
                325                 330                 335

Ser Ser Tyr Ala Cys Ser Thr Cys Ala Glu Thr Ser His Ser Tyr Ser
            340                 345                 350

Ser Val Gln Thr Ala Ser Ser Ser Val Thr Gln Gln Thr Thr Ser Thr
        355                 360                 365

Lys Ser Trp Val Ser Ser Met Thr Thr Ser Asp Glu Asp Phe Asn Lys
    370                 375                 380

His Ala Thr Gly Lys Tyr His Val Thr Ser Ser Gly Thr Ser
385                 390                 395                 400
```

```
Thr Ile Ser Thr Ser Val Ser Glu Ala Thr Ser Ser Ile Asp
            405                 410                 415

Ser Glu Ser Gln Glu Gln Ser Ser His Leu Leu Ser Thr Ser Val Leu
        420                 425                 430

Ser Ser Ser Ser Leu Ser Ala Thr Leu Ser Ser Asp Ser Thr Ile Leu
        435                 440                 445

Leu Phe Ser Ser Val Ser Ser Leu Ser Val Glu Gln Ser Pro Val Thr
    450                 455                 460

Thr Leu Gln Ile Ser Ser Thr Ser Glu Ile Leu Gln Pro Thr Ser Ser
465                 470                 475                 480

Thr Ala Ile Ala Thr Ile Ser Ala Ser Thr Ser Ser Leu Ser Ala Thr
                485                 490                 495

Ser Ile Ser Thr Pro Ser Thr Ser Val Glu Ser Thr Ile Glu Ser Ser
                500                 505                 510

Ser Leu Thr Pro Thr Val Ser Ser Ile Phe Leu Ser Ser Ser Ser Ala
        515                 520                 525

Pro Ser Ser Leu Gln Thr Ser Val Thr Thr Thr Glu Val Ser Thr Thr
    530                 535                 540
```

<210> SEQ ID NO 74
<211> LENGTH: 1629
<212> TYPE: DNA
<213> ORGANISM: Saccharomyces sp.

<400> SEQUENCE: 74

```
acaaccgcta tcagctcatt atccgaagta ggaactacaa ccgtggtatc atccagcgcc      60
attgaaccat caagtgcctc tataatctca cctgtcacct ctacactttc gagtacaaca     120
tcgtccaatc caactactac ctccctaagt tcgacatcta catctccaag ctctacatct     180
acatctccaa gctctacatc tacctcatca agttcgacat ctacctcatc aagttcgaca     240
tctacctcat caagttcgac atctacatct ccaagttcga catccacatc ttcaagtttg     300
acatccacat cttcaagttc tacatctaca tcccaaagtt ctacatctac ctcatcaagt     360
tcgacatcta catctccaag ctctacatct acctcatcaa gttcaacatc tacatctcca     420
agttctaaat ctacttctgc aagctccact tccacttctt catattcaac atctacatcc     480
ccaagtttga cttcttcatc tccaactttg gcttccactt ctccaagttc aacatctatt     540
agctctactt ttactgattc aacttcatcc cttggctcct ctatagcatc ttcatcaacg     600
tctgtgtcat tatacagccc atccacacct gtttactccg tcccttcgac ttcgtcaaat     660
gttgcaactc cttctatgac ttcttcaact gttgaaacaa ctgttagttc acaaagttcg     720
tctgaatata tcaccaaatc ctcaattttct actactatcc catcatttc catgtctaca     780
tatttcacca ctgttagtgg agtcactaca atgtatacga catggtgtcc ttatagctct     840
gaatctgaga ctagcacatt aaccagtatg catgaaacgg ttacaacaga cgctacagtc     900
tgcactcacg agtcttgcat gccctcgcag acaacaagtt tgattacatc ttctataaaa     960
atgtccacta aaaacgtcgc aacttctgta agcacctcaa cggttgaatc ctcatatgca    1020
tgctccacat gtgctgaaac gtcacactcg tattcttccg tgcaaacagc ttcatcaagt    1080
tctgtaacac agcagaccac atccacaaag agttgggtaa gttcaatgac aacttcggat    1140
gaagatttca ataagcacgc taccggtaag tatcatgtaa catcttcagg tacctcaacc    1200
atttcgacta gtgtaagtga agccacgagt acatcaagca ttgactcaga atctcaagaa    1260
caatcatcac acttattatc gacatcggtc ctttcatcct cctccttgtc tgctacatta    1320
```

-continued

```
tcctctgaca gtactatttt gctattcagt tctgtatcat cactaagtgt cgaacagtca    1380
ccagttacca cacttcaaat ttcttcaaca tcagagattt tacaacccac ttcttccaca    1440
gctattgcta caatatctgc ctctacatca tcactttccg caacatctat ctctacacca    1500
tctacctctg tggaatcgac tattgaatct tcatcattga ctccgacggt atctttctatt   1560 ttcctctcat catcatctgc tccctcttct ctacaaacat ctgttaccac tacagaagtt   1620
tccactact                                                            1629
```

<210> SEQ ID NO 75
<211> LENGTH: 543
<212> TYPE: PRT
<213> ORGANISM: Saccharomyces sp.

<400> SEQUENCE: 75

```
Thr Thr Ala Ile Ser Ser Leu Ser Glu Val Gly Thr Thr Thr Val Val
1               5                   10                  15

Ser Ser Ser Ala Ile Glu Pro Ser Ser Ala Ser Ile Ile Ser Pro Val
            20                  25                  30

Thr Ser Thr Leu Ser Ser Thr Thr Ser Ser Asn Pro Thr Thr Thr Ser
        35                  40                  45

Leu Ser Ser Thr Ser Thr Ser Pro Ser Ser Thr Ser Thr Ser Pro Ser
50                  55                  60

Ser Thr Ser Thr Ser Ser Ser Thr Ser Thr Ser Ser Ser Ser Ser Thr
65                  70                  75                  80

Ser Thr Ser Ser Ser Ser Thr Ser Thr Ser Pro Ser Ser Thr Ser Thr
                85                  90                  95

Ser Ser Ser Leu Thr Ser Thr Ser Ser Ser Thr Ser Thr Ser Thr Gln
            100                 105                 110

Ser Ser Thr Ser Thr Ser Ser Ser Thr Ser Thr Ser Pro Ser Ser
            115                 120                 125

Thr Ser Thr Ser Ser Ser Ser Thr Ser Thr Ser Pro Ser Ser Lys Ser
        130                 135                 140

Thr Ser Ala Ser Ser Thr Ser Thr Ser Ser Tyr Ser Thr Ser Thr Ser
145                 150                 155                 160

Pro Ser Leu Thr Ser Ser Ser Pro Thr Leu Ala Ser Thr Ser Pro Ser
                165                 170                 175

Ser Thr Ser Ile Ser Ser Thr Phe Thr Asp Ser Thr Ser Ser Leu Gly
            180                 185                 190

Ser Ser Ile Ala Ser Ser Ser Thr Ser Val Ser Leu Tyr Ser Pro Ser
        195                 200                 205

Thr Pro Val Tyr Ser Val Pro Ser Thr Ser Ser Asn Val Ala Thr Pro
    210                 215                 220

Ser Met Thr Ser Ser Thr Val Glu Thr Thr Val Ser Ser Gln Ser Ser
225                 230                 235                 240

Ser Glu Tyr Ile Thr Lys Ser Ser Ile Ser Thr Thr Ile Pro Ser Phe
                245                 250                 255

Ser Met Ser Thr Tyr Phe Thr Thr Val Ser Gly Val Thr Thr Met Tyr
            260                 265                 270

Thr Thr Trp Cys Pro Tyr Ser Ser Glu Ser Glu Thr Ser Thr Leu Thr
        275                 280                 285

Ser Met His Glu Thr Val Thr Thr Asp Ala Thr Val Cys Thr His Glu
    290                 295                 300

Ser Cys Met Pro Ser Gln Thr Thr Ser Leu Ile Thr Ser Ser Ile Lys
305                 310                 315                 320
```

Met Ser Thr Lys Asn Val Ala Thr Ser Val Ser Ser Thr Val Glu
              325                 330                 335

Ser Ser Tyr Ala Cys Ser Thr Cys Ala Glu Thr Ser His Ser Tyr Ser
          340                 345                 350

Ser Val Gln Thr Ala Ser Ser Ser Val Thr Gln Gln Thr Thr Ser
          355                 360                 365

Thr Lys Ser Trp Val Ser Ser Met Thr Thr Ser Asp Glu Asp Phe Asn
    370                 375                 380

Lys His Ala Thr Gly Lys Tyr His Val Thr Ser Ser Gly Thr Ser Thr
385                 390                 395                 400

Ile Ser Thr Ser Val Ser Glu Ala Thr Ser Thr Ser Ser Ile Asp Ser
              405                 410                 415

Glu Ser Gln Glu Gln Ser Ser His Leu Leu Ser Thr Ser Val Leu Ser
              420                 425                 430

Ser Ser Ser Leu Ser Ala Thr Leu Ser Ser Asp Ser Thr Ile Leu Leu
          435                 440                 445

Phe Ser Ser Val Ser Ser Leu Ser Val Glu Gln Ser Pro Val Thr Thr
    450                 455                 460

Leu Gln Ile Ser Ser Thr Ser Glu Ile Leu Gln Pro Thr Ser Ser Thr
465                 470                 475                 480

Ala Ile Ala Thr Ile Ser Ala Ser Thr Ser Ser Leu Ser Ala Thr Ser
              485                 490                 495

Ile Ser Thr Pro Ser Thr Ser Val Glu Ser Thr Ile Glu Ser Ser Ser
              500                 505                 510

Leu Thr Pro Thr Val Ser Ser Ile Phe Leu Ser Ser Ser Ser Ala Pro
    515                 520                 525

Ser Ser Leu Gln Thr Ser Val Thr Thr Thr Glu Val Ser Thr Thr
          530                 535                 540

<210> SEQ ID NO 76
<211> LENGTH: 1506
<212> TYPE: DNA
<213> ORGANISM: Artificial Sequence
<220> FEATURE:
<223> OTHER INFORMATION: Modified human MUC3 gene

<400> SEQUENCE: 76
tctactagta caccaagcta tactacatca attactagca ctgagacacc atctcattca    60
actccttcta gttcgacttc aattacaact acagagacac ccagtcacag caccccatct   120
tacactagct ctgtctccac atccgagact acatcacatt ctactccatc agaaacaagc   180
tccagtagaa caacagaaag cacctcttat agttcaccta gctccacttc atctaacaca   240
attactgaga caagctcaca ctccactcct agtactgcta cttctatttc ctcgaccgaa   300
acacctagtt caagtacacc atctgtatca tcgtccatta ctgttactga gagttcatct   360
catagcactc tggagctac ttccactttg acatcgagtg aaacttctac ttggtcaaca   420
ccatctagca caagttctat tatgtcaagc tcctacactt cagctgacac tccatctgaa   480
acatcagttt atacttccag cgaaaacccca tcgtcctcaa gcccaactag cacatctttg   540
atttctagtt cgaagtcaac atcgaccagt acaccttcgt ttacttcttc gattactagc   600
actgagacct cctcatattc tgctagttcc tatacacctt cagttagtag cacagcaagt   660
tctagcaaga acacaacgag ttccactgct tctataagca gtacagagac tgttagttca   720
tcgactagct ctgtctctag tactattcct tcttctcaat ccacaagtta ttctacacca   780

```
tcattctcca gttcggcaac aagcagtgtt actccattgc attcaacacc atctctacca      840
tcttgggtta ctacaagtaa gaccacatca catattacac caggtctgac ttcgtccatg      900
tcttcgagcg agacctatag ccatagtact ccaggtttta caagctctat tacttcgaca      960
gaatcgacaa gtgagtcaac tccatcattg tccagttcta caatttatag tactgtttca     1020
acatctacta cagctattac ttcacatttt acaacttctg agacagctgt tactccaaca     1080
ccagttacac cctctagctt gagtacagat atcccaacta caagtttgag aactttgact     1140
ccttcctctg ttggtacctc gacttccttg acaactacaa ctgactttcc atcaattcca     1200
acagacatta gcactttgcc aacaagaact catattattt caagctcacc atctattcaa     1260
tcaacagaga ctagcagttt ggttggtact acatctccaa ctatgtcaac agttagaatg     1320
actttgagaa ttacagagaa cactccaatt tcttcattca gtacttccat tgttgttatt     1380
ccagagacac caactcaaac accaccagtt ttgacttctg ctacaggtac tcaaacatca     1440
ccagctccaa ctacagttac ttttggttct actgactcat ctacatcaac tttgcataag     1500
cttttg                                                                1506
```

<210> SEQ ID NO 77
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 77

Cys Xaa Xaa Xaa Arg Gly Asp Xaa Xaa Xaa Cys
1               5                   10

<210> SEQ ID NO 78
<211> LENGTH: 19
<212> TYPE: DNA
<213> ORGANISM: Artificial Sequence
<220> FEATURE:
<223> OTHER INFORMATION: Synthetic

<400> SEQUENCE: 78
aggagagctg aatagttgg                                                    19

<210> SEQ ID NO 79
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(31)
<223> OTHER INFORMATION: n is a, c, g, or t
<220> FEATURE:
<221> NAME/KEY: misc_feature
<222> LOCATION: (41)..(49)
<223> OTHER INFORMATION: n is a, c, g, or t

<400> SEQUENCE: 79
ccaactattc agctctcctt gtnnnnnnnn nagaggagac nnnnnnnnnt gtcatgggaa        60

```
ggacctgctg tttaag                                                        76

<210> SEQ ID NO 80
<211> LENGTH: 22
<212> TYPE: DNA
<213> ORGANISM: Artificial Sequence
<220> FEATURE:
<223> OTHER INFORMATION: Synthetic

<400> SEQUENCE: 80
cctcctacct tgattgcatc ag                                                 22

<210> SEQ ID NO 81
<211> LENGTH: 24
<212> TYPE: DNA
<213> ORGANISM: Artificial Sequence
<220> FEATURE:
<223> OTHER INFORMATION: Synthetic

<400> SEQUENCE: 81
ggagatgaag aagtcaaact tggg                                               24

<210> SEQ ID NO 82
<211> LENGTH: 22
<212> TYPE: DNA
<213> ORGANISM: Artificial Sequence
<220> FEATURE:
<223> OTHER INFORMATION: Synthetic

<400> SEQUENCE: 82
gaggcacttg atggttcaat gg                                                 22

<210> SEQ ID NO 83
<211> LENGTH: 11
<212> TYPE: PRT
<213> ORGANISM: Artificial Sequence
<220> FEATURE:
<223> OTHER INFORMATION: Synthetic

<400> SEQUENCE: 83

Cys Asn Ser Pro Arg Gly Asp Thr Pro Ile Cys
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

Cys Ile Ile Pro Arg Gly Asp Arg Pro Arg Cys
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic

<400> SEQUENCE: 85

Cys Gln Gly Ser Arg Gly Asp Thr Pro Asn Cys
1               5                   10

<210> SEQ ID NO 86
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 86

Cys Gly Phe His Arg Gly Asp Thr Pro Asp Cys
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic

<400> SEQUENCE: 87

Cys Arg Gln His Arg Gly Asp Thr Pro Ala Cys
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic

<400> SEQUENCE: 88

Cys Tyr Pro Ser Arg Gly Asp Phe Ala His Cys
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic

<400> SEQUENCE: 89

Cys Asn Ser Arg Arg Gly Asp Val Pro Ile Cys
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthetic

<400> SEQUENCE: 90

Cys His Pro Ile Arg Gly Asp Thr Tyr Tyr Cys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic

<400> SEQUENCE: 91

Cys Arg Ile Ala Arg Gly Asp Phe Pro Asp Asp Cys
1               5                   10

<210> SEQ ID NO 92
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 92

Cys Arg Ile Pro Arg Gly Asp Met Pro Asp Asp Cys
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic

<400> SEQUENCE: 93

Cys Val Thr Gly Arg Gly Asp Ser Pro Ala Cys
1               5                   10

<210> SEQ ID NO 94
<211> LENGTH: 86
<212> TYPE: DNA
<213> ORGANISM: Homo sapiens

<400> SEQUENCE: 94
actaagcttg acctggctcc acaaattgct ggctataccg acgccgcgca tccgggtaga      60
tccgtggtcc cagctttgct tcctct                                          86

<210> SEQ ID NO 95
<211> LENGTH: 78
<212> TYPE: DNA
<213> ORGANISM: Homo sapiens

<400> SEQUENCE: 95
ttatctagat tattatggag cagtggcagt ttccaacagt aacagagtac cggccagcag      60
aggaagcaaa gctgggac                                                   78

<210> SEQ ID NO 96
<211> LENGTH: 28
<212> TYPE: DNA
<213> ORGANISM: Artificial Sequence
<220> FEATURE:
<223> OTHER INFORMATION: Synthetic

<400> SEQUENCE: 96
caccatgagg ctcgccgtgg gagccctg                                        28

<210> SEQ ID NO 97
<211> LENGTH: 24
<212> TYPE: DNA
<213> ORGANISM: Artificial Sequence
<220> FEATURE:
<223> OTHER INFORMATION: Synthetic

<400> SEQUENCE: 97
ttattatgga gcagtggcag tttc                                            24

<210> SEQ ID NO 98
<211> LENGTH: 41
<212> TYPE: PRT
<213> ORGANISM: Homo sapiens

<400> SEQUENCE: 98
```

-continued

```
Asp Gln Leu Gly Gly Ser Cys Arg Thr His Tyr Gly Tyr Ser Ser Gly
1               5                   10                  15

Ala Ser Ser Leu His Arg His Trp Gly Leu Leu Leu Ala Ser Leu Ala
            20              25                  30

Pro Leu Val Leu Cys Leu Ser Leu Leu
            35              40
```

TRANSFERRIN FUSION PROTEIN LIBRARIES

RELATED APPLICATIONS

This application is related to PCT International Application PCT/US2006/023742, filed Jun. 19, 2006, which claims the benefit of U.S. Provisional Application 60/691,229, filed Jun. 17, 2005. This application is also related to U.S. patent application Ser. No. 10/515,429, filed Nov. 23, 2004; U.S. Provisional Application 60/485,404, filed Jul. 9, 2003; U.S. patent application Ser. No. 10/384,060 filed Mar. 10, 2003; and U.S. Provisional Application 60/406,977, filed Aug. 30, 2002, all of which are incorporated by reference in their entirety.

REFERENCE TO SEQUENCE LISTING

This application is being filed electronically via EFS-Web and includes an electronically submitted sequence listing in .txt format. The .txt file contains a sequence listing entitled "PC19610A_SequenceListing_ST25.txt" created on Feb. 12, 2014, and having a size of 87 KB. The sequence listing contained in this .txt file is part of the specification and is herein incorporated by reference in its entirety.

FIELD OF THE INVENTION

The present invention relates to fusion proteins, fusion protein libraries, and the use of fusion proteins to screen for binding activity of a ligand, for instance, an integrin binding peptide.

BACKGROUND OF THE INVENTION

Cell Surface Display Systems

Combinatorial library screening and selection methods have become common research tools (Phizicky et al., (1995) Microbiological Reviews 59: 94-123). One of the most widespread techniques is phage display, whereby a protein is expressed as a polypeptide fusion to a bacteriophage coat protein and subsequently screened by binding to an immobilized or soluble biotinylated ligand. Presentation of random peptides is often accomplished by constructing chimeric proteins expressed on the outer surface of filamentous bacteriophages such as M13, fd and f1. Phage display has been successfully applied to antibodies, DNA binding proteins, protease inhibitors, and enzymes. See Hoogenboom et al. (1997) Trends in Biotechnol. 15: 62-70; Ladner (1995) Trends in Biotechnol. 13: 426-430; Lowman et al. (1991) Biochemistry 30: 10832-10838; Markland et al. (1996) Biochemistry 35: 8045-8057; and Matthews et al. (1993) Nucleic Acids Res. 21: 1727-1734.

In addition to phage display, several bacterial cell surface display methods have been developed. See Georgiou et al. (1997) Nat. Biotechnol. 15: 29-34. One approach taken in bacterial cell surface display methods has been to use a fusion protein comprising a pilin protein (TraA) or a portion thereof and a heterologous polypeptide displaying the library peptide on the outer surface of a bacterial host cell capable of forming pilus. See U.S. Pat. No. 5,516,637 which is herein incorporated by reference in its entirety.

The FLITRX™ random peptide library (Invitrogen™ Life Technologies) uses the bacterial flagellar protein, FliC, and thioredoxin, TrxA, to display a random peptide library of dodecamers on the surface of *E. coli* in a conformationally constrained manner. See Lu et al. (1995) BioTechnology 13: 366. These systems have been applied to antibody epitope mapping, the development and construction of live bacterial vaccine delivery systems, and the generation of whole-cell bio-adsorbants for environmental clean-up purposes and diagnostics. Peptide sequences that bind to tumor specific targets on tumor derived epithelial cells have also been identified using the FLITRX™ system. See Brown at al. (2000) Annals of Surgical Oncology, 7(10): 743.

Yeast cell surface display systems have been developed for library screening and have been successful at overcoming some of the limitations of phage and bacterial display systems. Yeast surface display systems, such as the pYD1 Yeast Display Vector Kit (Invitrogen™ Life Technologies), use the a-agglutinin receptor of *S. cerevisiae* to display foreign proteins on the cell surface. The a-agglutinin receptor consists of two subunits encoded by the AGA1 and AGA2 genes. The Aga1 protein (Aga1p, 725 amino acids) is secreted from the cell and becomes covalently attached to β-glucan in the extracellular matrix of the yeast cell wall. The Aga2 protein (Aga2p, 69 amino acids) binds to Aga1p through two disulfide bonds and after secretion remains attached to the cell through its contact with Aga1p. The N-terminal portion of Aga2p is required for attachment to Aga1p, while proteins and peptides can be fused to the C-terminus for presentation on the yeast cell surface. Agglutinin is a native yeast protein which normally functions as a specific adhesion contact to fuse yeast cells during mating. As such, it has evolved for protein-protein binding without excessive steric hindrance from cell wall components. Boder et al. in "Yeast Surface Display for Directed Evolution of Protein Expression, Affinity, and Stability", Applications of Chimeric Genes and Hybrid Proteins, (Jeremy Thorner et al.), Academic Press, 2000, Vol. 328, pages 430-439; U.S. Pat. No. 6,699,658; and U.S. Pat. No. 6,423,538, which are herein incorporated by reference in their entireties.

One of the drawbacks of this system, however, is that, since the Aga2p-fusion protein and Aga1p are required to form a disulfide bond in order for the Aga2p protein to be tethered to the cell wall, the efficiency of display is relatively low, with only 40% to 60% of yeast cells effectively displaying the protein on the surface. See Feldhause et al. (2003) Nat. Biotechnol. 21(2): 163-70. A need exists for a yeast display system that that presents most, if not all, proteins of a library on a cell surface.

Another drawback of the Aga1p and Aga2p yeast display system is that it requires that the ligand to be screened be attached to the C-terminus of Aga2p. As a result, the system cannot be used to select peptides in which a free N-terminus is require for binding and/or is required for activity. Accordingly, a need exists for a flexible display system that does not require the binding of the N-terminus of the ligand to a yeast cell protein.

Transferrin Fusion Protein

Serum transferrin (Tf) is a monomeric glycoprotein with a molecular weight of 80,000 daltons that binds iron in the circulation and transports it to various tissues via the transferrin receptor (TfR) (Aisen et al. (1980) Ann. Rev. Biochem. 49: 357-393; MacGillivray et al. (1981) J. Biol. Chem. 258: 3543-3553; and U.S. Pat. No. 5,026,651). Tf is one of the most common serum molecules, comprising up to about 5-10% of total serum proteins. Carbohydrate deficient transferrin occurs in elevated levels in the blood of alcoholic individuals and exhibits a longer half life (approximately 14-17 days) than that of glycosylated transferrin (approximately 7-10 days). See van Eijk et al. (1983) Clin. Chim. Acta 132:167-171; Stibler (1991) Clin. Chem. 37:2029-2037;

Arndt (2001) Clin. Chem. 47(1):13-27; and Stibler et al. in "Carbohydrate-deficient consumption", Advances in the Biosciences, (Ed Nordmann et al.), Pergamon, 1988, Vol. 71, pages 353-357). The structure of Tf has been well characterized and the mechanisms of receptor binding, iron binding and release and carbonate ion binding have been elucidated. See U.S. Pat. Nos. 5,026,651, 5,986,067 and MacGillivray et al. (1983) J. Biol. Chem. 258(6):3543-3546, all of which are herein incorporated by reference in their entirety.

Mucins are a family of heavily glycosylated proteins. Mucins and mucin-like proteins have been used to elevate a ligand domain of a fusion protein at a substantial distance from a microarray. It has been hypothesized that elevating a ligand a significant distance from a substrate increases binding of the ligand to a receptor displayed in receptor-expressing cells. See WO 01/46698 which is herein incorporated by reference in its entirety.

The inventors of the present invention have previously developed transferrin fusion protein libraries. See U.S. patent application Ser. No. 10/515,429 which is herein incorporated by reference in its entirety. The present invention provides a transferrin fusion protein that contains a stalk-like moiety, such as a mucin or a mucin-like protein, designed to reduce steric hindrance and increase ligand binding. The fusion protein can be expressed and displayed on the surface of a host cell, such as yeast, such that the expressed transferrin fusion protein can be used as a peptide screening platform. Further, the transferrin and ligand portion of the fusion protein can be cleaved and used as a therapeutic. This may not be possible to accomplish with existing yeast display technology since the removal of the N-terminal fused Aga2 protein would likely affect the conformation of a small ligand linked to transferrin.

SUMMARY OF THE INVENTION

As described in more detail below, the present invention includes a fusion protein with a transferrin (Tf) moiety. In one embodiment of the invention, the fusion protein comprises a transferrin moiety, a stalk moiety, and a cell wall linking group. In this embodiment of the invention, the fusion protein is expressed on a cell surface of the cell and linked to the cell wall by the cell wall linking group. In another embodiment of the invention, the fusion protein comprises a transferrin moiety which is linked to a cell membrane via an anchor, for instance, a GPI anchor.

The transferrin moiety of the claimed invention contains a transferrin protein or a portion thereof. For example, the transferrin moiety can be a portion of the N domain, i.e. lobe, of the transferrin protein. The Tf moiety can be a modified Tf protein such that the Tf portion of the fusion protein exhibits reduced glycosylation compared to wild-type Tf. In one embodiment of the invention, the transferrin portion of the fusion protein exhibits no glycosylation. In another embodiment of the present invention, the transferrin moiety of the fusion protein is modified so that it exhibits reduced affinity to iron, bicarbonate and/or reduced affinity to a transferrin receptor compared to wild-type transferrin. The transferrin moiety may be modified so that it is unable to bind to a transferrin receptor, to iron or to bicarbonate. Accordingly, the present invention includes modified transferrin moieties in which the transferrin moiety is modified at one or more sites from the group consisting of a glycosylation site, iron binding site, hinge site, bicarbonate site, and receptor binding site.

The ligand of the claimed invention can be complexed or fused with the transferrin moiety in various ways. Further, a transferrin moiety may have more than one ligand associated with it. The ligand moiety may be fused to the N-terminus, to the C-terminus of the transferrin moiety, or may be located within the transferrin moiety. In one embodiment of the invention, the ligand is inserted at one or more amino acid positions of the N-lobe ($N_1$ or $N_2$) selected from the group consisting of amino acid positions Asp33, Asn55, Asn75, Asp90, Gly257, Lys280, His289, Ser298, Ser105, Glu141, Asp166, Gln184, Asp197, Lys217, Thr231 and Cys241.

The invention also includes a ligand which is located on an exposed loop of the transferrin moiety. The fusion protein can be constructed so that the ligand moiety is in-frame with the transferrin moiety, for instance, by expressing in a host cell a vector coding for the transferrin fusion protein and ligand.

In another embodiment, the ligand moiety may comprise one or more randomized surface exposed amino acid residues within the transferrin moiety. For instance, the transferrin moiety may contain at least about 3, about 4, about 5, about 6, about 7, about 8, about 9 or about 10 or more randomized surface exposed amino acid residues. In one embodiment, a library of transferrin fusion proteins or transferrin proteins is constructed using about six surface exposed amino acid residues. Surface exposed amino acids of transferrin can be randomized using mutagenesis methods known in the art. The randomized amino acid residues may be sequential or clustered in an exposed region. Surface exposed regions of transferrin include, but are not limited to the amino acids at about position 85 to about position 92, about position 276 to about position 298 or about position 207 to about 217.

The ligand can take many forms, including, but not limited to, a single chain antibody, antibody, antibody fragment, antibody variable region, random peptide, or antibody complimentarity-determining region (CDR). Ligands may contain a variable or random region and an unvariable region. In one embodiment, the ligand is a random peptide. A random peptide ligand moiety expressed with a transferrin moiety can be created by many methods known in the art including, but not limited to, error prone PCR and DNA shuffling. A ligand moiety can also be added to a transferrin fusion protein after the latter has already been translated.

The ligand can be a ligand of interest or one ligand in a library of ligands. The ligand may be capable of binding to one or more receptors or agents such as a peptide, antigen, receptor, antibody, toxin, metabolite, and nucleic acid.

In one embodiment of the invention, the ligand is a known ligand binding sequence containing one or more randomized amino acids within the ligand binding sequence or in close proximity to the ligand binding sequence. For instance, the ligand can be the integrin binding sequence Arg-Gly-Asp (RGD) with one or more randomized amino acid residues flanking either side or both sides of the RGD sequence. In one embodiment of the invention, the ligand is CXXXRGDXXXC, where X is a randomized amino acid residue. In a further embodiment of the invention, the ligand is XXXRGDXXX.

As previously discussed, in one embodiment, the fusion protein comprises a stalk moiety. The stalk moiety can be oriented such that its N-terminus is fused to the transferrin moiety and its C-terminus located in the cell, for instance, in the cell wall. In one embodiment, the C-terminus of the stalk moiety is fused to an anchor moiety. In one embodiment, the stalk moiety of the present invention spans the cell wall of a yeast cell and is generally a moderately to heavily glycosylated peptide. By spanning the cell wall, the stalk moiety may act as a cell wall linking member to tether the fusion protein through the cell wall. In another embodiment of the invention, the stalk moiety spans the cell wall and is partially displayed on the cell surface. The composition of the stalk moiety may give it a rod-like conformation which reduces steric hindrance that would otherwise exist between the fusion protein, notably the ligand, and the host cell.

The stalk moiety may contain or consist of a mucin, mucin variant or fragment thereof. The mucin domain may include, for instance, MUC1, MUC2, MUC3, MUC4, MUC5AC, MUC5B, MUC6, MUC7, MUC8, MUC9, MUC10, MUC11, MUC12, MUC13, MUC14, MUC15, MUC16, MUC17, MUC18, MUC19, MUC20, MUC21 and variants thereof. In one embodiment, the stalk moiety contains a human MUC1 domain such as the peptide corresponding to the nucleic acid sequence of SEQ ID NO: 5 or a fragment thereof. In another embodiment, the stalk moiety comprises two or more repeats of a mucin, for instance, two or more repeats of MUC1 or MUC3. In a further embodiment, the stalk moiety comprises two or more mucin proteins or variants or fragments thereof from the group consisting of MUC1, MUC2, MUC3, MUC4, MUC5AC, MUC5B, MUC6, MUC7, MUC8, MUC9, MUC10, MUC11, MUC12, MUC13, MUC14, MUC15, MUC16, MUC17, MUC18, MUC19, MUC20 and MUC21. Mucin variants and variants of other stalk proteins can be engineered by methods known in the art, for instance, by randomized mutagenesis.

The stalk moiety may also contain or consist of other proteins that are moderately to heavily glycosylated, including native yeast wall proteins. For instance, in one embodiment of the invention, the stalk moiety contains or consists of Aga1, a variant of Aga1, or a fragment thereof.

The fusion proteins of the present invention may also include a cell wall linking member which acts to immobilize or tether the fusion protein to a host cell. The cell wall linking member can covalently or non-covalently bind the fusion protein of the invention to the yeast cell wall. In one embodiment of the invention, the stalk moiety of the fusion protein is the cell wall linking member. For instance, O-glycans from the stalk moiety can crosslink to beta glucans of the cell wall. Other cell wall linking members, include, but are not limited to, peptides containing free cysteine residues. For instance, a stalk moiety or anchor moiety containing one or more unpaired cysteine residues can form a disulfide bond(s) with one or more unpaired cysteine residues of proteins in the cell wall.

The fusion protein of the invention can optionally contain an anchor moiety which also acts to immobilize or tether the transferrin fusion protein to the host cell. The anchor moiety can be a cell wall linking member or can tether the fusion protein to a cell membrane.

One anchor domain capable of tethering the fusion protein of the present invention to a yeast cell membrane, among others, is a glycosyl-phosphatidyl-inositol (GPI) peptide anchor that is added through post-translational protein modification to the w-site in the GPI signal peptide sequence, such as the signal peptide sequence provided in SEQ ID NO.: 15. A GPI peptide anchor may also be used to anchor a fusion protein of the invention to a higher eukaryotic cell membrane, e.g., a mammalian cell membrane or a plant cell membrane. In one embodiment of the invention, an anchor such as the one provided by a modified GPI signal sequence transiently tethers the fusion protein to a host cell membrane or cell wall before being cleaved. Once cleaved, the fusion protein remains tethered to the cell via the cell wall linking member as a result of glycans from the stalk moiety being crosslinked into the beta glucans of the cell wall.

In another embodiment of the invention, the anchor is a transmembrane domain. The transmembrane domain (TMD) can be the region of a single pass type I or type II membrane protein or any one of the several transmembrane regions of a multispan membrane protein.

The present invention also includes the nucleic acid molecule that encodes the claimed fusion protein. The nucleic acid can be inserted in a vector and used to transform a host cell such as yeast. Once transformed with the nucleic acid of the present invention, the host cell can express the fusion protein. Induction of expression of the fusion protein can be controlled by methods known in the art, for instance, by use of an inducible promoter. The present invention includes a library of fusion proteins expressed in a collection of host cells, for instance, a collection of yeast cells expressing the fusion protein of the invention displaying randomized peptides.

In another embodiment of the present invention, the fusion protein is used to screen for the binding activity of a ligand or agent. A library of host cells capable of expressing the claimed fusion protein can be exposed to an agent, including but not limited to, an antigen or receptor, and then screened for binding activity. Cell surface display libraries can be screened using methods known in the art, including, but not limited to, FACS and magnetic beads.

BRIEF DESCRIPTION OF THE DRAWINGS

FIG. 8A shows the results when adding 200 µl of streptavidin and FIG. 8B shows the results when adding 40 µl of streptavidin.

DETAILED DESCRIPTION

General Description

Figure 1:
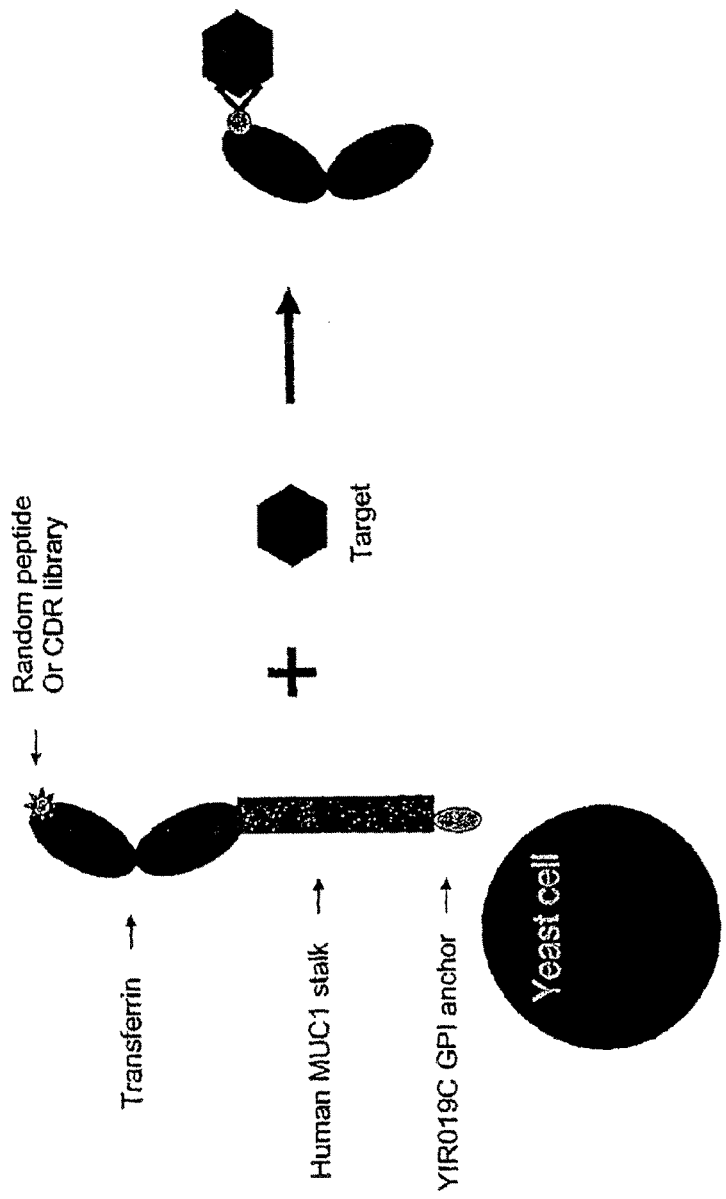
FIG. 1 shows a random peptide or CDR library displayed on a transferrin fusion protein and the binding of the ligand with a target.

The inventors of the present invention have developed a multifunctional fusion protein that can be used, for instance, as part of a cell surface display system to screen libraries, e.g., random peptide or CDR libraries. The fusion protein includes a transferrin moiety complexed with or fused to one or more ligands. The transferrin moiety can also serve as a ligand by randomizing surfaced exposed amino acid residues.

The invention includes a fusion protein containing a protein other than transferrin so long as the other protein is soluble and is capable of conferring increased serum half-life to the fused one or more ligands when cleaved from the remainder of the fusion protein, or when reconstructed without the remainder of the fusion protein. For instance, albumin or a variant or fragment thereof can be used in the place of transferrin.

In one embodiment of the invention, the transferrin moiety of the fusion protein is fused to a stalk moiety, which is moderately to heavily glycosylated. In this embodiment of the invention, the fusion protein contains a cell wall linking member which is capable of covalently or non-covalently binding the fusion protein to the cell wall of a yeast cell.

In another embodiment of the invention, the fusion protein contains an anchor moiety such as a transmembrane domain. The fusion protein may also be anchored to a cell membrane via a GPI anchor. Such anchors can be used to express the fusion protein of the invention on a mammalian cell. Although a fusion protein of the invention may contain both a stalk moiety and an anchor moiety, the invention includes fusion proteins comprising a stalk moiety and no anchor moiety as well as an anchor moiety and no stalk moiety.

In one embodiment of the invention, the fusion protein is expressed in yeast. Such a fusion protein offers advantages over the prior art including providing an increased percentage of clones with cell surface displayed peptides compared to the Aga1p and Aga2p yeast display system. The fusion protein of the invention also offers the flexibility of screening ligands that require an available N-terminus for binding. Additionally, by anchoring the fusion protein of the invention to a mammalian cell membrane, the fusion protein of the invention is also capable of being expressed and presented on mammalian cells.

The present invention also includes therapeutic compositions comprising the fusion proteins or portions thereof, and methods of treating, preventing, or ameliorating diseases or disorders by administering the fusion proteins or portions thereof to a subject in need of such a therapeutic. A fusion protein of the invention includes at least a fragment or variant of a putative therapeutic protein as a ligand moiety. In one embodiment of the invention, the transferrin and ligand, i.e., therapeutic portion of the fusion protein, can be cleaved from the cell and used to prepare a biopharmaceutical or vaccine. For instance, the therapeutic portion of the fusion protein can be cleaved from the stalk moiety or anchor.

DEFINITIONS

As used herein, the term "biological activity" refers to a function or set of activities performed by a therapeutic molecule, ligand moiety, protein or peptide in a biological context, i.e., in an organism or an in vitro facsimile thereof. Biological activities may include, but are not limited to, the functions of the therapeutic molecule portion of the claimed fusion proteins, such as, but not limited to, the induction of extracellular matrix secretion from responsive cell lines, the induction of hormone secretion, the induction of chemotaxis, the induction of mitogenesis, the induction of differentiation, or the inhibition of cell division of responsive cells. A fusion protein or peptide of the invention is considered to be biologically active if it exhibits one or more biological activities of its therapeutic protein's native counterpart.

As used herein, an "amino acid corresponding to" or an "equivalent amino acid" in a transferrin sequence is identified by alignment to maximize the identity or similarity between a first transferrin sequence and at least a second transferrin sequence. The number used to identify an equivalent amino acid in a second transferrin sequence is based on the number used to identify the corresponding amino acid in the first transferrin sequence. In certain cases, these phrases may be used to describe the amino acid residues in human transferrin compared to certain residues in rabbit serum transferrin.

As used herein, the terms "Tf moiety", "fragment of a Tf protein" or "Tf protein," or "portion of a Tf protein" refer to an amino acid sequence comprising at least about 5%, 10%, 20%, 30%, 40%, 50%, 60%, 70%, 80%, 90%, 95%, 96%, 97%, 98%, 99% or 100% of a naturally occurring Tf protein or mutant thereof.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, a "heterologous polynucleotide" or a "heterologous nucleic acid" or a "heterologous gene" or a "heterologous sequence" or an "exogenous DNA segment" refers to a polynucleotide, nucleic acid or DNA segment that originates from a source foreign to the particular host cell, or, if from the same source, is modified from its original form. A heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. As an example, a signal sequence native to a yeast cell but attached to a human Tf sequence is heterologous.

As used herein, an "isolated" nucleic acid sequence refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

As used herein, two or more DNA coding sequences are said to be "joined" or "fused" when, as a result of in-frame fusions between the DNA coding sequences, the DNA coding sequences are translated into a fusion polypeptide. The term "fusion" in reference to fusion protein comprises a ligand moiety, stalk moiety, and anchor moiety. A Tf fusion protein is a fusion of a transferrin moiety to a stalk moiety and contains a cell wall binding member.

"Modified transferrin" as used herein refers to a transferrin molecule that exhibits at least one modification of its amino acid sequence, compared to wild-type transferrin.

"Modified transferrin fusion protein" as used herein refers to a protein formed by the fusion of at least one molecule of modified transferrin (or a fragment or variant thereof) complexed or fused to a ligand, which is fused to a stalk moiety.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene.

As used herein, a DNA segment is referred to as "operably linked" when it is placed into a functional relationship with another DNA segment. For example, DNA for a signal sequence is operably linked to DNA encoding a fusion protein of the invention if it is expressed as a preprotein that participates in the secretion of the fusion protein; a promoter or enhancer is operably linked to a coding sequence if it stimulates the transcription of the sequence. Generally, DNA sequences that are operably linked are contiguous, and in the case of a signal sequence or fusion protein both contiguous and in reading phase. However, enhancers need not be contiguous with the coding sequences whose transcription they control. Linking, in this context, is accomplished by ligation at convenient restriction sites or at adapters or linkers inserted in lieu thereof.

As used herein, the term "promoter" refers to a region of DNA involved in binding RNA polymerase to initiate transcription.

As used herein, the term "recombinant" refers to a cell, tissue or organism that has undergone transformation with recombinant DNA.

As used herein, a targeting entity, protein, polypeptide or peptide refers to a molecule that binds specifically to a particular cell type, e.g., normal cell, such as a lymphocyte, or abnormal cell, such as a cancer cell, and therefore may be used to target a Tf fusion protein or compound (drug, or cytotoxic agent) to that cell type specifically.

As used herein, "therapeutic protein" refers to proteins, polypeptides, antibodies, peptides or fragments or variants thereof, having one or more therapeutic and/or biological activities. Therapeutic proteins encompassed by the invention include but are not limited to proteins, polypeptides, peptides, antibodies, and biologics. The terms peptides, proteins, and polypeptides are used interchangeably herein. Additionally, the term "therapeutic protein" may refer to the endogenous or naturally occurring correlate of a therapeutic protein. By a polypeptide displaying a "therapeutic activity" or a protein that is "therapeutically active" is meant a polypeptide that possesses one or more known biological and/or therapeutic activities associated with a therapeutic protein such as one or more of the therapeutic proteins described herein or otherwise known in the art. As a non-limiting example, a "therapeutic protein" is a protein that is useful to treat, prevent or ameliorate a disease, condition or disorder. Such a disease, condition or disorder may be in humans or in a non-human animal, e.g., veterinary use.

As used herein, the term "transformation" refers to the transfer of nucleic acid, i.e., a nucleotide polymer, into a cell. As used herein, the term "genetic transformation" refers to the transfer and incorporation of DNA, especially recombinant DNA, into a cell.

As used herein, the term "transformant" refers to a cell, tissue or organism that has undergone transformation.

As used herein, the term "transgene" refers to a nucleic acid that is inserted into an organism, host cell or vector in a manner that ensures its function.

As used herein, the term "transgenic" refers to cells, cell cultures, organisms, bacteria, fungi, animals, plants, and progeny of any of the preceding, which have received a foreign or modified gene and in particular a gene encoding a modified Tf fusion protein by one of the various methods of transformation, wherein the foreign or modified gene is from the same or different species than the species of the organism receiving the foreign or modified gene.

"Variants or variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide. As used herein, "variant" refers to a therapeutic protein portion of a transferrin fusion protein of the invention, differing in sequence from a native therapeutic protein but retaining at least one functional and/or therapeutic property thereof as described elsewhere herein or otherwise known in the art.

As used herein, the term "vector" refers broadly to any plasmid, phagemid or virus encoding an exogenous nucleic acid. The term is also be construed to include non-plasmid, non-phagemid and non-viral compounds which facilitate the transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, *Proc. Natl. Acad. Sci. U.S.A.* 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the term "wild type" refers to a polynucleotide or polypeptide sequence that is naturally occurring.

As used herein, "scaffold protein", "scaffold polypeptide", or "scaffold" refers to a protein to which amino acid sequences such as random peptides, can be fused. The peptides are exogenous to the scaffold.

As used herein, "random peptide sequence" refers to an amino acid sequence composed of two or more amino acid monomers and constructed by a stochastic or random process. A random peptide can include framework or scaffolding motifs, which may comprise invariant sequences. A random peptide sequence may contain a portion of non-variant, i.e., non-random, amino acids.

As used herein "random peptide library" refers to a set of polynucleotide sequences that encodes a set of random peptides, and to the set of random peptides encoded by those polynucleotide sequences, as well as the fusion proteins containing those random peptides.

As used herein, the term "pseudorandom" refers to a set of sequences that have limited variability, so that for example, the degree of residue variability at one position is different than the degree of residue variability at another position, but any pseudorandom position is allowed some degree of residue variation, however circumscribed.

As used herein, the term "defined sequence framework" refers to a set of defined sequences that are selected on a nonrandom basis, generally on the basis of experimental data or structural data, for example, a defined sequence framework may comprise a set of amino acid sequences that are predicted to form a n-sheet structure or may comprise a leucine zipper heptad repeat motif, a zinc-finger domain, among other variations. A "defined sequence kernal" is a set of sequences which encompass a limited scope of variability. Whereas a completely random 10-mer sequence of the 20 conventional amino acids can be any of $(20)^{10}$ sequences, and a pseudorandom 10-mer sequence of the 20 conventional amino acids can be any of $(20)^{10}$ sequences but will exhibit a bias for certain residues at certain positions and/or overall, a defined sequence kernal is a subset of sequences which is less that the maximum number of potential sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues, and the like, either segmentally or over the entire length of the individual selected library member sequence. Defined sequence kernels can refer to either amino acid sequences or polynucleotide sequences.

As used herein, "linker" or "spacer" refers to a molecule or group of molecules that connects two molecules, such as a DNA binding protein and a random peptide, and serves to place the two molecules in a desirable configuration, e.g., so that the random peptide can bind to a receptor with minimal steric hindrance from the DNA binding protein.

As used herein, the term "variable segment" refers to a portion of a nascent peptide which comprises a random, pseudorandom, or defined kernal sequence. A variable segment can comprise both variant and invariant residue positions, and the degree of residue variation at a variant residue position may be limited; both options are selected at the discretion of the practitioner. Typically, variable segments are about 3 to 20 amino acid residues in length, e.g., 8 to 10 amino acids in length, although variable segments may be longer and may comprise antibody portions or receptor proteins, such as an antibody fragment, a nucleic acid binding protein, a receptor protein and the like.

As used herein, the term "epitope" refers to that portion of an antigen or other macromolecule capable of forming a binding interaction that interacts with the variable region binding pocket of an antibody. Typically, such binding interaction is manifested as an intermolecular contact with one or more amino acid residues of a CDR.

As used herein, the term "receptor," "target," or "agent" refers to a molecule that has an affinity for a given ligand. Receptors can be naturally occurring or synthetic molecules. Receptors can be employed in an unaltered state or as aggregates with other species. Receptors can be attached, covalently or noncovalently, to a binding member, i.e., ligand, either directly or via a specific binding substance. Examples of receptors include, but are not limited to, antibodies, including monoclonal antibodies and antisera reactive with specific antigenic determinants (such as on viruses, cells, or other materials), cell membrane receptors, antigens, epitope containing molecules, complex carbohydrates and glycoproteins, enzymes and hormone receptors.

As used herein, the term "ligand" or "ligand moiety" refers to a molecule, such as a random peptide or variable segment sequence, that is recognized by a particular receptor or agent. As one of skill in the art will recognize, a molecule (or macromolecular complex) can be both a receptor and a ligand.

As used herein, "fused", "complexed" or "operably linked" is meant that the random peptide and the scaffold protein are linked together, in such a manner as to minimize the disruption to the stability of the scaffold structure.

As used herein, the term "single-chain antibody" refers to a polypeptide comprising a $V_H$ domain and a $V_L$ domain in polypeptide linkage, generally linked via a spacer peptide (e.g., [Gly-Gly-Gly-Gly-Ser]$_X$ SEQ ID NO.: 17) and which may comprise additional amino acid sequences at the amino- and/or carboxy-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino acids substantially encoded by genes of the immunoglobulin superfamily (e.g., see The Immunoglobulin Gene Superfamily, A. F. Williams and A. N. Barclay, in Immunoglobulin Genes, T. Honjo, F. W. Alt, and T. H. Rabbitts, eds., (1989) Academic Press: San Diego, Calif., pp. 361-387, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

As used herein, the term "complementarity-determining region" and "CDR" refer to the art-recognized term as exemplified by the Kabat and Chothia CDR definitions also generally known as hypervariable regions or hypervariable loops. See Chothia and Lesk (1987) J. Mol. Biol. 196: 901; Chothia et al. (1989) Nature 342: 877; E. A. Kabat et al., Sequences of Proteins of Immunological Interest (National Institutes of Health, Bethesda, Md.) (1987); and Tramontano et al. (1990) J. Mol. Biol. 215: 175. Variable region domains typically comprise the amino-terminal approximately 105-115 amino acids of a naturally-occurring immunoglobulin chain, e.g., amino acids 1-110, although variable domains somewhat shorter or longer are also suitable for forming single-chain antibodies.

An immunoglobulin light or heavy chain variable region consists of a "framework" region interrupted by three hypervariable regions, also called CDRs. The extent of the framework region and CDRs have been precisely defined. See, "Sequences of Proteins of Immunological Interest," E. Kabat et al., 4th Ed., U.S. Department of Health and Human Services, Bethesda, Md. (1987). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Transferrin and Transferrin Modifications

The fusion proteins of the present invention include a transferrin (Tf) protein or portion thereof which is able to present a ligand such as a random peptide or CDR to a receptor or agent. The Tf moiety is fused to the N-terminus of the stalk moiety. The Tf protein or portion thereof of the fusion protein may be referred to as a Tf "portion", "region" or "moiety" of the fusion protein. As used herein, a transferrin fusion protein is a transferrin protein or moiety fused to stalk moiety, and contains a cell wall linking member, and optionally an anchor moiety, or is a transferrin protein or moiety fused directly to a cell membrane anchor.

Any transferrin may be used to make modified Tf fusion proteins of the invention. As an example, a wild-type human Tf (Tf) is a 679 amino acid protein, of approximately 75 kDa (not accounting for glycosylation), with two main lobes or domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety, as well as SEQ ID NOS: 1, 2 and 3. The two domains have diverged over time but retain a large degree of identity/similarity.

Each of the N and C domains is further divided into two subdomains, N1 and N2, C1 and C2. The function of Tf is to transport iron to the cells of the body. This process is mediated by the Tf receptor (TfR), which is expressed on all cells, particularly actively growing cells. TfR recognizes the iron bound form of Tf (two molecules of which are bound per receptor), endocytosis then occurs whereby the TfR/Tf complex is transported to the endosome, at which point the localized drop in pH results in release of bound iron and the recycling of the TfR/Tf complex to the cell surface and release of Tf (known as apoTf in its un-iron bound form). Receptor binding is mainly through the C domain of Tf. The two glycosylation sites in the C domain do not appear to be involved in receptor binding as unglycosylated iron bound Tf does bind the receptor.

Each Tf molecule can carry two iron ions ($Fe^{3+}$). These are complexed in the space between the N1 and N2, C1 and C2 sub domains resulting in a conformational change in the molecule.

In human transferrin, the iron binding sites comprise at least amino acids Asp 63 (Asp 82 of SEQ ID NO: 2 which includes the native Tf signal sequence), Asp 392 (Asp 411 of SEQ ID NO: 2), Tyr 95 (Tyr 114 of SEQ ID NO: 2), Tyr 426 (Tyr 445 of SEQ ID NO: 2), Tyr 188 (Tyr 207 of SEQ ID NO: 2), Tyr 514 or 517 (Tyr 533 or Tyr 536 SEQ ID NO: 2), His 249 (His 268 of SEQ ID NO: 2), and His 585 (His 604 of SEQ ID NO: 2) of SEQ ID NO: 3. The hinge regions comprise at least N domain amino acid residues 94-96, 245-247 and/or 316-318 as well as C domain amino acid residues 425-427, 581-582 and/or 652-658 of SEQ ID NO: 3. The carbonate binding sites comprise at least amino acids Thr 120 (Thr 139 of SEQ ID NO: 2), Thr 452 (Thr 471 of SEQ ID NO: 2), Arg 124 (Arg 143 of SEQ ID NO: 2), Arg 456 (Arg 475 of SEQ ID NO: 2), Ala 126 (Ala 145 of SEQ ID NO: 2), Ala 458 (Ala 477 of SEQ ID NO: 2), Gly 127 (Gly 146 of SEQ ID NO: 2), and Gly 459 (Gly 478 of SEQ ID NO: 2) of SEQ ID NO: 3.

In one embodiment of the invention, the fusion proteins include a modified human transferrin, although any animal Tf molecule may be used to produce the fusion proteins of the invention, including human Tf variants, cow, pig, sheep, dog, rabbit, rat, mouse, hamster, echnida, platypus, chicken, frog, hornworm, monkey, ape, as well as other bovine, canine and avian species. All of these Tf sequences are readily available in GenBank and other public databases. The human Tf nucleotide sequence is available (see SEQ ID NOS: 1, 2 and 3 and the accession numbers described above and available at <www.ncbi.nlm.nih.gov>) and can be used to make genetic fusions between Tf or a domain of Tf and the therapeutic molecule of choice. Fusions may also be made from related molecules such as lacto transferrin (lactoferrin) GenBank Acc: NM_002343 or melanotransferrin.

Lactoferrin (Lf), a natural defense iron-binding protein, has been found to possess antibacterial, antimycotic, antiviral, antineoplastic and anti-inflammatory activity. The protein is present in exocrine secretions that are commonly exposed to normal flora: milk, tears, nasal exudate, saliva, bronchial mucus, gastrointestinal fluids, cervico-vaginal mucus and seminal fluid. Additionally, Lf is a major constituent of the secondary specific granules of circulating polymorphonuclear neutrophils (PMNs). The apoprotein is released on degranulation of the PMNs in septic areas. A principal function of Lf is that of scavenging free iron in fluids and inflamed areas so as to suppress free radical-mediated damage and decrease the availability of the metal to invading microbial and neoplastic cells. In a study that examined the turnover rate of $^{125}$I Lf in adults, it was shown that Lf is rapidly taken up by the liver and spleen, and the radioactivity persisted for several weeks in the liver and spleen (Bennett et al. (1979), *Clin. Sci. (Lond.)* 57: 453-460).

In one embodiment, the transferrin portion of the fusion protein of the invention includes a transferrin splice variant. In one example, a transferrin splice variant can be a splice variant of human transferrin. In one specific embodiment, the human transferrin splice variant can be that of Genbank Accession AAA61140.

In another embodiment, the transferrin portion of the fusion protein of the invention includes a lactoferrin splice variant. In one example, a human serum lactoferrin splice variant can be a novel splice variant of a neutrophil lactoferrin. In one specific embodiment, the neutrophil lactoferrin splice variant can be that of Genbank Accession AAA59479. In another specific embodiment, the neutrophil lactoferrin splice variant can comprise the following amino acid sequence EDCIALKGEADA (SEQ ID NO: 4), which includes the novel region of splice-variance.

Fusion may also be made with melanotransferrin (GenBank Acc. NM_013900, murine melanotransferrin). Melanotransferrin is a glycosylated protein found at high levels in malignant melanoma cells and was originally named human melanoma antigen p97 (Brown et al., 1982, Nature, 296: 171-173). It possesses high sequence homology with human serum transferrin, human lactoferrin, and chicken transferrin (Brown et al., 1982, Nature, 296: 171-173; Rose et al., Proc. Natl. Acad. Sci., 1986, 83: 1261-1265). However, unlike these proteins, no cellular receptor has been identified for melanotransferrin. Melanotransferrin reversibly binds iron and exists in two forms, one of which is bound to cell membranes by a glycosyl phosphatidylinositol anchor while the other form is both soluble and actively secreted (Baker et al., 1992, FEBS Lett, 298: 215-218; Alemany et al., 1993, J. Cell Sci., 104: 1155-1162; Food et al., 1994, J. Biol. Chem. 274: 7011-7017).

Modified Tf fusions may be made with any Tf protein, fragment, domain, or engineered domain. For instance, fusion proteins may be produced using the full-length Tf sequence, with or without the native Tf signal sequence. Trans-bodies may also be made using a single Tf domain, such as an individual N or C domain. Trans-bodies may also be made with a double Tf domain, such as a double N domain or a double C domain. In some embodiment, fusions of a therapeutic protein to a single C domain may be produced, wherein the C domain is altered to reduce, inhibit or prevent glycosylation, iron binding and/or Tf receptor binding. In other embodiments, the use of a single N domain is advantageous as the Tf glycosylation sites reside in the C domain and the N domain, on its own, does not bind iron or the Tf receptor. In one embodiment the Tf fusion protein has a single N domain which is expressed at a high level.

As used herein, a C terminal domain or lobe modified to function as an N-like domain is modified to exhibit glycosylation patterns or iron binding properties substantially like that of a native or wild-type N domain or lobe. In one embodiment, the C domain or lobe is modified so that it is not glycosylated and does not bind iron by substitution of the relevant C domain regions or amino acids to those present in the corresponding regions or sites of a native or wild-type N domain.

As used herein, a Tf moiety comprising "two N domains or lobes" includes a Tf molecule that is modified to replace the native C domain or lobe with a second native or wild-type N domain or lobe or a modified N domain or lobe or contains a C domain that has been modified to function substantially like a wild-type or modified N domain. See U.S. provisional application 60/406,977, which is herein incorporated by reference in its entirety.

Analysis of the two domains by overlay of the 3-dimensional structure of the two domains (Swiss PDB Viewer 3.7b2, Iterative Magic Fit) and by direct amino acid alignment (ClustalW multiple alignment) reveals that the two domains have diverged over time. Amino acid alignment shows 42% identity and 59% similarity between the two domains. However, approximately 80% of the N domain matches the C domain for structural equivalence. The C domain also has several extra disulfide bonds compared to the N domain.

Alignment of molecular models for the N and C domain reveals the following structural equivalents:

| N domain (1-330) | 4-24 | 36-72 75-88 | 94-136 | 138-139 | 149-164 | 168-173 | 178-198 200-214 | 219-255 | 259-260 | 263-268 | 271-275 | 279-280 | 283-288 290-304 | 309-327 |
|---|---|---|---|---|---|---|---|---|---|---|---|---|---|---|
| C domain (340-679) | 340-361 | 365-415 | 425-437 439-468 | 470-471 | 475-490 | 492-497 | 507-542 | 555-591 | 593-594 | 597-602 | 605-609 | 614-615 | 620-640 | 645-663 |

The disulfide bonds for the two domains align as follows:

| N | C |
|---|---|
|  | C339-C596 |
| C9-C48 | C345-C377 |
| C19-C39 | C355-C368 |
|  | C402-C674 |
|  | C418-C637 |
| C118-C194 | C450-C523 |
| *C137-C331* |  |
|  | C474-C665 |
| C158-C174 | C484-C498 |
| C161-C179 |  |
| C171-C177 | C495-C506 |
| C227-C241 | C563-C577 |
|  | C615-C620 |

Bold aligned disulfide bonds
Italics bridging peptide

In one embodiment, the transferrin portion of the fusion protein includes at least two N terminal lobes of transferrin. In further embodiments, the transferrin portion of the fusion protein includes at least two N terminal lobes of transferrin derived from human serum transferrin.

In another embodiment, the transferrin portion of the fusion protein includes, comprises, or consists of at least two N terminal lobes of transferrin having a mutation in at least one amino acid residue selected from the group consisting of Asp63, Gly65, Tyr95, Tyr188, and His249 of SEQ ID NO: 3.

In another embodiment, the transferrin portion of the modified fusion protein includes a recombinant human serum transferrin N-terminal lobe mutant having a mutation at Lys206 or His207 of SEQ ID NO: 3.

In another embodiment, the transferrin portion of the fusion protein includes, comprises, consists essentially of, or consists of at least two C terminal lobes of transferrin. In further embodiments, the transferrin portion of the fusion protein includes at least two C terminal lobes of transferrin derived from human serum transferrin.

In a further embodiment, the C terminal lobe mutant further includes a mutation of at least one of Asn413 and Asn611 of SEQ ID NO: 3 which does not allow glycosylation.

In another embodiment, the transferrin portion includes at least two C terminal lobes of transferrin having a mutation in at least one amino acid residue selected from the group consisting of Asp392, Tyr426, Tyr514, Tyr517 and His585 of SEQ ID NO: 3, wherein the mutant retains the ability to bind metal ions. In an alternate embodiment, the transferrin portion includes at least two C terminal lobes of transferrin having a mutation in at least one amino acid residue selected from the group consisting of Tyr426, Tyr514, Tyr517 and His585 of SEQ ID NO: 3, wherein the mutant has a reduced ability to bind metal ions. In another embodiment, the transferrin portion includes at least two C terminal lobes of transferrin having a mutation in at least one amino acid residue selected from the group consisting of Asp392, Tyr426, Tyr517 and His585 of SEQ ID NO:3, wherein the mutant does not retain the ability to bind metal ions and functions substantially like an N domain.

In some embodiments, the Tf or Tf portion will be of sufficient length to increase the in vivo circulatory half-life, serum stability, in vitro solution stability or bioavailability of the ligand, i.e., therapeutic, when the Tf or Tf portion and ligand of the fusion protein are cleaved from the remainder of the fusion protein compared to the in vivo circulatory half-life, serum stability (half-life), in vitro stability or bioavailability of the ligand in an unfused state, i.e., not fused to Tf. Such an increase in stability, in vivo circulatory half-life or bioavailability may be about a 30%, 50%, 70%, 80%, 90% or more increase over the unfused ligand moiety region. In some cases, the ligand moiety comprising modified transferrin exhibit a serum half-life of about 1 or more days, 1-2 or more days, 3-5 or more days, 5-10 or more days, 10-15 or more days, 10-20 or more days, about 12-18 days or about 14-17 days compared to the ligand in an unfused state.

When the C domain of Tf is part of the fusion protein, the two N-linked glycosylation sites, amino acid residues corresponding to N413 and N611 of SEQ ID NO:3 may be mutated for expression in a yeast system to prevent glycosylation or hypermannosylation and extend the serum half-life of the fusion protein (to produce asialo-, or in some instances, monosialo-Tf or disialo-Tf). In addition to Tf amino acids corresponding to N413 and N611, mutations to the residues within or adjacent to the N-X-S/T glycosylation site prevent or substantially reduce glycosylation. See U.S. Pat. No. 5,986,067 of Funk et al. For instance, the invention includes modifications at amino acids S415 and T613. In one embodiment, the transferrin moiety contains the modifications S415A and T613A. In this embodiment, the amino acid modifications correspond to S415 and T613 of SEQ ID NO.: 3.

It has also been reported that the N domain of Tf expressed in *Pichia pastoris* becomes O-linked glycosylated with a single hexose at S32 which also may be mutated or modified to prevent such glycosylation. Moreover, O-linked glycosylation may be reduced or eliminated in a yeast host cell with mutations in one or more of the PMT genes.

Accordingly, in one embodiment of the invention, the fusion protein includes a modified transferrin molecule wherein the transferrin exhibits reduced glycosylation, including but not limited to asialo- monosialo- and disialo-forms of Tf. In another embodiment, the transferrin portion of the fusion protein includes a recombinant transferrin mutant that is mutated to prevent glycosylation. In another embodiment, the transferrin portion of the fusion protein includes a recombinant transferrin mutant that is fully glycosylated. In a further embodiment, the transferrin portion of the fusion protein includes a recombinant human serum transferrin mutant that is mutated to prevent glycosylation, wherein at least one of Asn413 and Asn611 of SEQ ID NO:3 is mutated to an amino acid which does not allow glycosylation. In another embodiment, the transferrin portion of the fusion protein includes a recombinant human serum transferrin mutant that is mutated to prevent or substantially reduce glycosylation, wherein mutations may to the residues within the N-X-S/T glycosylation site. Moreover, glycosylation may be reduced or prevented by mutating the serine or threonine residue. For instance, in one embodiment of the invention, the transferrin portion of the fusion protein includes a recombinant human serum transferrin mutant that is mutated to prevent glycosylation, wherein at least one of Ser415 and Thr613 of SEQ ID NO:3 is mutated to an amino acid which does not allow glycosylation. Further, changing the X to proline is known to inhibit glycosylation.

As discussed below in more detail, modified Tf fusion proteins, comprising a modified Tf, of the invention may also be engineered to not bind iron and/or not bind the Tf receptor. In other embodiments of the invention, iron binding is retained, and the iron binding ability of Tf may be used to deliver a therapeutic protein or peptide(s) to the inside of a cell and/or across the blood brain barrier (BBB). The N domain alone will not bind to TfR when loaded with iron, and the iron bound C domain will bind TfR but not with the same affinity as the whole molecule.

In another embodiment, the transferrin portion of the transferrin fusion protein, includes a recombinant transferrin mutant having a mutation wherein the mutant does not retain the ability to bind metal ions. In an alternate embodiment, the transferrin portion of the transferrin fusion protein includes a recombinant transferrin mutant having a mutation wherein the mutant has a weaker binding affinity for metal ions than wild-type serum transferrin. In an alternate embodiment, the transferrin portion of the transferrin fusion protein includes a recombinant transferrin mutant having a mutation wherein the mutant has a stronger binding affinity for metal ions than wild-type serum transferrin.

In another embodiment, the transferrin portion includes a recombinant transferrin mutant having a mutation wherein the mutant does not retain the ability to bind to the transferrin receptor. In an alternate embodiment, the transferrin portion includes a recombinant transferrin mutant having a mutation wherein the mutant has a weaker binding affinity for the transferrin receptor than wild-type serum transferrin. In an alternate embodiment, the transferrin portion includes a recombinant transferrin mutant having a mutation wherein the mutant has a stronger binding affinity for the transferrin receptor than wild-type serum transferrin.

In another embodiment, the transferrin portion includes a recombinant transferrin mutant having a mutation wherein the mutant does not retain the ability to bind to carbonate ions. In an alternate embodiment, the transferrin portion includes a recombinant transferrin mutant having a mutation wherein the mutant has a weaker binding affinity for carbonate ions than wild-type serum transferrin. In an alternate embodiment, the transferrin portion includes a recombinant transferrin mutant having a mutation wherein the mutant has a stronger binding affinity for carbonate ions than wild-type serum transferrin.

In another embodiment, the transferrin portion includes a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO: 3, wherein the mutant retains the ability to bind metal ions. In an alternate embodiment, a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO: 3, wherein the mutant has a reduced ability to bind metal ions. In another embodiment, a recombinant human serum transferrin mutant having a mutation in at least one amino acid residue selected from the group consisting of Asp63, Gly65, Tyr95, Tyr188, His249, Asp392, Tyr426, Tyr517 and His585 of SEQ ID NO: 3, wherein the mutant does not retain the ability to bind metal ions.

In another embodiment, the transferrin portion includes a recombinant human serum transferrin mutant having a mutation at Lys206 or His207 of SEQ ID NO: 3, wherein the mutant has a stronger binding avidity for metal ions than wild-type human serum transferrin (see U.S. Pat. No. 5,986,067, which is herein incorporated by reference in its entirety).

In an alternate embodiment, the transferrin portion includes a recombinant human serum transferrin mutant having a mutation at Lys206 or His207 of SEQ ID NO: 3, wherein the mutant has a weaker binding avidity for metal ions than wild-type human serum transferrin. In a further embodiment, the transferrin portion includes a recombinant human serum transferrin mutant having a mutation at Lys206 or His 207 of SEQ ID NO:3, wherein the mutant does not bind metal ions.

Any available technique may be used to produce the fusion protein of the invention, including but not limited to molecular techniques commonly available, for instance, those disclosed in Sambrook et al., Molecular Cloning: A Laboratory Manual, 2nd Ed., Cold Spring Harbor Laboratory Press, 1989. When carrying out nucleotide substitutions using techniques for accomplishing site-specific mutagenesis that are well known in the art, the encoded amino acid changes are preferably of a minor nature, that is, conservative amino acid substitutions, although other, non-conservative, substitutions are contemplated as well, particularly when producing a modified transferrin portion, e.g., a modified fusion protein exhibiting reduced glycosylation, reduced iron binding and the like. Specifically contemplated are amino acid substitutions, small deletions or insertions, typically of one to about 30 amino acids; insertions between transferrin domains; small amino- or carboxyl-terminal extensions, such as an amino-terminal methionine residue, or small linker peptides of less than 50, 40, 30, 20 or 10 residues between transferrin domains or linking a transferrin protein and therapeutic protein or peptide, ligand, or an antibody variable region or stalk region; or a small extension that facilitates purification, such as a poly-histidine tract, an antigenic epitope or a binding domain.

Examples of conservative amino acid substitutions are substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

Non-conservative substitutions encompass substitutions of amino acids in one group by amino acids in another group, For example, a non-conservative substitution would include the substitution of a polar amino acid for a hydrophobic amino acid. For a general description of nucleotide substitution, see, e.g., Ford et al. (1991), *Prot. Exp. Pur.* 2: 95-107. Non-conservative substitutions, deletions and insertions are particularly useful to produce Tf fusion proteins, preferably trans-bodies, of the invention that exhibit no or reduced binding of iron and/or no or reduced binding of the fusion protein to the Tf receptor.

In the polypeptide and proteins of the invention, the following system is followed for designating amino acids in accordance with the following conventional list:

Table of Amino Acids

| AMINO ACID | ONE-LETTER SYMBOL | THREE-LETTER SYMBOL |
|---|---|---|
| Alanine | A | Ala |
| Arginine | R | Arg |
| Asparagine | N | Asn |
| Aspartic Acid | D | Asp |
| Cysteine | C | Cys |
| Glutamine | Q | Gln |
| Glutamic Acid | E | Glu |

-continued

| AMINO ACID | ONE-LETTER SYMBOL | THREE-LETTER SYMBOL |
|---|---|---|
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Iron binding and/or receptor binding may be reduced or disrupted by mutation, including deletion, substitution or insertion into, amino acid residues corresponding to one or more of Tf N domain residues Asp63, Tyr95, Tyr188, His249 and/or C domain residues Asp 392, Tyr 426, Tyr 514 and/or His 585 of SEQ ID NO: 3. Iron binding may also be affected by mutation to amino acids Lys206, His207 or Arg632 of SEQ ID NO: 3. Carbonate binding may be reduced or disrupted by mutation, including deletion, substitution or insertion into, amino acid residues corresponding to one or more of Tf N domain residues Thr120, Arg124, Ala126, Gly 127 and/or C domain residues Thr 452, Arg 456, Ala 458 and/or Gly 459 of SEQ ID NO: 3. A reduction or disruption of carbonate binding may adversely affect iron and/or receptor binding.

Binding to the Tf receptor may be reduced or disrupted by mutation, including deletion, substitution or insertion into, amino acid residues corresponding to one or more of Tf N domain residues described above for iron binding.

As discussed above, glycosylation may be reduced or prevented by mutation, including deletion, substitution or insertion into, amino acid residues corresponding to one or more of Tf C domain residues within the N-X-S/T sites corresponding to C domain residues N413 and/or N611. See U.S. Pat. No. 5,986,067. For instance, the N413 and/or N611 may be mutated to Glu residues as may be the adjacent amino acids. In one embodiment, S415 and/or T613 are mutated to Ala residues.

In instances where the Tf fusion proteins of the invention are not modified to prevent glycosylation, iron binding, carbonate binding and/or receptor binding, glycosylation, iron and/or carbonate ions may be stripped from or cleaved off of the fusion protein. For instance, available deglycosylases may be used to cleave glycosylation residues from the fusion protein, in particular the sugar residues attached to the Tf portion, yeast deficient in glycosylation enzymes may be used to prevent glycosylation and/or recombinant cells may be grown in the presence of an agent that prevents glycosylation, e.g., tunicamycin.

The carbohydrates on the fusion protein may also be reduced or completely removed enzymatically by treating the fusion protein with deglycosylases. Deglycosylases are well known in the art. Examples of deglycosylases include, but are not limited to, galactosidase, PNGase A, PNGase F, glucosidase, mannosidase, fucosidase, and Endo H deglycosylase.

Additional mutations may be made to Tf to alter the three dimensional structure of Tf, such as modifications to the hinge region to prevent the conformational change needed for iron binding and Tf receptor recognition. For instance, mutations may be made in or around N domain amino acid residues 94-96, 245-247 and/or 316-318 as well as C domain amino acid residues 425-427, 581-582 and/or 652-658. In addition, mutations may be made in or around the flanking regions of these sites to alter Tf structure and function.

In one aspect of the invention, the fusion protein can function as a carrier protein to extend the half life or bioavailability of the ligand as well as, in some instances, delivering the ligand inside cells, and retains the ability to cross the blood brain barrier. In an alternate embodiment, the fusion protein includes a modified transferrin molecule wherein the transferrin does not retain the ability to cross the blood brain barrier.

In another embodiment, the fusion protein includes a modified transferrin molecule wherein the transferrin molecule retains the ability to bind to the transferrin receptor and transport the antibody variable region inside cells. In an alternate embodiment, the fusion protein includes a modified transferrin molecule wherein the transferrin molecule does not retain the ability to bind to the transferrin receptor and transport the antibody variable region inside cells.

In further embodiments, the fusion protein includes a modified transferrin molecule wherein the transferrin molecule retains the ability to bind to the transferrin receptor and transport the antibody variable region inside cells, but does not retain the ability to cross the blood brain barrier. In an alternate embodiment, the fusion protein includes a modified transferrin molecule wherein the transferrin molecule retains the ability to cross the blood brain barrier, but does not retain the ability to bind to the transferrin receptor and transport the antibody variable region inside cells.

Transferrin Fusion Proteins

The fusion proteins of the invention may contain one or more copies of the ligand, antibody variable region or random peptide attached to the N-terminus and/or the C-terminus of the Tf protein. In one embodiment, the ligand moiety is attached to the N-terminus of the Tf protein. In some embodiments, the ligand, variable region or peptide is attached to both the N- and C-terminus of the Tf protein and the fusion protein may contain one or more equivalents of these regions on either or both ends of Tf.

In other embodiments, the one or more ligands are inserted into the transferrin peptide, for instance at known domains of the Tf protein such as into one or more of the loops of Tf. See Ali et al. (1999) *J. Biol. Chem.* 274(34):24066-24073.

In one embodiment of the invention, the ligand is inserted in the N lobe of transferrin. For instance, the invention also includes one or more insertions can be made at or around other positions in the $N_1$ and $N_2$ domains of the N-lobe as shown in the table below.

| $N_1$ | $N_2$ |
|---|---|
| Asp33 | Ser105 |
| Asn55 | Glu141 |
| Asn75 | Asp166 |
| Asp90 | Gln184 |
| Gly257 | Asp197 |
| Lys280 | Lys217 |
| His289 | Thr231 |
| Ser298 | Cys241 |

In yet another embodiment, the ligand comprises randomized amino acid residues at surface exposed amino acid residues of the transferrin protein. The randomized amino acid residues can be located in one region of surface exposed amino acids or in more than one region of surface exposed amino acids. For instance, the randomized amino acids can be contained in one or more of the regions consisting of about amino acid residue 85 to about amino acid residue 92, about amino acid residue 276 to about amino acid residue 298, or about amino acid residue 207 to about amino acid residue 217 of SEQ ID NO.: 3. In one embodiment of the invention, the randomized amino acid residues are located at positions Y85, G86, S87, E89, D90 and Q92 of SEQ ID NO.: 3. In another embodiment, the randomized amino acid residues are located at positions K276, D277, K280, Q283, S286 and D297 and optionally S298 of SEQ ID NO.: 3. In yet another embodiment, the randomized amino acid residues are located at positions 1-1207, S208, F211, E212 and A215 and optionally N216 and/or K217 of SEQ ID NO.: 3.

Although the number of randomized amino acid residues per region can vary, preferably at least about 3, at least about 4, at least about 5, at least about 6, at least about 7, at least about 8, at least about 9 or at least about 10 or more amino acid residues are randomized per region.

In one embodiment of the invention, the ligand moiety contains a known ligand binding sequence such as a ligand sequence capable of binding to an integrin, including, but not limited to, an alpha 4 integrin (e.g., a4b1 and a4b7). Such ligands include, but are not limited to, VCAM and MadCAM. See Jackson, 2002, Current Pharmaceutical Design. *: 1229-1253 which is herein incorporated in its entirety for all purposes.

The inflammatory processes leading to tissue damage and disease are mediated in part by the alpha 4 integrins, a4b1 and a4b7, expressed on the leukocyte cell surface. These glycoprotein receptors modulate cell adhesion via interaction with their primary ligands, vascular cell adhesion molecule (VCAM) and mucosal addressin cell adhesion molecule (MAdCAM), expressed in the affected tissue. Upon binding, the combined integrin/CAM interactions at the cell surface result in firm adhesion of the leukocyte to the vessel wall followed by entry into the affected tissue. Elevated cell adhesion molecule (CAM) expression in various organs has been linked with several autoimmune diseases. In one embodiment of the invention, a transbody (i.e., a fusion protein comprising transferrin and a ligand) containing one or more peptides capable of binding to alpha 4 integrins or their CAM ligands can be administered to a subject to treat and/or mediate inflammation. In one embodiment of the invention, a transbody containing one or more peptides capable of binding to alpha-4 integrins or their CAM ligands can be administered to a subject for treatment of an autoimmune disease.

In another embodiment of the invention, the ligand moiety comprises a known ligand binding sequence and randomized amino acid residues either within the ligand binding sequence or on either or both sides of the ligand binding sequence. For instance, the invention includes a transferrin fusion protein containing the integrin binding sequence RGD surrounded by randomized amino acid residues. Such a fusion protein can be inserted in the transferrin moiety, for instance, between amino acids 289 and 290 of SEQ ID NO.: 3. In one embodiment of the invention, the integrin binding sequence and randomized peptide ligand moiety is CXXXRGDXXXC, wherein X is a randomized amino acid residue. In another embodiment of the invention, the integrin binding sequence and randomized peptide ligand moiety is XXXRGDXXX. The invention also includes, but is not limited to, the integrin binding sequence KGD surrounded by randomized peptides and the integrin binding sequence LDV surrounded by randomized peptides.

In another embodiment of the invention, the ligand moiety is an antibody variable region. In this embodiment, generally, the transferrin fusion protein of the invention may have one modified transferrin-derived region and one antibody variable region. However, more than one antibody variable region may be used to make a transferrin fusion protein of the invention, thereby producing a multi-functional modified Tf fusion protein.

In one embodiment, the fusion protein of the invention contains an antibody variable region or portion thereof fused to a transferrin molecule or portion thereof. In another embodiment, the fusion protein of the inventions contains an antibody variable region fused to the N terminus of a transferrin molecule. In an alternate embodiment, the fusion protein of the invention contains an antibody variable region fused to the C terminus of a transferrin molecule. In a further embodiment, the fusion protein of the invention contains a transferrin molecule fused to the N terminus of an antibody variable region. In an alternate embodiment, the fusion protein of the invention contains a transferrin molecule fused to the C terminus of an antibody variable region.

The present invention also provides a fusion protein containing an antibody variable region or portion thereof fused to a modified transferrin molecule or portion thereof.

In other embodiments, the fusion protein of the inventions contains an antibody variable region fused to both the N-terminus and the C-terminus of modified transferrin. In another embodiment, the antibody variable regions fused at the N- and C-termini bind the same antigens. Also, the antibody variable regions that bind the same antigen may be derived from different antibodies, and thus, bind different epitopes on the same target. In an alternate embodiment, the antibody variable regions fused at the N- and C-termini bind different antigens. In another alternate embodiment, the antibody variable regions fused to the N- and C-termini bind different antigens which may be useful for activating two different cells for the treatment or prevention of disease, disorder, or condition. In another embodiment, the antibody variable regions fused at the N- and C-termini bind different antigens which may be useful for bridging two different antigens for the treatment or prevention of diseases or disorders which are known in the art to commonly occur in patients simultaneously.

Additionally, transferrin fusion protein of the invention may also be produced by inserting the antibody variable region of interest, e.g., a single chain antibody that binds a therapeutic protein or a fragment or variant thereof, into an internal region of the modified transferrin. Internal regions of modified transferrin include, but are not limited to, the loop regions, the iron binding sites, the hinge regions, the bicarbonate binding sites or the receptor binding domain.

Within the protein sequence of the modified transferrin molecule a number of loops or turns exist, which are stabilized by disulfide bonds. These loops are useful for the insertion, or internal fusion, of therapeutically active peptides, preferably antibody variable regions, particularly those requiring a secondary structure to be functional, or therapeutic proteins, preferably antibody variable region, to generate a modified transferrin molecule with specific biological activity.

When ligands such as antibody variable regions, preferably CDRs, are inserted into or replace at least one loop of a Tf molecule, insertions may be made within any of the surface exposed loop regions, in addition to other areas of Tf. For instance, insertions may be made within the loops comprising Tf amino acids 32-33, 74-75, 256-257, 279-280 and 288-289. See Ali et al., supra. As previously described, insertions may also be made within other regions of Tf such as the sites for iron and bicarbonate binding, hinge regions, and the receptor binding domain as described in more detail below. The loops in the Tf protein sequence that are amenable to modification/replacement for the insertion of proteins or peptides may also be used for the development of a screenable library of random peptide inserts. Any procedures may be used to produce nucleic acid inserts for the generation of peptide libraries, including available phage and bacterial display systems, prior to cloning into a Tf domain and/or fusion to the ends of Tf.

The N-terminus of Tf is free and points away from the body of the fusion protein. Fusions of a ligand or ligands on the N-terminus of transferrin is one embodiment of the invention. Such fusions may include a linker region, such as but not limited to a poly-glycine stretch or a PEAPTD linker (SEQ ID NO.: 18) to separate the ligand from Tf.

The C-terminus of Tf appears may be buried or partially buried and secured by a disulfide bond 6 amino acids from the C-terminus. In human Tf, the C-terminal amino acid is a proline which, depending on the way that it is orientated, will either point a fusion protein away or into the body of the molecule. A linker or spacer moiety at the C-terminus may be used in some embodiments of the invention. There is also a proline near the N-terminus. In one aspect of the invention, the proline at the N- and/or the C-termini may be modified or substituted with another amino acid. In another aspect of the invention, the C-terminal disulfide bond may be eliminated to untether the C-terminus.

Stalk Moiety

The stalk moiety of the invention is fused at its N-terminus to a transferrin moiety or ligand and may optionally be fused with an anchor moiety at its C-terminus. When expressed in a yeast cell, the C-terminus of the stalk moiety is located within the cell, for instance, within the cell wall. In one embodiment of the invention, the stalk moiety acts as a cell wall linking member to covalently or non-covalently bind the fusion protein to the cell wall of a yeast cell.

The stalk moiety of the present invention has a rod-like or brush-like conformation. This type of conformation is typical of a moderately to heavily glycosylated peptide. The stalk moiety of the invention contains N-glycans or O-glycans. See U.S. Pat. No. 6,114,147 which is herein incorporated by reference in its entirety. The presence of O-glycans is preferred over N-glycans because O-glycans allow the stalk moiety to take on more of an extended, rod-like conformation as compared to N-glycans. The stalk moiety may also contain moderate to heavy glycosylation of serine and threonine glycosylation sites.

The stalk moiety of the fusion protein of the invention contains a moderate to high percentage of serine or threonine residues. For instance, the invention includes a stalk moiety with at least about 5% or more serine and/or threonine residues, at least about 10% or more serine and/or threonine residues, at least about 20% or more or more serine and/or threonine residues, at least about 30% or more or more serine and/or threonine residues, at least about 40% or more or more serine and/or threonine residues, at least about 50% or more or more serine and/or threonine residues, at least about 60% or more or more serine and/or threonine residues, at least about 70% or more or more serine and/or threonine residues, at least about 80% or more or more serine and/or threonine residues, or at least about 90% or more or more serine and/or threonine residues. In one embodiment of the invention, the stalk moiety contains about 20-30% serine and/or threonine residues, about 20-40% serine and/or threonine residues, about 30-40% serine and/or threonine residues, about 20-50% serine and/or threonine residues, about 30-50% serine and/or threonine residues, about 20-60 serine and/or threonine residues or about 30-60% serine and/or threonine residues.

The stalk moiety may contain at least about 5% or more N- or O-glycans by weight, at least about 10% or more N- or O-glycans by weight, at least about 20% or more N- or O-glycans by weight, at least about 30% or more N- or O-glycans by weight, at least about 40% or more N- or O-glycans by weight, at least about 50% or more N- or O-glycans by weight, at least about 60% or more N- or O-glycans by weight, at least about 70% or more N- or O-glycans by weight, at least about 80% or more N- or O-glycans by weight, or at least about 90% or more N- or O-glycans by weight. In one embodiment of the invention, the stalk moiety contains about 20-30% O-glycans by weight, about 20-40% O-glycans by weight, about 30-40% O-glycans by weight, about 20-50% O-glycans by weight, about 30-50% O-glycans by weight, about 20-60% O-glycans by weight or about 30-60% O-glycans. In another embodiment, the presence of glycans, in particular O-glycans, allows the stalk moiety to crosslink with beta glucans present in proteins of the cell wall. As such, the stalk moiety of the invention is capable of functioning as a cell wall linking member.

The stalk moiety can comprise a mucin protein or portion of a mucin protein, i.e. a member of the MUC-type proteins. MUC-type mucins are a family of structurally related molecules that are heavily glycosylated and are expressed in epithelia of the respiratory, gastrointestinal, and reproductive tracts, e.g., MUC1 (GenBank Accession No. AF125525), MUC2 (GenBank Accession No L21998), MUC3 (GenBank Accession No AF113616), MUC4 (GenBank Accession No AJ000281), MUC5AC (GenBank Accession No U83139), MUC5B (GenBank Accession No AJ001402), MUC6 (GenBank Accession No U97698), MUC7 (GenBank Accession No L13283), MUC8 (GenBank Accession No U14383), MUC9 (GenBank Accession No AW271430). In one embodiment of the invention, the stalk moiety contains hMUC1 or a portion of the hMUC1 protein, for instance, SEQ ID NO.: 71 encoded by the nucleic acid of SEQ ID NO.: 70 as well as the polypeptide encoded by the nucleic acid of SEQ ID NO: 5. In another embodiment of the invention, the stalk moiety contains hMUC3 or a portion of the hMUC3 protein. For instance, the invention includes the hMUC3 stalk of SEQ ID NO.: 69 which is encoded by the nucleic acid of SEQ ID NO.: 68.

The fusion protein of the invention also includes stalks comprising variants such as analogs and derivatives of mucin proteins, mucin-like proteins and portions thereof. Variants may be created to optimize display proteins on the surface of a cell. Variants can be created by methods known in the art. For instance, variants can be engineered by removing repetitive amino acid residues and/or subjecting peptides to random mutagenesis and selection.

The stalk moiety of the present invention can also be derived from glycosylated proteins other than mucin, including, but not limited to, AGA1 (for instance, SEQ ID NO.: 73, encoded by the nucleic acid sequence of SEQ ID NO.: 72), MAdCAM-1, GlyCAM-1, CD34; consensus repeats from E-selectin, P-selectin, or L-selectin; or viral glycoprotein spikes (such as influenza, herpes simplex, human immunodeficiency, or tobacco mosaic virus) and variants and fragments thereof. See WO 01/46698, Girard et al., (1995) Immunity 2:113-123, and Van Kinken et al. (1998) Anal. Biochem. 265:103-116, all of which are herein incorporated by reference in their entireties. The invention includes repeats of two or more glycosylated proteins or fragments thereof as well as combinations of two or more types of glycosylated proteins.

In another embodiment of the invention, the stalk is engineered to contain one or more free cysteine residues. The one or more free cysteine residues are capable of forming disulfide bonds with free cysteine residues of proteins in the cell wall of a yeast cell. The formation of one or more disulfide bonds within the cell wall represents another method that can be used to engineer a stalk moiety capable of functioning as a cell wall binding member.

If the fusion protein of the invention is to be expressed in a yeast cell, the stalk moiety is preferably of sufficient length to span the entire cell wall of a yeast cell. Preferably, the N-terminus of the stalk moiety is situated on the outside of the cell wall, most preferably, extended in a rod-like configuration away from the yeast cell to reduce steric hindrance between the transferrin moiety and ligand and the host yeast cell. The stalk moiety should be at least about 25 amino acids, at least about 50 amino acids, at least about 75 amino acids, at least about 100 amino acids, at least about 125 amino acids, at least about 150 amino acids, at least about 175 amino acids, at least about 200 amino acids, at least about 225 amino acids, at least about 250 amino acids, at least about 275 amino acids, at least about 300 amino acids, at least about 325 amino acids, at least about 350 amino acids, at least about 375 amino acids, at least about 400 amino acids, at least about 425 amino acids, at least about 450 amino acids, at least about 475 amino acids in length, at least about 500 amino acids in length, at least about 525 amino acids in length, at least about 550 amino acids in length, at least about 575 amino acids in length, at least about 600 amino acids in length, at least about 625 amino acids in length, or at least about 650 amino acids in length. In one embodiment, the stalk moiety is about 500 amino acids in length. In another embodiment, the stalk moiety is about 300 to 600 amino acids in length.

Anchor Moiety

The anchor moiety of the fusion protein of the present invention is a portion of the fusion protein that physically tethers the fusion protein to a host cell surface or substrate surface. In one embodiment of the invention, the anchor moiety tethers the fusion protein to a cell membrane such as, but not limited to, a mammalian cell membrane. In another embodiment of the invention, the anchor moiety can tether or immobilize the fusion protein to a cell wall such as, but not limited to, a yeast cell wall. When the anchor tethers the fusion protein to a cell wall it is a cell wall linking member.

The anchor moiety can transiently tether a fusion protein to a cell wall or cell membrane. In one embodiment of the invention, the anchor moiety transiently tethers a fusion protein to a cell wall or cell membrane which provides an opportunity for the stalk moiety to become covalently or non-covalently bound to the cell wall. For instance, the transient tethering of an anchor in a cell may allow O-glycans from a stalk moiety to crosslink with beta glucans of the cell wall.

In one embodiment of the present invention, the anchor moiety sticks into cell membranes or walls of microorganisms, for instance, lower eukaryotes such as yeasts and molds as well as mammalian cells such as mammalian cell lines. The anchor moiety may have a long C terminus which anchors it in the cell membrane or cell wall with amino acids such as proline (Kok (1990) FEMS Microbiology Reviews 87: 15-42).

An anchor moiety can be anchored to a cell by use of a glycosyl phosphatidylinositol (GPI) anchor. See Conzelmann et al. EMBO 9: 653-661 and Lipke and Ovalle (1998) J. Bacteriol. 180: 3735-3740. A GPI signal sequence peptide, such as the GPI signal peptides disclosed herein, signals for attachment of GPI to the C terminus of the fusion protein. The GPI signal itself has three domains: the region containing the GPI attachment site (the ω site) plus the first and second amino acids downstream of the ω site, a spacer of 5 to 10 amino acids, and a hydrophobic stretch of 10 to 15 amino acids. A protein containing the GPI signal is cleaved at the ω site, and the resulting carboxy terminus of the protein is covalently bound to the GPI moiety. This reaction occurs in the endoplasmic reticulum. Being associated with membranes by means of the GPI moiety, GPI-attached proteins are then transported to the cell surface and remain on the plasma membrane as GPI-anchored proteins if the proteins contain basic residues (R and/or K) in the short ω-minus region. GPI-associated proteins with V, I, or L at the ω-4/-5 site and Y or N at the ω-2 site are incorporated in the cell membrane. See Hamada et al. (1999) J. Bacteriol. 181: 3886-3889; Nuoffer et al. (1993) J. Biol. Chem. 268: 10558-10563; De Nobel et al. (1994) Trends Cell Biol. 4: 42-45.; Hamada et al. (1998) Mol. Gen. Genet. 258: 53-59; and Van Der Vaart et al. (1998) Biotechnol. Genet. Eng. Rev. 15: 387-411.

Figure 2:
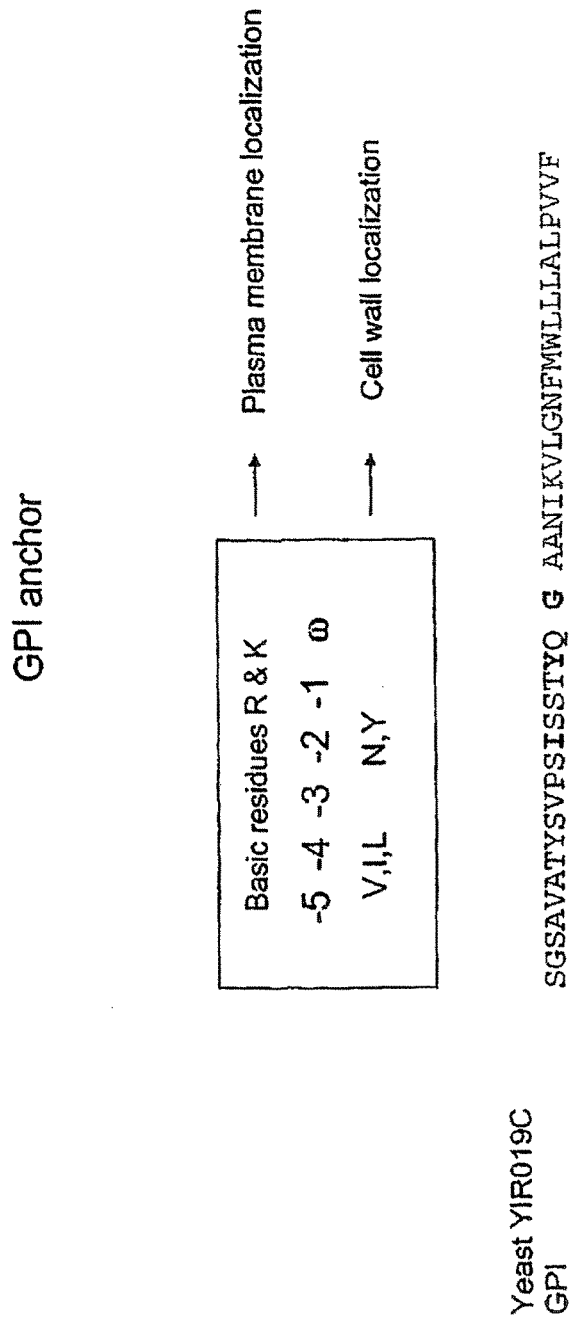
FIG. 2 provides the yeast YIR019C GPI anchor peptide sequence (SEQ ID NO: 15) and highlights the amino acids responsible for cell membrane attachment.

In one embodiment of the invention, yeast GPI YIR019C is used to provide the anchor moiety of the transferrin fusion protein. FIG. 2 provides a diagram of the GPI YIR019C. The ω site in the amino acid sequence (SEQ ID NO: 15) is glycine and is illustrated as having a space on either side of it. The spaces are indicative of spacer regions on either side of the ω site. The I and Y amino acids in bold-faced print are the ω-5/-4 and -2 sites, respectively.

Several *Saccharomyces* anchor moieties are known in the art and can be used to construct the fusion proteins of the present invention. Other examples of yeast GPI signal proteins include, but are not limited to, YDR534C, YNL327W, YOR214C, YDR134C, YPL130, YOR009W, YER150W, YDR077W, YOR383C, YJR151C, YJR004, YJL078C, YLR110C, and YNL300W. Further, GPI signal proteins can be used from other organisms such as the GPI of EPA1 of *Ganidida glabrata*, Hwp1p of *Candida albicans*, or VSG of *Trypanosoma brucei*.

In one embodiment of the invention, the anchor moiety is a mammalian moiety or derivative or fragment thereof. In another embodiment of the invention, a GPI signal peptide is a mammalian GPI signal protein. For instance, the present invention includes derivatives of human MDP GPI signal protein such as those disclosed in Table 1 (see Example 5).

The invention also includes a fusion protein comprising an anchor moiety with one or more unbound cysteine residues. The cysteine residues can act to tether the fusion protein to the cell by forming disulfide bonds with cysteine residues of proteins in the cell wall.

The invention includes fusion proteins comprising a transmembrane domains (TMD) as an anchor moiety. In one embodiment of the invention, the TMD is a region of a single pass type I or type II membrane protein. For instance, the invention includes, but is not limited to, residues 70-98 of FUS1.

In another embodiment of the invention, the TMD comprises one or more of the several transmembrane regions of a multispan membrane protein. In one embodiment of the invention, the TMD is a hydrophobic region of a multispan membrane protein comprising about 10 to 60 amino acids, about 15 to 60 amino acids, about 20 to 60 amino acids, about 30 to 60 amino acids or about 25 to 50 amino acids. For instance, the invention includes, but is not limited to, one or more TMDs from STE6 of *Saccharomyces* from the group consisting of residues 25-30, 73-100, 171-198, 249-277, 714-742, 761-789, 838-858, 864-884, 940-967 and 979-1000 (Saccharomyces Genome Database annotation).

In another embodiment, the anchor moiety is used to tether the transferrin fusion protein to a solid substrate such as a microarray. The anchor moiety is preferably a short epitope tag (i.e. a sequence recognized by an antibody, typically a monoclonal antibody) such as polyhistidine, SEAP, or M1 and M2 flag. See Bush et al. (1991) J. Biol. Chem. 266: 13811-13814, Berger et al. (1988) Gene 66: 1-10, U.S. Pat. No. 5,011,912, U.S. Pat. No. 4,851,341, U.S. Pat. No. 4,703,004, and U.S. Pat. No. 4,782,137, all of which are incorporated by reference in their entirety. In one embodiment, the stalk domain is tethered to a substrate by an anti-stalk sequence antibody such as an anti-mucin antibody.

Albumin

The invention also includes a fusion protein which employs a protein or protein fragment other than transferrin to "present" a ligand to a target. Suitable proteins are ones which are soluble and at least about 50 amino acids in length or longer. In one embodiment of the invention, the protein or protein fragment contains a secondary structure similar to that of transferrin.

It is preferable that the protein or fragment thereof be capable of increasing the half-life of the ligand when cleaved from the stalk portion of the fusion protein and used as a therapeutic. For instance, the present invention envisions the use of a fusion protein containing an albumin moiety, a stalk moiety and a cell wall linking member. The present invention also envisions the use of a fusion protein containing an albumin moiety and an anchor moiety. The albumin moiety is capable of conferring increased serum half-life to the ligand, i.e., therapeutic, when the albumin and ligand portion of the fusion protein is cleaved from the remainder of the fusion protein and administered to a patient in need of the ligand as a therapeutic.

A fusion protein containing an albumin moiety may contain an albumin protein, an albumin variant or a fragment thereof. In one embodiment, the albumin protein comprises the amino acid sequence of SEQ ID NO.: 67 which is encoded by the nucleic acid sequence of SEQ ID NO.: 66. The invention includes modifications of albumin that are known in the art.

Nucleic Acids

Nucleic acid molecules are also provided by the present invention. These encode a modified Tf fusion protein comprising a transferrin protein or a portion of a transferrin protein covalently linked or joined to a ligand moiety. The fusion protein may further comprise a linker region, for instance a linker less than about 50, 40, 30, 20, or amino acid residues. The linker can be covalently linked to and between the transferrin protein or portion thereof and the ligand portion. Nucleic acid molecules of the invention may be purified or not.

Host cells and vectors for replicating the nucleic acid molecules and for expressing the encoded fusion proteins are also provided. Any vectors or host cells may be used, whether prokaryotic or eukaryotic, but eukaryotic expression systems, in particular yeast expression systems and mammalian expression systems, may be preferred. Many vectors and host cells are known in the art for such purposes. It is well within the skill of the art to select an appropriate set for the desired application.

DNA sequences encoding transferrin, portions of transferrin and therapeutic proteins of interest may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA or protein sequences (see, for example, Baldwin, G. S. (1993) Comparison of Transferrin Sequences from Different Species. Comp. Biochem. Physiol. 106B/1:203-218 and all references cited therein, which are hereby incorporated by reference in their entirety). Alternatively, the polymerase chain reaction (PCR)

method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of ordinary skill in the art.

As known in the art, "similarity" between two polynucleotides or polypeptides is determined by comparing the nucleotide or amino acid sequence and its conserved nucleotide or amino acid substitutes of one polynucleotide or polypeptide to the sequence of a second polynucleotide or polypeptide. Also known in the art is "identity" which means the degree of sequence relatedness between two polypeptide or two polynucleotide sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

While there exist a number of methods to measure identity and similarity between two polynucleotide or polypeptide sequences, the terms "identity" and "similarity" are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity or similarity between two sequences include, but are not limited to those disclosed in Guide to Huge Computers, Martin J. Bishop, ed., Academic Press, San Diego, 1994, and Carillo, H., and Lipman, D., SIAM J. Applied Math. 48:1073 (1988).

Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, et al., Nucl. Acid Res. 12(1):387 (1984)), BLASTP, BLASTN, FASTA (Atschul, et al., J. Mol. Biol. 215:403 (1990)). The degree of similarity or identity referred to above is determined as the degree of identity between the two sequences, often indicating a derivation of the first sequence from the second. The degree of identity between two nucleic acid sequences may be determined by means of computer programs known in the art such as GAP provided in the GCG program package (Needleman and Wunsch J. Mol. Biol. 48:443-453 (1970)). For purposes of determining the degree of identity between two nucleic acid sequences for the present invention, GAP is used with the following settings: GAP creation penalty of 5.0 and GAP extension penalty of 0.3.

Codon Optimization

The degeneracy of the genetic code permits variations of the nucleotide sequence of a transferrin protein and/or therapeutic protein of interest, while still producing a polypeptide having the identical amino acid sequence as the polypeptide encoded by the native DNA sequence. The procedure, known as "codon optimization" (described in U.S. Pat. No. 5,547,871 which is incorporated herein by reference in its entirety) provides one with a means of designing such an altered DNA sequence. The design of codon optimized genes should take into account a variety of factors, including the frequency of codon usage in an organism, nearest neighbor frequencies, RNA stability, the potential for secondary structure formation, the route of synthesis and the intended future DNA manipulations of that gene. In particular, available methods may be used to alter the codons encoding a given fusion protein with those most readily recognized by yeast when yeast expression systems are used.

The degeneracy of the genetic code permits the same amino acid sequence to be encoded and translated in many different ways. For example, leucine, serine and arginine are each encoded by six different codons, while valine, proline, threonine, alanine and glycine are each encoded by four different codons. However, the frequency of use of such synonymous codons varies from genome to genome among eukaryotes and prokaryotes. For example, synonymous codon-choice patterns among mammals are very similar, while evolutionarily distant organisms such as yeast (*S. cerevisiae*), bacteria (such as *E. coli*) and insects (such as *D. melanogaster*) reveal a clearly different pattern of genomic codon use frequencies (Grantham, R., et al., Nucl. Acid Res., 8, 49-62 (1980); Grantham, R., et al., Nucl. Acid Res., 9, 43-74 (1981); Maroyama, T., et al., Nucl. Acid Res., 14, 151-197 (1986); Aota, S., et al., Nucl. Acid Res., 16, 315-402 (1988); Wada, K., et al., Nucl. Acid Res., 19 Supp., 1981-1985 (1991); Kurland, C. G., FEBS Lett., 285, 165-169 (1991)). These differences in codon-choice patterns appear to contribute to the overall expression levels of individual genes by modulating peptide elongation rates. (Kurland, C. G., FEBS Lett., 285, 165-169 (1991); Pedersen, S., EMBO J., 3, 2895-2898 (1984); Sorensen, M. A., J. Mol. Biol., 207, 365-377 (1989); Randall, L. L., et al., Eur. J. Biochem., 107, 375-379 (1980); Curran, J. F., and Yarus, M., J. Mol. Biol., 209, 65-77 (1989); Varenne, S., et al., J. Mol. Biol., 180, 549-576 (1984), Varenne, S., et al., J. Mol, Biol., 180, 549-576 (1984); Garel, J. -P., J. Theor. Biol., 43, 211-225 (1974); Ikemura, T., J. Mol. Biol., 146, 1-21 (1981); Ikemura, T., J. Mol. Biol., 151, 389-409 (1981)).

Codon usage frequencies for a synthetic gene should reflect the codon usages of nuclear genes derived from the exact (or as closely related as possible) genome of the cell/organism that is intended to be used for recombinant protein expression, particularly that of yeast species. As discussed above, in one embodiment the human Tf sequence is codon optimized, before or after modification as herein described for yeast expression as may be the therapeutic protein nucleotide sequence(s).

Vectors

Expression units for use in the present invention will generally comprise the following elements, operably linked in a 5' to 3' orientation: a transcriptional promoter, a secretory signal sequence, a DNA sequence encoding a modified Tf fusion protein comprising transferrin protein or a portion of a transferrin protein joined to a DNA sequence encoding a therapeutic protein or peptide of interest and a transcriptional terminator. As discussed above, any arrangement of the therapeutic protein or peptide fused to or within the Tf portion may be used in the vectors of the invention. The selection of suitable promoters, signal sequences and terminators will be determined by the selected host cell and will be evident to one skilled in the art and are discussed more specifically below.

Suitable yeast vectors for use in the present invention are described in U.S. Pat. No. 6,291,212 and include YRp7 (Struhl et al., Proc. Natl. Acad. Sci. USA 76: 1035-1039, 1978), YEp13 (Broach et al., Gene 8: 121-133, 1979), pJDB249 and pJDB219 (Beggs, Nature 275:104-108, 1978), pPPC0005, pSeCHSA, pScNHSA, pC4 and derivatives thereof. Useful yeast plasmid vectors also include pRS403-

406, pRS413-416 and the Pichia vectors available from Stratagene Cloning Systems, La Jolla, Calif. 92037, USA. Plasmids pRS403, pRS404, pRS405 and pRS406 are Yeast Integrating plasmids (Ylps) and incorporate the yeast selectable markers HIS3, TRP1, LEU2 and URA3. Plasmids pRS413-41.6 are Yeast Centromere plasmids (YCps).

Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., Gene 8: 17, 1979), HIS3 (Struhl et al., ibid.) or POT1 (Kawasaki and Bell, EP 171,142). Other suitable selectable markers include the CAT gene, which confers chloramphenicol resistance on yeast cells. Preferred promoters for use in yeast include promoters from yeast glycolytic genes (Hitzeman et al., J. Biol. Chem. 225: 12073-12080, 1980; Alber and Kawasaki, J. Mol. Appl. Genet. 1: 419-434, 1982; Kawasaki, U.S. Pat. No. 4,599,311) or alcohol dehydrogenase genes (Young et al., in Genetic Engineering of Microorganisms for Chemicals, Hollaender et al., (eds.), p. 355, Plenum, N.Y., 1982; Ammerer, Meth. Enzymol. 101: 192-201, 1983). In this regard, promoters that can be used are the TPI1 promoter (Kawasaki, U.S. Pat. No. 4,599,311) and the ADH2-4$^C$ (see U.S. Pat. No. 6,291,212 promoter (Russell et al., Nature 304: 652-654, 1983). The expression units may also include a transcriptional terminator. One transcriptional terminator is the TPI1 terminator (Alber and Kawasaki, ibid.).

In addition to yeast, modified fusion proteins of the present invention can be expressed in filamentous fungi, for example, strains of the fungi Aspergillus. Examples of useful promoters include those derived from Aspergillus nidulans glycolytic genes, such as the adh3 promoter (McKnight et al., EMBO J. 4: 2093-2099, 1985) and the tpiA promoter. An example of a suitable terminator is the adh3 terminator (McKnight et al., ibid.). The expression units utilizing such components may be cloned into vectors that are capable of insertion into the chromosomal DNA of Aspergillus, for example.

Mammalian expression vectors for use in carrying out the present invention will include a promoter capable of directing the transcription of the modified Tf fusion protein. Promoters include, but are not limited to, viral promoters and cellular promoters. For instance, viral promoters include the major late promoter from adenovirus 2 (Kaufman and Sharp, Mol. Cell. Biol. 2: 1304-13199, 1982) and the SV40 promoter (Subramani et al., Mol. Cell. Biol. 1: 854-864, 1981). Cellular promoters include the mouse metallothionein 1 promoter (Palmiter et al., Science 222: 809-814, 1983) and a mouse V6 (see U.S. Pat. No. 6,291,212) promoter (Grant et al., Nuc. Acids Res. 15: 5496, 1987). One such promoter is a mouse $V_H$ (see U.S. Pat. No. 6,291,212) promoter (Loh et al., ibid.). Such expression vectors may also contain a set of RNA splice sites located downstream from the promoter and upstream from the DNA sequence encoding the transferrin fusion protein. RNA splice sites may be obtained, for instance, from adenovirus and/or immunoglobulin genes.

Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto at al., Nucl. Acid Res. 9: 3719-3730, 1981). One such polyadenylation signal is the $V_H$ (see U.S. Pat. No. 6,291,212) gene terminator (Loh et al., ibid.). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse: (see U.S. Pat. No. 6,291,212) enhancer (Gillies, Cell 33: 717-728, 1983). Expression vectors may also include sequences encoding the adenovirus VA RNAs.

Transformation

Techniques for transforming fungi are well known in the literature, and have been described, for instance, by Beggs (ibid.), Hinnen et al. (Proc. Natl. Acad. Sci. USA 75: 1929-1933, 1978), Yelton et al., (Proc. Natl. Acad. Sci. USA 81: 1740-1747, 1984), and Russell (Nature 301: 167-169, 1983). The genotype of the host cell will generally contain a genetic defect that is complemented by the selectable marker present on the expression vector. Choice of a particular host and selectable marker is well within the level of ordinary skill in the art.

Cloned DNA sequences comprising modified Tf fusion proteins of the invention may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann et al., EMBO J. 1: 841-845, 1982), or lipofection may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene. One amplifiable marker is the DHFR$^r$ (see U.S. Pat. No. 6,291,212) cDNA (Simonsen and Levinson, Proc. Natl. Acad. Sci. USA 80: 2495-2499, 1983). Selectable markers are reviewed by Thilly (Mammalian Cell Technology, Butterworth Publishers, Stoneham, Mass.) and the choice of selectable markers is well within the level of ordinary skill in the art.

Host Cells

The present invention also includes a cell, for instance, a yeast cell or a mammalian cell, transformed to express a modified transferrin fusion protein of the invention. In addition to the transformed host cells themselves, the present invention also includes a culture of those cells, for instance, a monoclonal (clonally homogeneous) culture, or a culture derived from a monoclonal culture in a nutrient medium. If the polypeptide is secreted, the medium will contain the polypeptide, with the cells, or without the cells if they have been filtered or centrifuged away.

Host cells for use in practicing the present invention include eukaryotic cells, and in some cases prokaryotic cells, capable of being transformed or transfected with exogenous DNA and grown in culture, such as cultured mammalian, insect, fungal, plant and bacterial cells.

Fungal cells, including species of yeast (e.g., Saccharomyces spp., Schizosaccharomyces spp., Pichia spp.) may be used as host cells within the present invention. Exemplary genera of yeast contemplated to be useful in the practice, of the present invention as hosts for expressing the, transferrin fusion protein of the inventions are Pichia (including species formerly classified as Hansenula), Saccharomyces, Kluyveromyces, Aspergillus, Candida, Torulopsis, Torulaspora, Schizosaccharomyces, Citeromyces, Pachysolen,

*Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis,* and the like. Examples of *Saccharomyces* spp. are *S. cerevisiae, S. italicus* and *S. rouxii.* Examples of *Kluyveromyces* spp. are *K. lactis* and *K. marxianus.* A suitable species is *T. delbrueckii.* Examples of *Pichia* (Hansenula) spp. are *P. angusta* (formerly *H. polymorpha*), *P. anomala* (formerly *H. anomala*) and *P. pastoris.*

Particularly useful host cells to produce the Tf fusion proteins of the invention are the methanoltrophic *Pichia pastoris* (Steinlein et al., (1995) Protein Express. Purif. 6:619-624). *Pichia pastoris* has been developed to be an outstanding host for the production of foreign proteins since its alcohol oxidase promoter was isolated and cloned; its transformation was first reported in 1985. *P. pastoris* can utilize methanol as a carbon source in the absence of glucose. The *P. pastoris* expression system can use the methanol-induced alcohol oxidase (AOX1) promoter, which controls the gene that codes for the expression of alcohol oxidase, the enzyme which catalyzes the first step in the metabolism of methanol. This promoter has been characterized and incorporated into a series of *P. pastoris* expression vectors. Since the proteins produced in *P. pastoris* are typically folded correctly and secreted into the medium, the fermentation of genetically engineered *P. pastoris* provides an excellent alternative to *E. coli* expression systems. A number of proteins have been produced using this system, including tetanus toxin fragment, *Bordetella pertussis* pertactin, human serum albumin and lysozyme.

The transformation of *F. oxysporum* may, for instance, be carried out as described by Malardier et al., (1989) Gene 78:147-156.

Strains of the yeast *Saccharomyces cerevisiae* are another preferred host. In a one embodiment, a yeast cell, or more specifically, a *Saccharomyces cerevisiae* host cell that contains a genetic deficiency in a gene required for asparagine-linked glycosylation of glycoproteins is used. *S. cerevisiae* host cells having such defects may be prepared using standard techniques of mutation and selection, although many available yeast strains have been modified to prevent or reduce glycosylation or hypermannosylation. Ballou et al. (J. Biol. Chem. 255: 5986-5991, 1980) have described the isolation of mannoprotein biosynthesis mutants that are defective in genes which affect asparagine-linked glycosylation. Gentzsch and Tanner (Glycobiology 7:481-486, 1997) have described a family of at least six genes (PMT1-6) encoding enzymes responsible for the first step in O-glycosylation of proteins in yeast. Mutants defective in one or more of these genes show reduced O-linked glycosylation and/or altered specificity of O-glycosylation.

To optimize production of the heterologous proteins, it may be preferred that the host strain carries a mutation, such as the *S. cerevisiae* pep4 mutation (Jones, Genetics 85: 23-33, 1977), which results in reduced proteolytic activity. Host strains containing mutations in other protease encoding regions are particularly useful to produce large quantities of the Tf fusion proteins of the invention.

Host cells containing DNA constructs of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient which are complemented by the selectable marker on the DNA construct or co-transfected with the DNA construct. Yeast cells, for example, are preferably grown in a chemically defined medium, comprising a carbon source, e.g. sucrose, a non-amino acid nitrogen source, inorganic salts, vitamins and essential amino acid supplements. The pH of the medium is preferably maintained at a pH greater than 2 and less than 8, preferably at pH 5.5 to 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. One such osmotic stabilizer is sorbitol supplemented into the medium at a concentration between 0.1 M and 1.5 M., preferably at 0.5 M or 1.0 M.

Cultured mammalian cells are generally grown in commercially available serum-containing or serum-free media. Selection of a medium appropriate for the particular cell line used is within the level of ordinary skill in the art. Transfected mammalian cells are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Baculovirus/insect cell expression systems may also be used to produce the modified Tf fusion proteins of the invention. The BacPAK™ Baculovirus Expression System (BD Biosciences (Clontech)) expresses recombinant proteins at high levels in insect host cells. The target gene is inserted into a transfer vector, which is cotransfected into insect host cells with the linearized BacPAK6 viral DNA. The BacPAK6 DNA is missing an essential portion of the baculovirus genome. When the DNA recombines with the vector, the essential element is restored and the target gene is transferred to the baculovirus genome. Following recombination, a few viral plaques are picked and purified, and the recombinant phenotype is verified. The newly isolated recombinant virus can then be amplified and used to infect insect cell cultures to produce large amounts of the desired protein.

Secretory Signal Sequences

The terms "secretory signal sequence" or "signal sequence" or "secretion leader sequence" are used interchangeably and are described, for example in U.S. Pat. No. 6,291,212 and U.S. Pat. No. 5,547,871, both of which are herein incorporated by reference in their entirety. Secretory signal sequences or signal sequences or secretion leader sequences encode secretory peptides. A secretory peptide is an amino acid sequence that acts to direct the secretion of a mature polypeptide or protein from a cell. Secretory peptides are generally characterized by a core of hydrophobic amino acids and are typically (but not exclusively) found at the amino termini of newly synthesized proteins. Very often the secretory peptide is cleaved from the mature protein during secretion. Secretory peptides may contain processing sites that allow cleavage of the signal peptide from the mature protein as it passes through the secretory pathway. Processing sites may be encoded within the signal peptide or may be added to the signal peptide by, for example, in vitro mutagenesis.

Secretory peptides may be used to direct the secretion of modified Tf fusion proteins of the invention. One such secretary peptide that may be used in combination with other secretory peptides is the third domain of the yeast Barrier protein. Secretory signal sequences or signal sequences or secretion leader sequences are required for a complex series of post-translational processing steps which result in secretion of a protein. If an intact signal sequence is present, the protein being expressed enters the lumen of the rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Preferred signal sequences improve the processing and export efficiency of recombinant protein expression using viral, mammalian or yeast expression vectors. In some cases, the native Tf signal sequence may be used to express and secrete fusion proteins of the invention.

Linkers

The Tf moiety and the ligand of the modified transferrin fusion proteins of the invention can be fused directly or using a linker peptide of various lengths to provide greater physical separation and allow more spatial mobility between the fused proteins and thus maximize the accessibility of the antibody variable region, for instance, for binding to its cognate receptor. The linker peptide may consist of amino acids that are flexible or more rigid. In one embodiment, the invention includes a substantially non-helical linker such as $(PEAPTD)_n$ (SEQ ID NO.: 18). In another embodiment, the fusion protein of the invention contains a linker with a polyglycine stretch. The linker can be less than about 50, 40, 30, 20, or 10 amino acid residues. The linker can be covalently linked to and between the transferrin protein or portion thereof and the antibody variable region.

Linkers may also be used to join antibody variable regions within a ligand or ligands. Suitable linkers for joining the antibody variable regions are those that allow the antibody variable regions to fold into a three dimensional structure that maintains the binding specificity of a whole antibody.

Screening Methods

The number of possible target molecules for which ligands may be identified by screening fusion protein libraries of the present invention is virtually unlimited. For example, the target molecule, i.e. receptor or agent, may be an antibody (or a binding portion thereof) or antigen. The antigen to which the antibody binds may be known and perhaps even sequenced, in which case the invention may be used to map epitopes of the antigen. If the antigen is unknown, such as with certain autoimmune diseases, for example, sera, fluids, tissue, or cells from patients with the disease can be used in the present screening method to identify peptides, and consequently the antigen, that elicits the autoimmune response. Once a peptide has been identified, that peptide can serve as, or provide the basis for, the development of a vaccine, a therapeutic agent, a diagnostic reagent, etc. See WO 01/46698 for a list of target molecules on which the ligands may be screened, which is herein incorporated by reference in its entirety for all purposes.

Screening may be performed by using one of the methods well known to the practitioner in the art, such as by biopanning, FACS or MACS®. In one embodiment of the invention, screening is performed for receptor activation. The target can be either purified and in solution or surface bound or cell associated. The target may be labeled, for instance, with biotin or by other methods known in the art.

Polypeptides and peptides having the desired property can be isolated and identified by sequencing of the corresponding nucleic acid sequence or by amino acid sequencing or mass spectrometry. Subsequent optimization may be performed by repeating the replacement of sub-sequences by different sequences, preferably by random sequences, and the screening step one or more times.

Once a peptide library is constructed, host cells are transformed with the library vectors. The successful transformants are typically selected by growth in a selective medium or under selective conditions, e.g., an appropriate growth medium or others depending on the vector used. This selection may be done on solid or in liquid growth medium. For growth of bacterial cells on solid medium, the cells are grown at a high density (about. $10^8$ to $10^9$ transformants per $m^2$) on a large surface of, for example, L-agar containing the selective antibiotic to form essentially a confluent lawn. For growth in liquid culture, cells may be grown in L-broth (with antibiotic selection) through about 10 or more doublings. Growth in liquid culture may be more convenient because of the size of the libraries, while growth on solid media likely provides less chance of bias during the amplification process.

If a transferrin fusion protein peptide library is to be screened by yeast cell surface display, yeast cells will be transformed with the expression vector coding for the transferrin fusion protein. A full range of mutagenesis methods is consistent with yeast surface display library construction such as error-prone polymerase chain reaction and DNA shuffling. See Boder et al. (2000) Methods of Enzymology 328: 430-444. Alternatively, the tranferrin moiety of the expressed fusion proteins can serve as a scaffold for random peptide sequences or CDRs.

Several approaches are known in the art for identifying desirable peptides once a yeast cell transferrin fusion protein peptide library has been created. For example, peptides can be distinguished by equilibrated binding with low concentrations of fluorescently labeled target, i.e. receptor or agent, in cases of fairly low affinity concentrations ($K_d$>nM, or no affinity if the library is being screened to isolate a novel binding specificity). For applications designed to evolve tight-binding proteins, excessively large volumes of dilute target solutions may be necessary to maintain molar ligand excess, complicating handling of samples. In such cases, improvements in binding affinity may be approximated by changes in dissociation kinetics. Kinetic competition for a stoichiometrically limiting target can be used to identify improved clones within the population (Hawkins et al. (1992) J. Mol. Biol. 226: 889); however, this approach eliminates the quantitative predictability of the screening approach and is not recommended in general. See Boder et al. (2000) Methods of Enzymology 328: 430-444.

Targets can be biotinylated or fluorescently labeled, or alternatively, a ligand of interest, i.e. a peptide displayed on transferrin, can be labeled. Preferably, the targets are labeled. Labeled targets, e.g. biotinylated targets, can be incubated with a transferrin fusion protein peptide library. The library may have at least about $10^4$ members (i.e. displayed peptides), at least about $10^6$ members, at least about $10^6$ members, at least about $10^7$ members, at least about $10^8$ members, at least about $10^9$ members, at least about $10^{10}$ members, at least about $10^{11}$ members, at least about $10^{12}$ members, at least about $10^{13}$ members, at least about $10^{14}$ members, at least about $10^{15}$ members, or at least about $10^{16}$ members.

After incubation, cells can be labeled with a second label such as secondary antibodies, a steptavidin labeled molecules, or other method known in the art. The secondary antibody can be an anti-biotin antibody. Streptavidin labeled molecules, include, but are not limited to, streptavidin-phycoerythrin or streptavidin microbeads.

Flow cytometry can be used to analyze cell populations as known in the art. When this is done, only the displaying fraction of the population is analyzed. See Boder et al. (2000) Methods of Enzymology 328: 430-444 and Kondo et al. (2004) Appl. Microbiol. Biotechnol. 64: 28-40, both of which are herein incorporated by reference in their entirety.

Alternatively, if a second label consisting of labeled beads is used, i.e. anti-biotin or streptavidin labeled beads, the mixture of ligands and target molecules can be sorted using a magnetic sorting protocol as described in Yeung et al. (2002) Biotechnol. Prog. 18: 212-220, which is herein incorporated by reference in its entirety. A MACS® MicroBeads kit can be used with this screening protocol (Miltenyi Biotec GmbH). Magnetic sorting can be used in conjunction with FACS.

In one embodiment of the present invention, it is desirable to characterize a single ligand of interest expressed in a yeast cell. The expressed protein may be screened in a variety of ways. If the protein has a function it may be directly assayed. For example, single chain antibodies expressed on the yeast surface are fully functional and may be screened based on binding to an antigen. If the protein does not have a detectable function that can be easily assayed, expression of the ligand may be monitored using an antibody. Because a yeast cell is much larger than phage, one can use flow cytometry to monitor the phenotype of the protein on a single yeast cell.

In another embodiment of the present invention, binding of the ligand moiety with a receptor or agent is performed by a means known in the art, other than cell surface display, such as by ELISA, competition binding assays when the target's native binding partner is known, sandwich assays, radioreceptor assays using a radioactive ligand whose binding is blocked by the peptide library, etc. In these methods, host cells transformed with the Tf fusion protein peptide library are lysed. The Tf fusion protein peptides are anchored to the assay substrate via an appropriate anchor moiety such as, but not limited to, an anti-MUC1 antibody. The screening process involves reacting the Tf peptide library with the target of interest to establish a baseline binding level against which the binding activities of subsequent peptide libraries are compared. The nature of the assay is not critical so long as it is sufficiently sensitive to detect small quantities of peptide binding to or competing for binding to the target. The assay conditions may be varied to take into account optimal binding conditions for different binding substances of interest or other biological activities. Thus, the pH, temperature, salt concentration, volume and duration of binding, etc. may all be varied to achieve binding of peptide to target under conditions which resemble those of the environment of interest.

Once it is determined that the Tf peptide library possesses a peptide or peptides which bind to the target of interest, the methods of the invention can be used to identify the sequence of the peptide(s) in the mixture. Cells displaying peptides that bind the target can be isolated from the general population of the library by MACS or FACS screening. The screening process is repeated 2 to 3 times on the initial isolates to deplete any nonspecific binders. A final round of screening by FACS sorting to isolate based on binding affinity is then performed. Plasmid DNA is recovered from isolated cells, and the DNA for the region of the insert is sequenced to determine the protein sequence. Common motifs between the isolates can then be determined.

Therapeutic Ligand Molecules

The ligands of the invention can be putative or known therapeutic molecules. As used herein, a therapeutic molecule is typically a protein or peptide capable of exerting a beneficial biological effect in vitro or in vivo and includes proteins or peptides that exert a beneficial effect in relation to normal homeostasis, physiology or a disease state. Therapeutic molecules do not include fusion partners commonly used as markers or protein purification aids, such as galactosidases (see for example, U.S. Pat. No. 5,986,067 and Aldred et al. (1984) *Biochem. Biophys. Res. Commun.* 122: 960-965). For instance, a beneficial effect as related to a disease state includes any effect that is advantageous to the treated subject, including disease prevention, disease stabilization, the lessening or alleviation of disease symptoms or a modulation, alleviation or cure of the underlying defect to produce an effect beneficial to the treated subject.

A therapeutic ligand may be fused directly to a transferrin moiety or indirectly via a linker moiety as previously described. In one embodiment, it may be desirable to cleave the fusion protein to separate the transferrin and ligand portion of the fusion protein from the remainder of the fusion protein. In another embodiment, it may be desirable to cleave the ligand from the remainder of the fusion protein.

The ligand moiety of the fusion protein of the invention may contain at least a fragment or variant of a therapeutic protein, and/or at least a fragment or variant of an antibody. In a further embodiment, the fusion proteins can contain peptide fragments or peptide variants of proteins or antibodies wherein the variant or fragment retains at least one biological or therapeutic activity. The fusion proteins can contain therapeutic proteins that can be peptide fragments or peptide variants at least about 3, at least about 4, at least 5, at least 6, at least 7, at least 8, at least 9, at least 10, at least 11, at least 12, at least 13, at least 14, at least 15, at least 20, at least 25, at least 30, at least 35, or at least about 40, at least about 50, at least about 55, at least about 60 or at least about 70 or more amino acids in length fused to the N and/or C termini, inserted within, or inserted into a loop of a modified transferrin.

In another embodiment, the ligand moiety of the fusion protein of the present invention contains a therapeutic protein portion that can be fragments of a therapeutic protein that include the full length protein as well as polypeptides having one or more residues deleted from the amino terminus of the amino acid sequence.

In another embodiment, the ligand moiety of the fusion protein of the present invention contains a therapeutic protein portion that can be fragments of a therapeutic protein that include the full length protein as well as polypeptides having one or more residues deleted from the carboxy terminus of the amino acid sequence.

In another embodiment, the ligand moiety of the fusion proteins of the present invention contain a therapeutic protein portion that can have one or more amino acids deleted from both the amino and the carboxy termini.

In another embodiment, the fusion protein contains a therapeutic protein portion, i.e. ligand moiety, that is at least about 80%, 85%, 90%, 95%, 96%, 97%, 98% or 99% identical to a reference therapeutic protein set forth herein, or fragments thereof. In further embodiments, the transferrin fusion molecules contain a therapeutic protein portion that is at least about 80%, 85%, 90%, 95%, 96%, 97%, 98% or 99% identical to reference polypeptides having the amino acid sequence of N- and C-terminal deletions as described above.

In another embodiment, the fusion protein contains the therapeutic protein portion that is at least about 80%, 85%, 90%, 95%, 96%, 97%, 98%, 99% or 100%, identical to, for example, the native or wild-type amino acid sequence of a therapeutic protein. Fragments, of these polypeptides are also provided.

The therapeutic proteins corresponding to a therapeutic protein portion of a modified transferrin fusion protein of the invention, such as cell surface and secretory proteins, can be modified by the attachment of one or more oligosaccharide groups. The modification referred to as glycosylation, can significantly affect the physical properties of proteins and can be important in protein stability, secretion, and localization. Glycosylation occurs at specific locations along the polypeptide backbone. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be an amino acid except proline. Variables such as protein structure and cell type influence the number and nature of the carbohydrate units within the chains at different glycosylation sites. Glycosylation isomers are also common at the same site within a given cell type. For example, several types of human interferon are glycosylated.

Therapeutic proteins corresponding to a therapeutic protein portion of a fusion protein of the invention, as well as analogs and variants thereof, may be modified so that glycosylation at one or more sites is altered as a result of manipulation(s) of their nucleic acid sequence by the host cell in which they are expressed, or due to other conditions of their expression. For example, glycosylation isomers may be produced by abolishing or introducing glycosylation sites, e.g., by substitution or deletion of amino acid residues, such as substitution of glutamine for asparagine, or unglycosylated recombinant proteins may be produced by expressing the proteins in host cells that will not glycosylate them, e.g. in glycosylation-deficient yeast. These approaches are known in the art.

Therapeutic proteins and their nucleic acid sequences are well known in the art and available in public databases such as Chemical Abstracts Services Databases (e.g., the CAS Registry), GenBank, and GenSeq. The Accession Numbers and sequences referred to below are herein incorporated by reference in their entirety.

The present invention is further directed to fusion proteins comprising fragments of the therapeutic proteins herein described. Even if deletion of one or more amino acids from the N-terminus of a protein results in modification or loss of one or more biological functions of the therapeutic protein portion, other therapeutic activities and/or functional activities (e.g., biological activities, ability to multimerize, ability to bind a ligand) may still be retained. For example, the ability of polypeptides with N-terminal deletions to induce and/or bind to antibodies which recognize the complete or mature forms of the polypeptides generally will be retained with less than the majority of the residues of the complete polypeptide removed from the N-terminus. Whether a particular polypeptide lacking N-terminal residues of a complete polypeptide retains such immunologic activities can be assayed by routine methods described herein and otherwise known in the art. It is not unlikely that a mutant with a large number of deleted N-terminal amino acid residues may retain some biological or immunogenic activities. In fact, peptides composed of as few as six amino acid residues may often evoke an immune response.

Also as mentioned above, even if deletion of one or more amino acids from the N-terminus or C-terminus of a therapeutic protein results in modification or loss of one or more biological functions of the protein, other functional activities, e.g., biological activities, ability to multimerize, ability to bind a ligand, and/or therapeutic activities may still be retained. For example the ability of polypeptides with C-terminal deletions to induce and/or bind to antibodies which recognize the complete or mature forms of the polypeptide generally will be retained when less than the majority of the residues of the complete or mature polypeptide are removed from the C-terminus. Whether a particular polypeptide lacking the N-terminal and/or, C-terminal residues of a reference polypeptide retains therapeutic activity can readily be determined by routine methods described herein and/or otherwise known in the art.

Peptide fragments of the therapeutic proteins can be fragments comprising, or alternatively, consisting of, an amino acid sequence that displays a therapeutic activity and/or functional activity, e.g., biological activity, of the polypeptide sequence of the therapeutic protein of which the amino acid sequence is a fragment.

Other polypeptide fragments are biologically active fragments. Biologically active fragments are those exhibiting activity similar, but not necessarily identical, to an activity of a therapeutic protein used in the present invention. The biological activity of the fragments may include an improved desired activity, or a decreased undesirable activity.

Generally, variants of proteins are overall very similar, and, in many regions, identical to the amino acid sequence of the therapeutic protein corresponding to a therapeutic protein portion of a transferrin fusion protein of the invention. Nucleic acids encoding these variants are also encompassed by the invention.

Further therapeutic polypeptides that may be used in the invention are polypeptides encoded by polynucleotides which hybridize to the complement of a nucleic acid molecule encoding an amino acid sequence of a therapeutic protein under stringent hybridization conditions which are known to those of skill in the art. See, for example, Ausubel, F. M. et al., eds., 1989 Current protocol in Molecular Biology, Green Publishing Associates, Inc., and John Wiley & Sons Inc., New. York. Polynucleotides encoding these polypeptides are also encompassed by the invention.

By a polypeptide-having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence, or in one or more contiguous groups within the reference sequence.

As a practical matter, whether any particular polypeptide is at least about 80%, 85%, 90%, 95%, 96%, 97%, 98% or 99% identical to, for instance, the amino acid sequence of a fusion protein of the invention or a fragment thereof (such, as the therapeutic protein portion of the fusion protein or portion thereof), can be determined conventionally using known computer programs. One method for determining the best overall match between a query sequence (a sequence of the present invention) and a subject sequence, also referred to as a global sequence alignment, can be determined using the FASTDB computer program based on the algorithm of Brufiag et al. (Comp. App. Biosci 245-(1990)).

The polynucleotide variants of the invention may contain alterations in the coding regions, non-coding regions, or both. Polynucleotide variants containing alterations which produce silent substitutions, additions, or deletions, but do not alter the properties or activities of the encoded polypeptide may be used to produce modified ligand moieties. Nucleotide variants produced by silent substitutions due to the degeneracy of the genetic code can be utilized. Moreover, polypeptide variants in which less than about 50, less than 40, less than 30, less than 20, less than 10, or 5-50, 5-25, 5-10, 1-5, or 1-2 amino acids are substituted, deleted, or added in any combination can also be utilized. Polynucleotide variants can be produced for a variety of reasons, e.g., to optimize codon expression for a particular host (change codons in the human mRNA to those preferred by a host, such as, yeast or E. coli as described above).

In other embodiments, the therapeutic protein moiety, i.e., ligand moiety, has conservative substitutions compared to the wild-type sequence. By "conservative substitutions" is intended swaps within groups such as replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. Guidance concerning how to make phenotypically silent amino acid substitutions is provided, for example, in Bowie of al., "Deciphering the Message in Protein Sequences: Tolerance to Amino Acid Substitutions," Science 247:1306-1310 (1990). In specific embodiments, the polypeptides of the invention comprise, or alternatively, consist of, fragments or variants of the amino acid sequence of a therapeutic protein described herein and/or serum transferrin, and/modified transferrin protein of the invention, wherein the fragments or variants have 1-5, 5-10, 5-25, 5-50, 10-50 or 50-150 amino acid residue additions, substitutions, and/or deletions when compared to the reference amino acid sequence. In further embodiments, the amino acid substitutions are conservative. Nucleic acids encoding these polypeptides are also encompassed by the invention.

The modified fusion proteins of the present invention can be composed of amino-acids joined to each other by peptide bonds or modified peptide bonds and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature.

Modifications can occur anywhere in a polypeptide, including the peptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from postranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, glycosylation, GPI anchor formation, hydroxylation, iodination, methylation, myristylation, oxidation, pegylation, proteolytic processing, phosphorylation, prenylation, racemization, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al. (1990) Meth. Enzymol. 182:626-646; Rattan et al., Ann. N.Y. Acad. Sci. 663:48-62.

Therapeutic molecules that may be used as ligand moieties include, but are not limited to, hormones, matrix proteins, immunosuppressants, bronchodilators, cardiovascular agents, enzymes, CNS agents, neurotransmitters, receptor proteins or peptides, growth hormones, growth factors, antiviral peptides, fusogenic inhibitor peptides, cytokines, lymphokines, monokines, interleukins, colony stimulating factors, differentiation factors, angiogenic factors, receptor ligands, cancer-associated proteins, antineoplastics, viral peptides, antibiotic peptides, blood proteins, antagonist proteins, transcription factors, anti-angiogenic factors, antagonist proteins or peptides, receptor antagonists, antibodies, single chain antibodies and cell adhesion molecules. Different therapeutic molecules may be combined into a single fusion protein to produce a bi or multi-functional therapeutic molecule. Different molecules may also be used in combination to produce a fusion protein with a therapeutic entity and a targeting entity. Therapeutic molecules can be fused directly to the stalk moiety of the present invention or, alternatively, fused to or inserted into a presenter moiety, such as a Tf moiety or albumin moiety.

Cytokines are soluble proteins released by cells of the immune system, which act nonenzymatically through specific receptors to regulate immune responses. Cytokines resemble hormones in that they act at low concentrations bound with high affinity to a specific receptor. The term "cytokine" is used herein to describe naturally occurring or recombinant proteins, analogs thereof, and fragments thereof which elicit a specific biological response in a cell which has a receptor for that cytokine. Cytokines preferably include interleukins such as interleukin-2 (IL-2) (GenBank Acc. No. S77834), IL-3 (GenBank Acc. No. M14743), IL-4 (GenBank Acc. No. M23442), IL-5 (GenBank Acc. No. J03478), IL-6 (GenBank Acc. No. M14584), IL-7 (GenBank Acc. No. NM_000880), IL-10 (GenBank Acc. No. NM_000572), IL-12 (GenBank Acc. No. AF180562 and GenBank Acc. No. AF180563), IL-13 (GenBank Acc. No. U10307), IL-14 (GenBank Acc. No. XM_170924), IL-15 (GenBank Acc. No. X91233), IL-16 (GenBank Acc. No. NM_004513), IL-17 (GenBank Acc. No. NM_002190) and IL-18 (GenBank Acc. No. NM_001562), hematopoietic factors such as granulocyte-macrophage colony stimulating factor (GM-CSF) (GenBank Acc. No. X03021), granulocyte colony stimulating factor (G-CSF) (GenBank Acc. No. X03656), platelet activating factor (GenBank Acc. No. NM_000437) and erythropoietin (GenBank Acc. No. X02158), tumor necrosis factors (TNF) such as TNFα (GenBank Acc. No. X02910), lymphokines such as lymphotoxin-α (GenBank Acc. No. X02911), lymphotoxin-β (GenBank Acc. No. L11016), leukoregulin, macrophage migration inhibitory factor (GenBank Acc. No. M25639), and neuroleukin (GenBank Acc. No. K03515), regulators of metabolic processes such as leptin (GenBank Acc. No. U43415), interferons such as interferon α (IFNα) (GenBank Acc. No. M54886), IFNβ (GenBank Acc. No. V00534), IFNγ (GenBank Acc. No. J00219), IFNα (Gen- Bank Acc. No. NM_002177), thrombospondin 1 (THBS1) (GenBank Acc. No. NM_003246), THBS2 (GenBank Acc. No. L12350), THBS3 (GenBank Acc. No. L38969), THBS4 (GenBank Acc. No. NM_003248), and chemokines. Preferably, the modified transferrin-cytokine fusion protein of the present invention displays cytokine biological activity.

The term "hormone" is used herein to describe any one of a number of biologically active substances that are produced by certain cells or tissues and that cause specific biological changes or activities to occur in another cell or tissue located elsewhere in the body. Hormones preferably include proinsulin (GenBank Acc. No. V00565), insulin (GenBank Acc. No. NM_000207), growth hormone 1 (GenBank Acc. No. V00520), growth hormone 2 (GenBank Acc. No. F006060), growth hormone release factor (GenBank Acc. No. NM_021081), insulin-like growth factor I (GenBank Acc. No. M27544), insulin-like growth factor II (GenBank Acc. No. NM_000612), insulin-like growth factor binding protein 1 (IGFBP-1) (GenBank Acc. No. M59316), IGFBP-2 (GenBank Acc. No. X16302), IGFBP-3 (GenBank Acc. No. NM_000598), IGFBP-4 (GenBank Acc. No. Y12508), IGFBP-5 (GenBank Acc. No. M65062), IGFBP-6 (GenBank Acc. No. NM_002178), IGFBP-7 (GenBank Acc. No. NM_001553), chorionic gonadotropin (3 chain (GenBank Acc. No. NM_033142), chorionic gonadotropin a chain (GenBank Acc. No. NM_000735), luteinizing hormone β (GenBank Acc. No. X00264), follicle-stimulating hormone β (GenBank Acc. No. NM_000510), thyroid-stimulating hormone β (GenBank Acc. No. NM_000549), prolactin (GenBank Acc. No. NM_000948), pro-opiomelanocortin (GenBank Acc. No. V01510), corticotropin (ACTH), β-lipotropin, α-melanocyte stimulating hormone (α-MSH), γ-lipotropin, β-MSH, β-endorphin, and corticotropin-like intermediate lobe peptide (CLIP).

The term "hormone" also includes Glucagon-Like Peptide-1 (GLP-1) which is a gastrointestinal hormone that regulates insulin secretion belonging to the so-called enteroinsular axis as well as exendin (e.g., exendin-4 and variants thereof) which is a GLP-1 receptor agonist.

The term "growth factor" is used herein to describe any protein or peptide that binds to a receptor to stimulate cell proliferation. Growth factors preferably include platelet-derived growth factor-α (PDGF-α) (GenBank Acc. No. X03795), PDGF-β (GenBank Acc. No. X02811), steroid hormones, epidermal growth factor (EGF) (GenBank Acc. No. NM_001963), fibroblast growth factors such as fibroblast growth factor 1 (FGF1) (GenBank Acc. No. NM_000800), FGF2 (GenBank Acc. No. NM_002006), FGF3 (GenBank Acc. No. NM_005247), FGF4 (GenBank Acc. No. NM_002007), FGF5 (GenBank Acc. No. M37825), FGF6 (GenBank Acc. No. X57075), FGF7 (GenBank Acc. No. NM_002009), FGF8 (GenBank Acc. No. AH006649), FGF9 (GenBank Acc. No. NM_002010), FGF10 (GenBank Acc. No. AB002097), FGF11 (GenBank Acc. No. NM_004112), FGF12 (GenBank Acc. No. NM_021032), FGF13 (GenBank Acc. No. NM_004114), FGF14 (GenBank Acc. No. NM_004115), FGF16 (GenBank Acc. No. AB009391), FGF17 (GenBank Acc. No. NM_003867), FGF18 (GenBank Acc. No. AF075292), FGF19 (GenBank Acc. No. NM_005117), FGF20 (GenBank Acc. No. NM_019851), FGF21 (GenBank Acc. No. NM_019113), FGF22 (GenBank Acc. No. NM_020637), and FGF23 (GenBank Acc. No. NM_020638), angiogenin (GenBank Acc. No. M11567), brain-derived neurotrophic factor (GenBank Acc. No. M61176), ciliary neurotrophic growth factor (GenBank Acc. No. X60542), transforming growth factor-α (TGF-α) (GenBank Acc. No. X70340), TGF-(3 (GenBank Acc. No. X02812), nerve growth factor-α (NGF-α) (GenBank Acc. No. NM_010915), NGF-β (GenBank Acc. No. X52599), tissue inhibitor of metalloproteinase 1 (TIMP1) (GenBank Acc. No. NM_003254), TIMP2 (GenBank Acc. No. NM_003255), TIMP3 (GenBank Acc. No. U02571), TIMP4 (GenBank Acc. No. U76456) and macrophage stimulating 1 (GenBank Acc. No. L11924).

The term "matrix protein" is used herein to describe proteins or peptides that are normally found in the extracellular matrix. These proteins may be functionally important for strength, filtration, or adhesion. Matrix proteins preferably include collagens such as collagen I (GenBank Acc. No. Z74615), collagen II (GenBank Acc. No. X16711), collagen III (GenBank Acc. No. X14420), collagen IV (GenBank Acc. No. NM_001845), collagen V (GenBank Acc. No. NM_000393), collagen VI (GenBank Acc. No. NM_058175), collagen VII (GenBank Acc. No. L02870), collagen VIII (GenBank Acc. No. NM_001850), collagen IX (GenBank Acc. No. X54412), collagen X (GenBank Acc. No. X60382), collagen XI (GenBank Acc. No. J04177), and collagen XII (GenBank Acc. No. U73778), laminin proteins such as LAMA2 (GenBank Acc. No. NM_000426), LAMA3 (GenBank Acc. No. L34155), LAMA4 (GenBank Acc. No. NM_002290), LAMB1 (GenBank Acc. No. NM_002291), LAMBS (GenBank Acc. No. L25541), LAMC1 (GenBank Acc. No. NM_002293), nidogen (GenBank Acc. No. NM_002508), α-tectorin (GenBank Acc. No. NM_005422), β-tectorin (GenBank Acc. No. NM_058222), and fibronectin (GenBank Acc. No. X02761).

The term "blood proteins" are traditionally defined as those sourced from plasma, many now commonly produced by recombinant means, and include, but are not limited to native serum proteins, derivatives, fragments and mutants or variants thereof, blood clotting factors, derivatives, mutants, variants and fragments (including factors VII, VIII, IX, X), protease inhibitors (antithrombin 3, alpha-1 antitrypsin), urokinase-type plasminogen activator, immunoglobulins, von Willebrand factor and von Willebrand mutants, fibronectin, fibrinogen, thrombin and hemoglobin.

The term "enzyme" is used herein to describe any protein or proteinaceous substance which catalyzes a specific reaction without itself being permanently altered or destroyed. Enzymes preferably include coagulation factors such as F2 (GenBank Acc. No. XM_170688), F7 (GenBank Acc. No. XM_027508), F8 (GenBank Acc. No. XM_013124), F9 (GenBank Acc. No. NM_000133), F10 (GenBank Acc. No. AF503510) and others, matrix metalloproteinases such as matrix metalloproteinase I (GenBank Acc. No. MMP1) (GenBank Acc. No. NM_002421), MMP2 (GenBank Acc. No. NM_004530), MMP3 (GenBank Acc. No. NM_002422), MMP7 (GenBank Acc. No. NM_002423), MMP8 (GenBank Acc. No. NM_002424), MMP9 (GenBank Acc. No. NM_004994), MMP10 (GenBank Acc. No. NM_002425), MMP12 (GenBank Acc. No. NM_002426), MMP13 (GenBank Acc. No. X75308), MMP20 (GenBank Acc. No. NM_004771), adenosine deaminase (GenBank Acc. No. NM_000022), mitogen activated protein kinases such as MAPK3 (GenBank Acc. No. XM_055766), MAP2K2 (GenBank Acc. No. NM_030662), MAP2K1 (GenBank Acc. No. NM_002755), MAP2K4 (GenBank Acc. No. NM_003010), MAP2K7 (AF013588), and MAPK12 (NM_002969), kinases such as JNKK1 (GenBank Acc. No. U17743), JNKK2 (GenBank Acc. No. AF014401), JAK1 (M64174), JAK2 (NM_004972), and JAK3 (NM_000215), and phosphatases such as PPM1A (GenBank Acc. No. NM_021003) and PPM1D (GenBank Acc. No. NM_003620).

The term "transcription factors" is used herein to describe any protein or peptide involved in the transcription of protein-coding genes. Transcription factors may include Sp1, Sp2 (GenBank Acc. No. NM_003110), Sp3 (GenBank Acc. No. AY070137), Sp4 (GenBank Acc. No. NM_003112) NFYB (GenBank Acc. No. NM_006166), Hap2 (GenBank Acc. No. M59079), GATA-1 (GenBank Acc. No. NM_002049), GATA-2 (GenBank Acc. No. NM_002050), GATA-3 (GenBank Acc. No. X55122), GATA-4 (GenBank Acc. No. L34357), GATA-5, GATA-6 (GenBank Acc. No. NM_005257), FOG2 (NM_012082), Eryf1 (GenBank Acc. No. X17254), TRPS1 (GenBank Acc. No. NM_014112), NF-E2 (GenBank Acc. No. NM_006163), NF-E3, NF-E4, TFCP2 (GenBank Acc. No. NM_005653), Oct-1 (GenBank Acc. No. X13403), homeobox proteins such as HOXB2 (GenBank Acc. No. NM_002145), HOX2H (GenBank Acc. No. X16665), hairless homolog (GenBank Acc. No. NM_005144), mothers against decapentaplegic proteins such as MADH1 (GenBank Acc. No. NM_005900), MADH2 (GenBank Acc. No. NM_005901), MADH3 (GenBank Acc. No. NM_005902), MADH4 (GenBank Acc. No. NM_005359), MADH5 (GenBank Acc. No. AF009678), MADH6 (GenBank Acc. No. NM_005585), MADH7 (GenBank Acc. No. NM_005904), MADH9 (GenBank Acc. No. NM_005905), and signal transducer and activator of transcription proteins such as STAT1 (GenBank Acc. No. XM_010893), STAT2 (GenBank Acc. No. NM_005419), STAT3 (GenBank Acc. No. AJ012463), STAT4 (GenBank Acc. No. NM_003151), STAT5 (GenBank Acc. No. L41142), and STAT6 (GenBank Acc. No. NM_003153).

In yet another embodiment of the invention, the therapeutic molecule is a non-human or non-mammalian protein. For example, HIV gp120, HIV Tat, surface proteins of other viruses such as hepatitis, herpes, influenza, adenovirus and RSV, other HIV components, parasitic surface proteins such as malarial antigens, and bacterial surface proteins may be used. These non-human proteins may be used, for example, as antigens, or because they have useful activities. For example, the therapeutic molecule may be streptokinase, staphylokinase, asparaginase, urokinase, or other proteins with useful enzymatic activities.

In an alternative embodiment of the invention, the therapeutic molecule is a ligand-binding protein with biological activity. Such ligand-binding proteins may, for example, (1) block receptor-ligand interactions at the cell surface; or (2) neutralize the biological activity of a molecule in the fluid phase of the blood, thereby preventing it from reaching its cellular target. In some embodiments, the modified transferrin fusion proteins include a modified transferrin molecule fused to a ligand-binding domain of a receptor selected from the group consisting of, but not limited to, a low density lipoprotein (LDL) receptor, an acetylated LDL receptor, a tumor necrosis factor α receptor, a transforming growth factor β receptor, a cytokine receptor, an immunoglobulin Fc receptor, a hormone receptor, a glucose receptor, a glycolipid receptor, and a glycosaminoglycan receptor. In other embodiments, ligand-binding proteins include CD2 (M14362), CD3G (NM_000073), CD3D (NM_000732), CD3E (NM_000733), CD3Z (J04132), CD28 (NM_006139), CD4 (GenBank Acc. No. NM_000616), CDIA (GenBank Acc. No. M28825), CD1B (GenBank Acc. No. NM_001764), CD1C (GenBank Acc. No. NM_001765), CD1D (GenBank Acc. No. NM_001766), CD80 (GenBank Acc. No. NM_005191), GNB3 (GenBank Acc. No. AF501884), CTLA-4 (GenBank Acc. No. NM_005214), intercellular adhesion molecules such as ICAM-1 (NM_000201), ICAM-2 (NM_000873), and ICAM-3 (NM_002162), tumor necrosis factor receptors such as TNFRSF1A (GenBank Acc. No. X55313), TNFR1SFB (GenBank Acc. No. NM_001066), TNFRSF9 (GenBank Acc. No. NM_001561), TNFRSF10B (GenBank Acc. No. NM_003842), TNFRSF11B (GenBank Acc. No. NM_002546), and TNFRSF13B (GenBank Acc. No. NM_006573), and interleukin receptors such as IL2RA (GenBank Acc. No. NM_000417), IL2RG (GenBank Acc. No. NM_000206), IL4R (GenBank Acc. No. AF421855), IL7R (GenBank Acc. No. NM_002185), IL9R (GenBank Acc. No. XM_015989), and IL13R (GenBank Acc. No. 95302). Preferably, the ligand-binding protein fusion of the present invention displays the biological activity of the ligand-binding protein.

The term "cancer-associated proteins" is used herein to describe proteins or polypeptides whose expression is associated with cancer or the maintenance of controlled cell growth, such as proteins encoded by tumor suppressor genes or oncogenes. Cancer-associated proteins may include p16 (GenBank Acc. No. AH005371), p53 (GenBank Acc. No. NM_000546), p63 (GenBank Acc. No. NM_003722), p73 (GenBank Acc. No. NM_005427), BRCA1 (GenBank Acc. No. U14680), BRCA2 (GenBank Acc. No. NM_000059), CTBP interacting protein (GenBank Acc. No. U72066), DMBT1 (GenBank Acc. No. NM_004406), HRAS (GenBank Acc. No. NM_005343), NCYM (GenBank Acc. No. NM_006316), FGR (GenBank Acc. No. NM_005248), myb (GenBank Acc. No. AF104863), raf1 (GenBank Acc. No. NM_002880), erbB2 (GenBank Acc. No. NM_004448), VAV (GenBank Acc. No. X16316), c-fos (V GenBank Acc. No. 01512), c-fes (GenBank Acc. No. X52192), c-jun (GenBank Acc. No. NM_002228), MASI (GenBank Acc. No. M13150), pim-1 (GenBank Acc. No. M16750), TIF1 (GenBank Acc. No. NM_003852), c-fms (GenBank Acc. No. X03663), EGFR (GenBank Acc. No. NM_005228), erbA (GenBank Acc. No. X04707), c-src tyrosine kinase (GenBank Acc. No. XM_044659), c-abl (GenBank Acc. No. M14752), N-ras (GenBank Acc. No. X02751), K-ras (GenBank Acc. No. M54968), jun-B (GenBank Acc. No. M29039), c-myc (GenBank Acc. No. AH001511), RB1 (GenBank Acc. No. M28419), DCC (GenBank Acc. No. X76132), APC (GenBank Acc. No. NM_000038), NF1 (GenBank Acc. No. M89914), NF2 (GenBank Acc. No. Y18000), and bcl-2 (GenBank Acc. No. M13994).

"Fusogenic inhibitor peptides" is used herein to describe peptides that show antiviral activity, anti-membrane fusion capability, and/or an ability to modulate intracellular processes, for instance, those involving coiled-coil peptide structures. Antiviral activity includes, but is not limited to, the inhibition of HIV-1, HIV-2, RSV, SIV, EBV, measles, virus, influenza virus, or CMV transmission to uninfected cells. Additionally, the antifusogenic capability, antiviral activity or intracellular modulatory activity of the peptides merely requires the presence of the peptides and specifically does not require the stimulation of a host immune response directed against such peptides. Antifusogenic refers to a peptide's ability to inhibit or reduce the level of membrane fusion events between two or more moieties relative to the level of membrane fusion which occurs between said moieties in the absence of the peptide. The moieties may be, for example, cell membranes or viral structures, such as viral envelopes or pili. The term "antiviral peptide", as used herein, refers to the peptide's ability to inhibit viral infection of cells or some viral activity required for productive viral infection and/or viral pathogenesis, via, for example, cell-cell fusion or free virus infection. Such infection may involve membrane fusion, as occurs in the case of enveloped viruses, or some other fusion event involving a viral structure and a cellular structure. Fusogenic inhibitor peptides and antiviral peptides often have amino acid sequences that are derived from greater than one viral protein (e.g., an HIV-1, HIV-2, RSV, and SIV-derived polypeptide).

Examples of fusogenic inhibitor peptides and antiviral peptides can be found in WO 94/2820, WO 96/19495, WO 96/40191, WO 01/64013 and U.S. Pat. Nos. 6,333,395, 6,258,782, 6,228,983, 6,133,418, 6,093,794, 6,068,973, 6,060,065, 6,054,265, 6,020,459, 6,017,536, 6,013,263, 5,464,933, 5,346,989, 5,603,933, 5,656,480, 5,759,517, 6,245,737; 6,326,004, and 6,348,568; all of which are herein incorporated by reference.

Examples of other types of peptides, include fragments of therapeutic proteins as described herein, in particular, fragments of human proteins that retain at least one activity of the parent molecule. Peptides that may be used to produce ligand moieties of the invention also include mimetic peptides and peptides that exhibit a biological activity of a therapeutic protein but differ in sequence or three-dimensional structure from a full-length therapeutic protein. As a non-limited example, peptides include erythropoietin mimetic peptides disclosed by Johnson et al. (2000) Nephrol. Dial. Transplant 15(9): 1274-7, Kuai et al. (2000) J. Pept. Res. 56(2):59-62, Barbone et al. (1999) Nephrol. Dial. Transplant. 14 Supp 2:80-4, Middleton et al. (1999) J. Biol. Chem. 274(20):14163-9, Johnson et al. (1998) Biochemistry 37(11): 3699-710, Johnson et al., (1997) Chem. Biol. 12:939-50, Wrighton et al. (1997) Nat. Biotechnol. 15(12):1261-5, Livnah et al., (1996) Science 273:464-71, and Wrighton et al., (1996) Science 273:458-64.

Therapeutic molecules also include allergenic proteins and digested fragments thereof. These include pollen allergens from ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple, elm, etc., dust mites, bee venom, food allergens, animal dander, and other insect venoms.

Other therapeutic molecules include microbial vaccines which include viral, bacterial and protozoal vaccines and their various components such as surface antigens. These include vaccines which contain glycoproteins, proteins or peptides derived from these proteins. Such vaccines are prepared from *Staphylococcus aureus, Streptococcus pyogenes, Streptococcus pneumoniae, Neisseria meningitidis, Neisseria gonorrhoeae, Salmonella* spp., *Shigella* spp., *Escherichia coli, Klebsiella* spp., *Proteus* spp., *Vibrio cholerae, Campylobacter pylori, Pseudomonas aeruginosa, Haemophilus influenzae, Bordetella pertussis, Mycobacterium tuberculosis, Legionella pneumophila, Treponema pallidum,* chlamydia, tetanus toxoid, diphtheria toxoid, influenza viruses, adenoviruses, paramyxoviruses (mumps, measles), rubella viruses, polio viruses, hepatitis viruses, herpes viruses, rabies virus, HIV-1, HIV-2, RSV and papilloma viruses.

Preferred fusion molecules may contain anti-HIV viral peptides, anti-RSV peptides, human growth hormone, α and/or β interferons, erythropoietin (EPO), EPO like peptides, granulocyte-colony stimulating factor (GCSF), granulocyte-macrophage colony-stimulating factor (GMCSF), insulin, insulin-like growth factor (IGF), thrombopoeitin, peptides corresponding to the CDR of an antibody, Islet Neogenesis Associated Protein (INGAP), calcitonin, angiostatin, endostatin, interleukin-2, growth hormone releasing factor, human parathyroid hormone, anti-tumor necrosis factor (TNF) peptides, interleukin-1 (IL-1) receptor and/or single chain antibodies.

Fusion proteins of the invention may also be prepared to include peptides or polypeptides derived from peptide libraries to screen for molecules with new or novel functions. Such peptide libraries may include those commercially or publicly available, e.g., American Peptide Co. Inc., Cell Sciences Inc., Invitrogen Corporation, *Phoenix* Pharmaceuticals Inc., United States Biological, as well as those produced by available technologies, e.g., bacteriophage and bacterial display libraries made using standard procedures.

In yet other embodiments of the invention, fusion proteins may be prepared by using therapeutic protein moieties known in the art and exemplified by the peptides and proteins currently approved by the Food and Drug Administration (≤www.fda.gov/cber/efoi/approve.htm≥) as well as PCT Patent Publication Nos. WO 01/79258, WO 01/77137, WO 01/79442, WO 01/79443, WO 01/79444 and WO 01/79480, all of which are herein incorporated by reference in their entirety.

Table 1 from PCT International Publication No. WO 03/020746, which is herein incorporated by reference, provides a non-exhaustive list of therapeutic proteins that correspond to a therapeutic protein portion, i.e. ligand moiety, of a fusion protein of the invention. The "Therapeutic Protein X" column discloses therapeutic protein molecules followed by parentheses containing scientific and brand names that comprise or alternatively consist of that therapeutic protein molecule or a fragment or variant thereof. "Therapeutic protein X" as used herein may refer either to an individual therapeutic protein molecule (as defined by the amino acid sequence obtainable from the CAS and Genbank accession numbers), or to the entire group of therapeutic proteins associated with a given therapeutic protein molecule disclosed in this column. The 'Exemplary Identifier' column provides Chemical Abstracts Services (CAS) Registry Numbers (published by the American Chemical Society) and/or Genbank Accession Numbers (e.g., Locus ID, NP-XXXXX (Reference Sequence Protein), and XP-XXXXX (Model Protein) identifiers available through the National Center for Biotechnology Information (NCBI) webpage (www.ncbi.nlm.nih.gov) that correspond to entries in the CAS Registry or Genbank database which contain an amino acid sequence of the protein molecule or of a fragment or variant of the therapeutic protein molecule. In addition GenSeq Accession numbers and/or journal publication citations are given to identify the exemplary amino acid sequence for some polypeptides.

The summary pages associated with each of these CAS and Genbank and GenSeq Accession Numbers as well as the cited journal publications are available (e.g., PubMed ID number (PMID)) and are herein incorporated by reference in their entirety. The PCT/Patent Reference column provides U.S. Patent numbers, or PCT International Publication Numbers corresponding to patents and/or published patent-applications that describe the therapeutic protein molecule all of which are herein incorporated by reference in their entirety.

The Biological Activity column describes biological activities associated with the therapeutic protein molecule. The Exemplary Activity Assay column provides references that describe assays which may be used to test the therapeutic and/or biological activity of a therapeutic protein or a transferrin fusion protein of the invention comprising a therapeutic protein X portion. These references are also herein incorporated by reference in their entirety. "The Preferred Indication Y" column describes disease, disorders, and/or conditions that may be treated, prevented, diagnosed, or ameliorated by therapeutic protein X or a transferrin fusion protein of the invention comprising a therapeutic protein X portion. The present invention includes the therapeutic proteins provided in WO 03/020746 which is herein incorporated by reference in its entirety.

EXAMPLES

Example 1

Preparation of GPI Anchor, hMUC1, and mTF Expression Cassette

Figure 3:
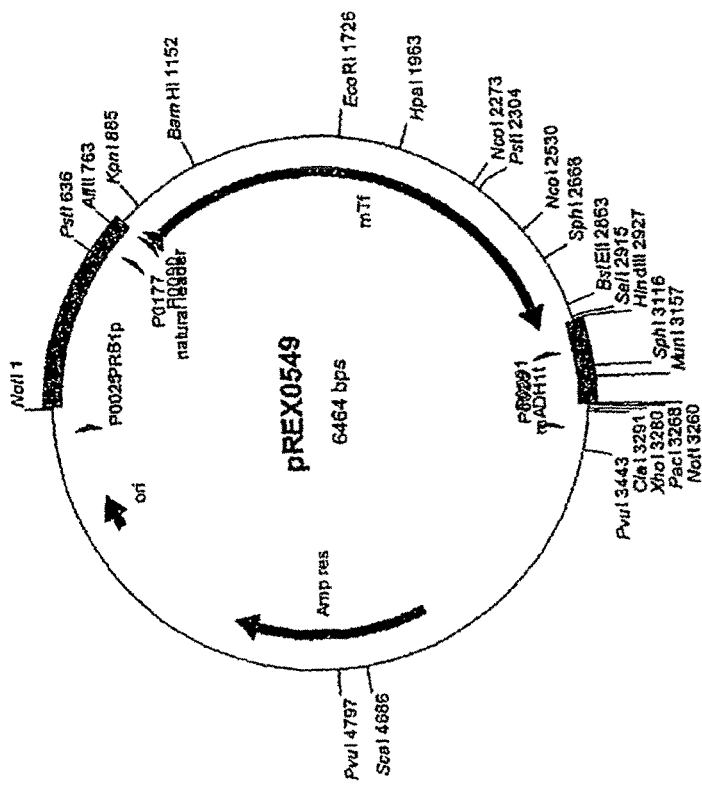
FIG. 3 provides the vector map for pREX0549.

The pREX0549 vector containing a mTf expression cassette (SEQ ID NO: 16) was digested with SalI and HindIII. FIG. 3 provides a vector map for pREX0549. Primers P0922 and P0923 (SEQ ID NO: 7 and SEQ ID NO: 8) were annealed together and ligated into pREX0549 at the SalI/HindIII digestion site. The linker formed by P0922 and P0923 contained SpeI, HindIII, and XbaI restriction sites and was designed to accept a nucleic acid molecule coding for a GPI anchor and MUC1 stalk. The resulting vector, pREX0628, contained the mTf expression cassette with the P0922/P0923 linker.

pREX0628 was digested with HindIII and XbaI. Primers P0924 and P0925 (SEQ ID NO: 9 and SEQ ID NO: 10) were annealed to form the GPI anchor YIR019c. YIR019c was ligated into the digested pREX0628 to create vector pREX0634.

hMUC1 cDNA was RT-PCR amplified from a human breast tumor total RNA library (Clontech) using primers P0958 and P0959 (SEQ ID NO: 11 and SEQ ID NO: 12). The resulting cDNA was amplified with primers P1019 and P1020 (SEQ ID NO: 13 and SEQ ID NO: 14) to create SpeI and HindIII restriction sites. The resulting hMUC1 with SpeI and HindIII sites is provided in SEQ ID NO: 6.

pREX0634 was digested with SpeI and HindIII and the hMUC1 with SpeI and HindIII sites was ligated into the vector. The resulting vector, pREX0663, was used as the display expression cassette (mTf-MUC1-GPI).

pREX0663 was used to create high and low copy number yeast expression vectors. To create a high copy number yeast expression vector, the 4.1 kb display expression cassette was removed from pREX0663 by digesting the vector with NotI. The expression cassette was then ligated into a NotI digested and dephosphorylated pSAC35 vector, resulting in vector pREX0667 (Yeast Display Vector I).

A low copy number yeast expression vector was created by digesting pREX0663 with NotI and ligating the expression vector into a NotI digested and dephosphorylated pREX0699, resulting in pREX0721 yeast display (Yeast Display Vector II).

The yeast expression vectors described above can be used to transform yeast cells and bacterial cells as known in the art. The vector can be expressed in yeast as is known in the art. Further, a collection of expressed transferrin fusion proteins capable of displaying a library of ligand moieties such as random peptides or CDRs can be created and used to screen for binding agents as known in the art.

Example 2

15-mer Random Library Construction

For selection of transferrin variants with novel binding characteristics, a random 15-mer library was constructed in the 289-290 amino acid position of transferrin through a PCR knitting procedure known in the art (see Martin and Smith (2006) Biochem J. 396(2): 287-95). A 15-mer library was designed even though only about 7 amino acids are usually needed to form a binding epitope, and a library of ~$10^9$ only covers a small fraction of the designed library ($3.3 \times 10^{19}$). However, with a library size of $10^9$, a 15-mer library covers 6.4 times more 7-mers than a 7-mer library of the same size.

After obtaining DNA fragment containing BamHI/BspEI sequence of transferrin using P1174/P1227, two PCR reactions (each with a single primer—P1172 and P1173) were performed to obtain single strand DNAs. The ssDNAs were isolated and annealed to form a knitting 15-mer library. This operation ensured that the library maintained the original complexity of the synthetic oligonucleotide. The double strand knitting 15-mer library was further amplified using P1174/P1227 to obtain sufficient quantity of DNA. The PCR product was purified, digested with BamHI/BspEI and cloned into proper plasmid vectors, e.g., pREX0995 (FIG. 4) or pREX0667.

P1172

(SEQ ID NO.: 19)
289-290 15 mer random peptide lib insertion knitting forward back fragment
C CAA CTA TTC AGC TCT CCT 567 567 567 567 567 567 567 567 567 567 567 567 567 567 567 CAT GGG

AAG GAC CTG CTG TTT AAG

In order to introduce randomness in each position in the DNA sequence, a mixture of nucleotides (A, G, T and C) was incorporated into the position at a predetermined ratio according to LaBean and Kauffman (1993) Protein Sci. 2: 1249-54. The mixture indicated below minimizes stop codon frequency and match amino acid composition to natural proteins.

| | |
|---|---|
| 5 | 13% T, 32% G, 20% C, 35% A |
| 6 | 24% T, 24% G, 22% C, 30% A |
| 7 | 37% T, 26% G, 37% C |

P1173

(SEQ ID NO.: 20)
289-290 15 mer random peptide lib knitting back primer for front fragment
AGGAGAGCTGAATAGTTGG -continued P1174
(SEQ ID NO.: 21)
289-290 15 mer random peptide lib knitting
forward primer for front fragment
CTGGATGCAGGTTTGGTGTATG P1227
(SEQ ID NO.: 22)
289-290 15 mer random peptide lib knitting
back primer for back fragment
TCATGATCTTGGCGATGCAGTC Example 3

Selection of Yeast Cells Displaying Flag

Figure 6:
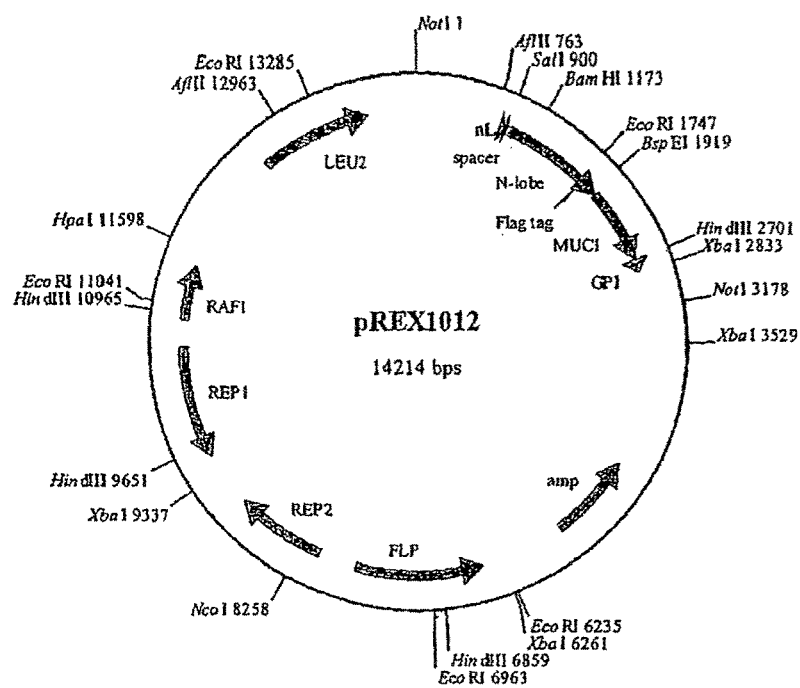
FIG. 6 provides the vector map for pREX1012.

A yeast display system was established whereby the N-lobe of transferrin was displayed on the surface of yeast by fusion to a stalk region, huMUC1, and a GPI signal sequence. To demonstrate the utility of this system in binder selection, a Flag-tag sequence, DYKDDDDK (SEQ ID NO.: 23), or a random 15-mer peptide library was inserted at amino acid position 289 of the transferrin N-lobe. Yeast displaying the Flag-tagged transferrin N-lobe, pREX1012 (FIG. 6), were then spiked into a pool of yeast displaying the transferrin N-lobe with random 15-mer peptides. From this mixed population only yeast displaying the Flag-tagged transferrin N-lobe were recovered by selection with an anti-Flag antibody.

Figure 4:
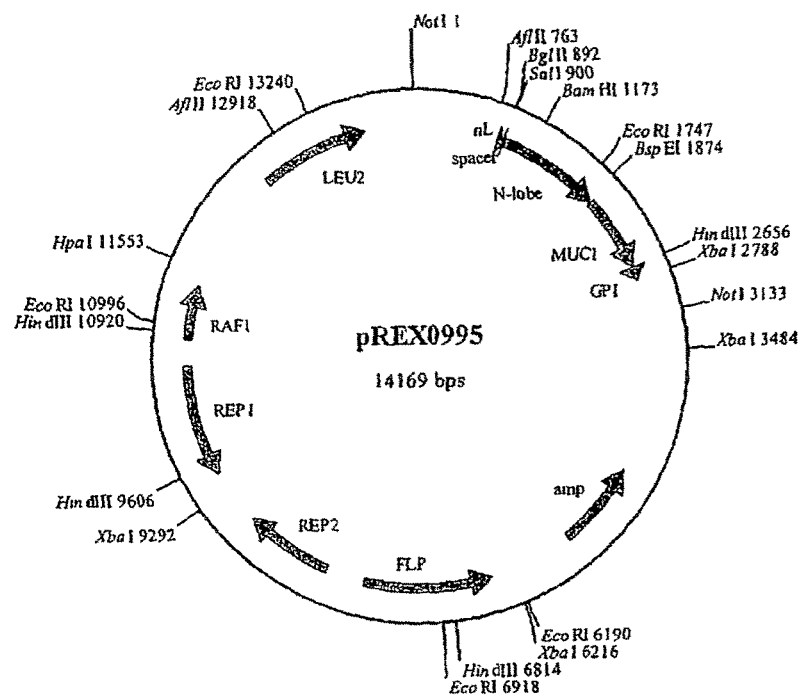
FIG. 4 provides the vector map for pREX0995.
Figure 5:
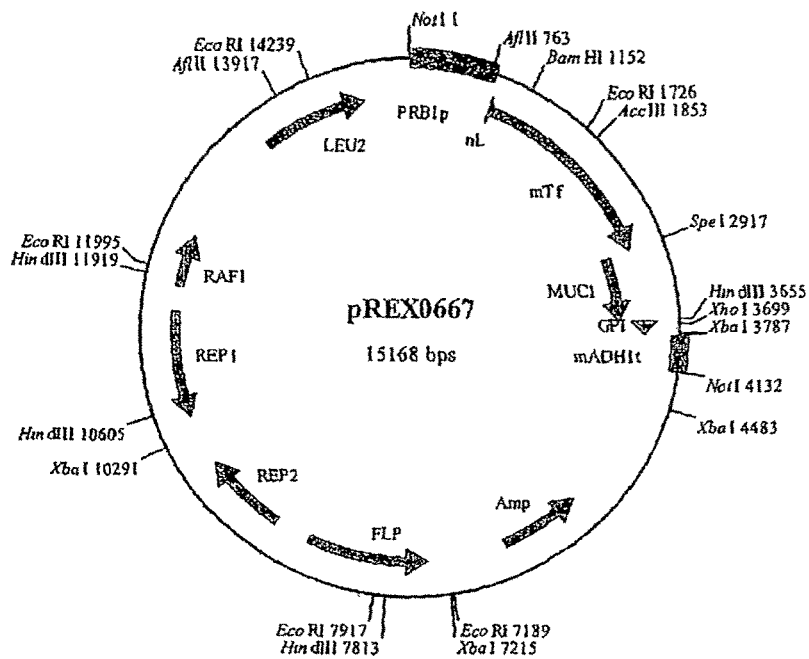
FIG. 5 provides the vector map for pREX0667.
Figure 7:
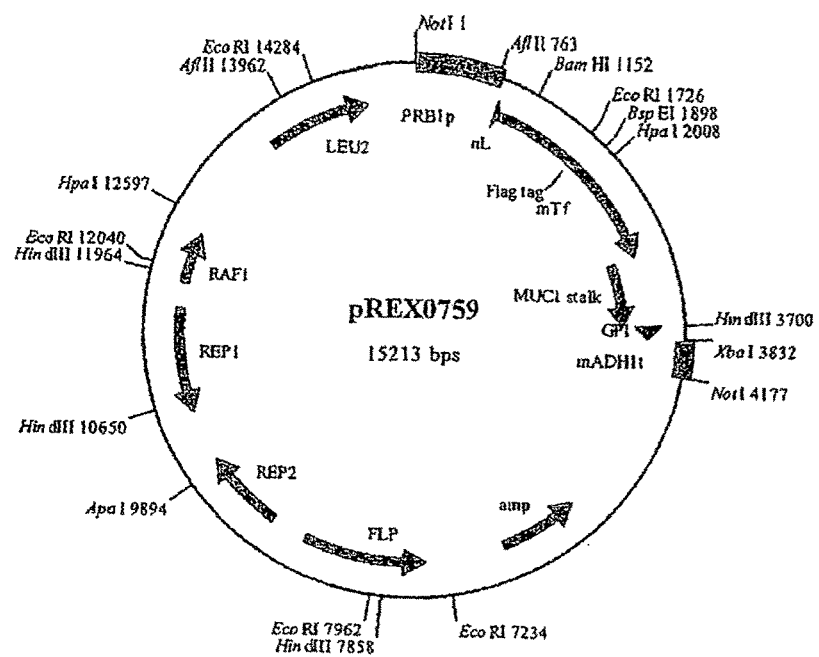
FIG. 7 provides the vector map for pREX0759.

To insert the Flag tag sequence into amino acid position 289 of transferrin, oligos incorporating the Flag tag sequence were synthesized and PCR knitted into pREX0667 vector to generate pREX0759 (FIG. 7). The BamHI/BspEI fragment of pREX0759 containing the Flag tag sequence was then used to replace the same restriction fragment of pREX0995 (FIG. 4). The resulting plasmid, pREX1012, expresses Flag-tagged transferrin N-lobe-MUC1-GPI fusion protein.

The 15-mer library was also cloned between the BamHI/BspEI sites of pREX0995. The preparation of the 15-mer library is described below. The ligation sample was transformed into *E. coli* DH5α, and the transformation mixture was all plated onto 2 LB/Amp (50 µg/mL) agar plates. All colonies were collected and plasmid DNA was extracted using a Qiagen plasmid prep protocol using several miniprep columns.

Plasmid DNA for both pREX1012 and the 15-mer library were transformed into the *Saccharomyces cerevisiae* strain DS1101 cir°. A single colony of pREX1012 was inoculated into Buffered Minimal Medium with Sucrose (BMM/S) and cultured overnight. All colonies of the 15-mer library were collected and inoculated BMM/S. The cell counts of the two overnight cultures were determined by heamocytometer and the following cell mixtures prepared:

(A) $10^3$ pREX1012 yeast cells mixed with $10^9$ 15-mer library yeast cells (10:$10^7$)
(B) $10^3$ pREX1012 yeast cells mixed with $10^8$ 15-mer library yeast cells (100:$10^7$)

The cell mixtures were incubated in 1 ml cell block solution (1×PBS/0.05% Tween-20, 1% BSA) on ice for 30 minutes. After centrifugation (30 seconds at 13000 rpm), the cell pellets were suspended in 1 ml wash solution (1×PBS, 0.5% BSA, 2 mM EDTA) with biotinylated anti-Flag antibody (Sigma Aldrich, 1:25 dilution) and incubate on ice for 30 minutes. The cells were washed twice with 1 ml wash solution and suspended in 800 µl (A) or 160 µl (B) of block solution. To the cell suspensions 200 µl (A) or 40 µl (B) of streptavidin MACS microbeads (Miltenyi Biotec) were added and incubated on ice for 30 minutes. Labeled cells were separated from unlabeled cells using a MS column according to the manufacturer's instructions (Miltenyi Biotec). The labeled cells were collected and plated onto BMM/S agarose plates and incubated at 30° C. until small colonies appeared.

Figure 8:
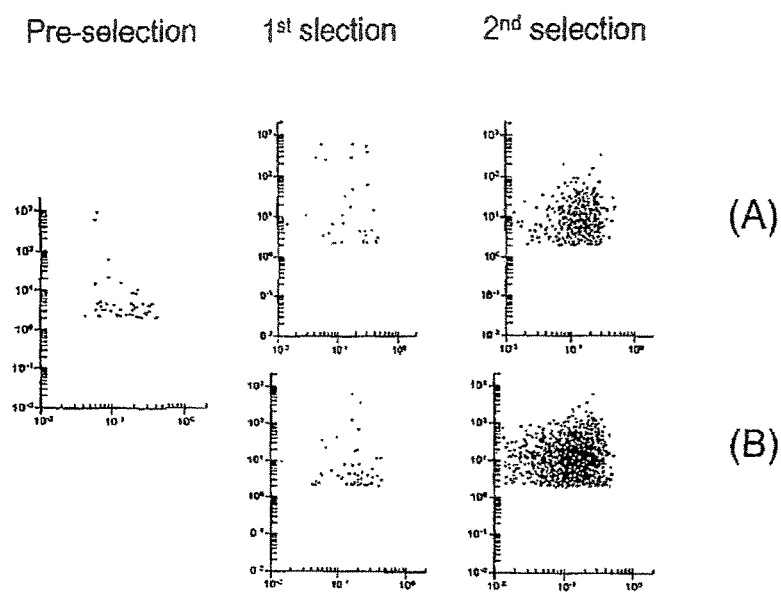
FIG. 8 shows the presence of Flag-tagged yeast after two rounds of MACS® separation.

A second round of selection was performed by collecting all the colonies from each plate and growing them overnight at 30° C. in 5 ml BMM/S. From these cultures cells equivalent to 1.5 $OD_{600}$ were subjected to a further round of MACS separation as described above. The cells from this second round of screening were cultured overnight at 30° C. in 5 ml BMM/S. Yeast cell cultures before and after each selection were analyzed by FACS using anti-Flag monoclonal antibody (Sigma Aldrich) and APC labeled-Goat anti-mouse detection antibody in a Bioanalyzer from Agilent Technolgy. The FACS analysis was performed according to the manufacturer's instructions. The presence of Flag-tagged yeast became apparent after two rounds of MACS separation (FIG. 8)

Example 4

Aga1 Stalk Display

The DNA sequence for the core region of the yeast gene AGA/(residues 116-658 of the mature protein) was obtained through PCR of S288c yeast genomic DNA using the following primers:

(a)
(SEQ ID NO.: 24)
CAGATCTAGAACAACCGCTATCAGCTCATTATCC (b)
(SEQ ID NO.: 25)
CAGAAAGCTTAGTAGTGGAAACTTCTGTAGTG

Figure 9:
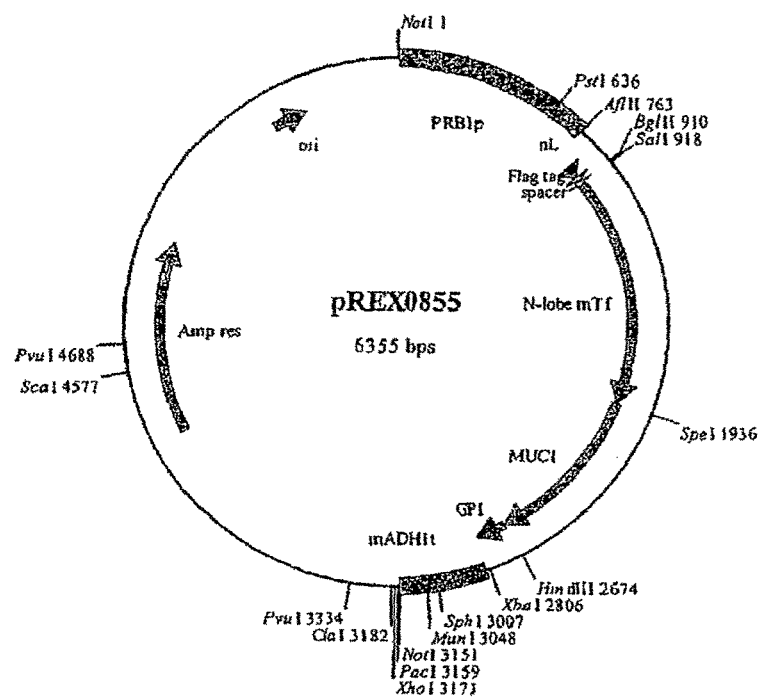
FIG. 9 provides the vector map for pREX0855.

AGA1 (partial sequence)
(SEQ ID NO.: 74)
ACAACCGCTATCAGCTCATTATCCGAAGTAGGAACTACAACCGTGG
TATCATCCAGCGCCATTGAACCATCAAGTGCCTCTATAATCTCACC
TGTCACCTCTACACTTTCGAGTACAACATCGTCCAATCCAACTACT
ACCTCCCTAAGTTCGACATCTACATCTCCAAGCTCTACATCTACAT
CTCCAAGCTCTACATCTACCTCATCAAGTTCGACATCTACCTCATC
AAGTTCGACATCTACCTCATCAAGTTCGACATCTACATCTCCAAGT
TCGACATCCACATCTTCAAGTTTGACATCCACATCTTCAAGTTCTA
CATCTACATCCCAAAGTTCTACATCTACCTCATCAAGTTCGACATC
TACATCTCCAAGCTCTACATCTACCTCATCAAGTTCAACATCTACA
TCTCCAAGTTCTAAATCTACTTCTGCAAGCTCCACTTCCACTTCTT
CATATTCAACATCTACATCCCCAAGTTTGACTTCTTCATCTCCAAC
TTTGGCTTCCACTTCTCCAAGTTCAACATCTATTAGCTCTACTTTT
ACTGATTCAACTTCATCCCTTGGCTCCTCTATAGCATCTTCATCAA
CGTCTGTGTCATTATACAGCCCATCCACACCTGTTTACTCCGTCCC
TTCGACTTCGTCAAATGTTGCAACTCCTTCTATGACTTCTTCAACT
GTTGAAACAACTGTTAGTTCACAAAGTTCGTCTGAATATATCACCA
AATCCTCAATTTCTACTACTATCCCATCATTTTCCATGTCTACATA
TTTCACCACTGTTAGTGGAGTCACTACAATGTATACGACATGGTGT
CCTTATAGCTCTGAATCTGAGACTAGCACATTAACCAGTATGCATG
AAACGGTTACAACAGACGCTACAGTCTGCACTCACGAGTCTTGCAT
GCCCTCGCAGACAACAAGTTTGATTACATCTTCTATAAAAATGTCC
ACTAAAAACGTCGCAACTTCTGTAAGCACCTCAACGGTTGAATCCT
CATATGCATGCTCCACATGTGCTGAAACGTCACACTCGTATTCTTC
CGTGCAAACAGCTTCATCAAGTTCTGTAACACAGCAGACCACATCC
ACAAAGAGTTGGGTAAGTTCAATGACAACTTCGGATGAAGATTTCA
ATAAGCACGCTACCGGTAAGTATCATGTAACATCTTCAGGTACCTC
AACCATTTCGACTAGTGTAAGTGAAGCCACGAGTACATCAAGCATT
GACTCAGAATCTCAAGAACAATCATCACACTTATTATCGACATCGG
TCCTTTCATCCTCCTCCTTGTCTGCTACATTATCCTCTGACAGTAC
TATTTTGCTATTCAGTTCTGTATCATCACTAAGTGTCGAACAGTCA
CCAGTTACCACACTTCAAATTTCTTCAACATCAGAGATTTTACAAC
CCACTTCTTCCACAGCTATTCAACAATATCTGCCTCTACATCATC
ACTTTCCGCAACATCTATCTCTACACCATCTACCTCTGTGGAATCG
ACTATTGAATCTTCATCATTGACTCCGACGGTATCTTCTATTTTCC
TCTCATCATCATCTGCTCCCTCTTCTCTACAAACATCTGTTACCAC
TACAGAAGTTTCCACTACT -continued (SEQ ID NO.: 75)
TTAISSLSEVGTTTVVSSSAIEPSSASIISPVTSTLSSTTSSNPTT
TLSLLTSTSPSSTSTSPSSTSTSSSSTSTSSSSTSTSSSSTSTSPS
STSTSSSLTSTSSSSTSTSQSSTSTSSSSTSTSPSSTSTSSSSTST
SPSSKSTSASSTSTSSYSTSTSPSLTSSSPTLASTSPSSTSISSTF
TDSTSSLGSSIASSSTSVSLYSPSTPVYSVPSTSSNVATPSMTSST
VETTVSSQSSSEYITKSSISTTIPSFSMSTYFTTVSGVTTMYTTWC
PYSSESETSTLTSMHETVTTDATVCTHESCMPSQTTSLITSSIKMS
TKNVATSVSTSTVESSYACSTCAETSHSYSSVQTASSSSVTQQTTS
TKSWVSSMTTSDEDFNKHATGKYHVTSSGTSTISTSVSEATSTSSI
DSESQEQSSHLLSTSVLSSSSLSATLSSDSTILLFSSVSSLSVEQS
PVTTLQISSTSEILQPTSSTAIATISASTSSLSATSISTPSTSVES
TIESSSLTPTVSSIFLSSSSAPSSLQTSVTTTEVSTT A PCR product of ~1.5 kb was isolated and digested with XbaI/HindIII. The fragment was ligated in to SpeI/HindIII digested pREX0855 (FIG. 9) and transformed into *E. coli* DH5α. All resulting colonies were collected and plasmid DNA was isolated from the cells. The expression cassette was receovered by NotI digestion and ligated into pSAC35 to give the yeast expression vector.

Transformation into yeast and FACS with anti-Flag antibody as previously described. Yeast colonies showed high level of N-lobe display, approximately 10-fold higher than the comparable MUC1 stalk based construct (data not shown).

Figure 10:
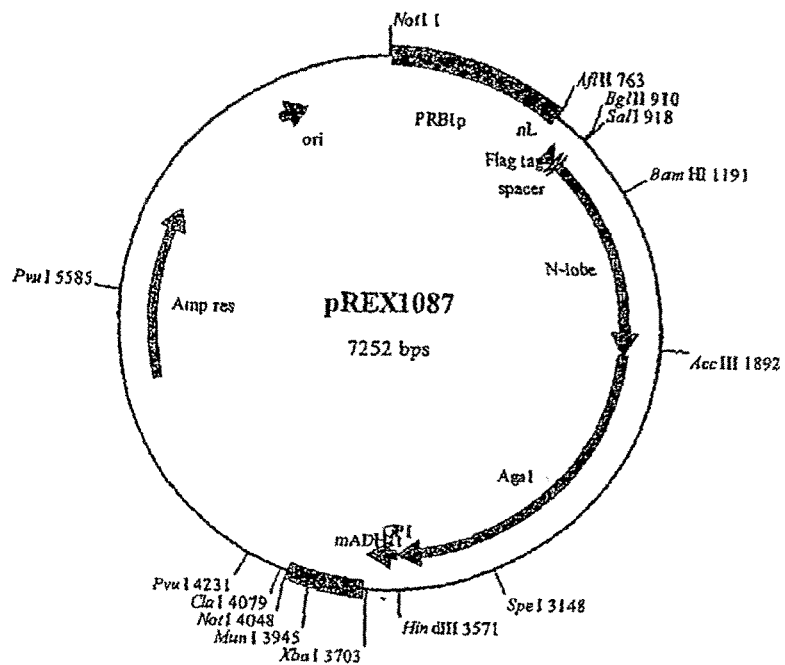
FIG. 10 provides the vector map for pREX1087.
Figure 11:
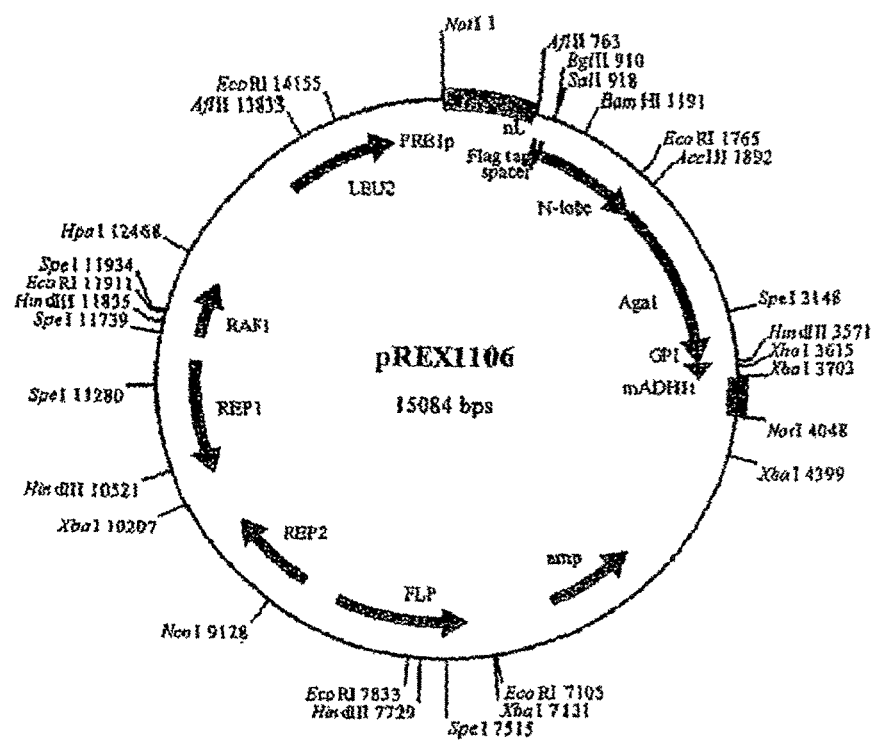
FIG. 11 provides the vector map for pREX1106.

A single yeast colony was isolated and plasmid DNA extracted from this yeast cells. The NotI expression cassette was recovered after NotI digestion of the extracted plasmid DNA and ligated in to NotI digested pREX0855 to give the plasmid pREX1087 (FIG. 10), a pUC-based vector containing Flag-N-lobe-Aga1-GPI expression cassette. A region of the DNA sequence corresponding to Aga1 was sequenced to confirm its identity. This expression cassette was also transferred back in to pSAC35 to give pREX1106 (FIG. 11).

Example 5

Selection of Mammalian GPI Variants that Function in Yeast Cells

Mammalian GPI signals play roles that their yeast counterparts do not play, such as intracellular trafficking, transmission of transmembrane signals and clathrin-independent endocytosis (Biochem J. 1993, 294: 305-324). Yeast cells have not only cell membrane, but cell walls that are absent from mammalian cells, and many of the yeast GPI have unique sequences that target proteins to yeast cell wall (J Bacteriol, 1999, 181:3886-3889). The GPI of human placental alkaline phosphotase has been shown to not function at all in yeast cells (Mol Microbiol 1999, 34:247-256). As a means to obtain novel sequences that can attach expressed recombinant proteins in to a yeast cell wall, a yeast display vector based on pREX0885 (FIG. 9) but using the huMDP GPI sequence (DQLGGSCRTHYGYS S GASSL-HRHWGLLLASLAPLVLCLSLL) (SEQ ID NO: 98). This sequence was modified to incorporate four completely random codons (X) as well as several (underlined) rational modifications, XQXGGSXXTIGGYS GAASSLQR TIGLLLASLAPLVLASLL (SEQ ID NO.: 26), wherein X is any amino acid.

A yeast library expressing the following fusion protein, Flag tag-N-lobe-MUC1 stalk-GPI in which the GPI sequence was modified as described above was transformed into the *Saccharomyces cerevisiae* strain DS1101 cir°. Any yeast cells with the fusion protein attached to the cell wall were isolated through MACS using a biotinylated-anti-Flag antibody.

Two oligos P2035 & P2036 (see below) were annealed and extended using Taq polymerase. The resulting DNA fragment was purified, digested with HindIII/XbaI and ligated in to HindIII/XbaI digested pREX0855 (see below and FIG. 9).

Primers

```
P2035
                                                         (SEQ ID NO.: 27)
CTACAAGCTTNNKCAANNKGGTGGTTCTNNKNNKACTATTGGTGGTTATTCTGGTGCTGCTTCTT
CCTTGCAGAGAACTATTG

P2036
                                                         (SEQ ID NO.: 28)
GATGTCTAGATTATTATAACAAAGAAGCTAAAACCAATGGAGCTAAAGAAGCCAATAACAAACCA
ATAGTTCTCTGCAAGGAAG

HindIII
-+----
aagcttnnkc aannkggtgg ttctnnknnk actattggtg gttattctgg tgctgcttct
ttcgaannmg ttnnmccacc aagannmnnm tgataaccac caataagacc acgacgaaga
 k l x q x    g g s x x t i g g y s g a a s
?+0P2035+22
>>................P2035...............>
                                   P0236<< tccttgcaga gaactattgg tttgttattg gcttctttag ctccattggt tttagcttct
aggaacgtct cttgataacc aaacaataac cgaagaaatc gaggtaacca aaatcgaaga
 s l q r t i   g l l l a s l a p l v l a s
>....P2035.....>>
<.................P2036.................<

XbaI
     -+----
                                                         (SEQ ID NO.: 29)
ttgttataat aatctaga
aacaatatta ttagatct (SEQ ID NO.: 30)
 l l - - s r
<..P2036..<<
```

The ligation mixture was transformed into *E. coli* DH5α to obtain approx. 5×10⁵ colonies. All colonies were collected and plasmid DNA isolated. The plasmid DNA was digested with NotI to recover the expression cassette and cloned into SAC35 to create the yeast expression library. This library was transformed into DS1101 cir° cells by electroporation. An overnight culture of the aforementioned library was subjected to MACS using a biotinylated-anti-Flag antibody. The isolated cells were immediately purified again through MACS with the same antibody. The resulting cells were plated onto BMMS plates and 24 colonies were characterized by FACS and DNA sequencing analysis. (See Flag spike description.)

Of the 22 clones that gave readable sequence only 7 had full length GPI anchors (Table 1) with varying levels of display and the best of which were better than the pREX1003 vector expressing the same fusion protein with a yeast GPI anchor.

TABLE 1

| Clone No. | Sequence | Amino Acids | Display Level |
|---|---|---|---|
|  | NNKCAANNKGGTGGTTCTNNKNNK (SEQ ID NO.: 31) |  |  |
| 23 | TGTCAATAGGGTGGTTCTAGGCCT (SEQ ID NO.: 32) | CysGlnStopGlyGlySerArgPro | 200 |
| 8 | TGTCAAATTGGTGGTTCTTAGTGT (SEQ ID NO.: 33) | CysGlnIleGlyGlySerStopLys (SEQ ID NO.: 34) | 150 |
| 15 | CAGCAATATGGTGGTTCTGTGGAT (SEQ ID NO.: 35) | GluGlnTyrGlyGlySerValAsp (SEQ ID NO.: 36) | 120 |
| 14 | TCTCAAGTTGGTGGTTCTACTTGG (SEQ ID NO.: 37) | SerGlnValGlyGlySerThrTrp (SEQ ID NO.: 38) | 100 |
| 5 | NNKCAANNKGGTGGTTCTNNKNNK (SEQ ID NO.: 39) | Frameshift | 80 |
| 2 | CATCAAGGTGGTGGTTCTATTCGG (SEQ ID NO.: 40) | HisGlnGlyGlyGlySerIleArg (SEQ ID NO.: 41) | 60 |
| 6 | NNKCAANNKGGTGGTTCTNNK NNKCAANNKGGTGGTTCTNNKNNK (SEQ ID NO.: 31) NNK (SEQ ID NO.: 42) | Frameshift | 50 |
| 12 | CATCAATTGGGTGGTTCTGTTACG (SEQ ID NO.: 43) | HisGlnLeuGlyGlySerValThr (SEQ ID NO.: 44) | 50 |
| 18 | TATCAATCGGGTGGTTCTGGGACT (SEQ ID NO.: 45) | TyrGlnSerGlyGlySerGlyThr (SEQ ID NO.: 46) | 50 |
| 13 | GGGCAATATGGTGGTTCTTAGTGG (SEQ ID NO.: 47) | GlyGlnTyrGlyGlySerStopTrp (SEQ ID NO.: 48) | 40 |
| 1 | GTGCAAGCGGGTGGTTCTGATTAG (SEQ ID NO.: 49) | ValGlnAlaGlyGlySerAspStop (SEQ ID NO.: 50) | 30 |
| 4 | TAGCAAATGGGTGGTTCTACTAAG (SEQ ID NO.: 51) | StopGlnMetGlyGlySerTyrLys | 30 |
| 21 | TAGCAAACGGGTGGTTCTTCTTAT (SEQ ID NO.: 52) | StopGlnThrGlyGlySerSerTyr | 20 |
| 3 | AAGCAACGGGGTGGTTCTTAGACT (SEQ ID NO.: 53) | LysGlnProGlyGlySerStopThr (SEQ ID NO.: 54) | 20 |
| 7 | CTGCAATGTGGTGGTTCTTAGTGG (SEQ ID NO.: 55) | LeuGlnLysGlyGlySerStopTrp (SEQ ID NO.: 56) | 15 |
| 16 | TAGCAACTGGGTGGTTCTTTTGGG (SEQ ID NO.: 57) | StopGlnLeuGlyGlySerPheGly | 15 |
| 17 | TAGCAATATGGTGGTTCTGTTCTA (SEQ ID NO.: 58) | StopGlnTyrGlyGlySerValLeu | 15 |
| 19 | CTTCAAGTGGGTGGTTCTTTGTAG (SEQ ID NO.: 59) | LeuGlnValGlyGlySerLeuStop (SEQ ID NO.: 60) | 15 |
| 24 | TAGCAATTTGGTGGTTCTCATGCG (SEQ ID NO.: 61) | StopGlnPheGlyGlySerHisAla | 15 |
| 9 | CGGCAACGGGGTGGTTCTAAGTGG (SEQ ID NO.: 62) | ArgGlnArgGlyGlySerLysTrp (SEQ ID NO.: 63) | Low |

TABLE 1-continued

| Clone No. | Sequence | Amino Acids | Display Level |
|---|---|---|---|
| 20 | TCGCAAACTGGTGGTTCTGTTGCT (SEQ ID NO.: 64) | SerGlnThrGlyGlySerValAla (SEQ ID NO.: 65) | Low |

Figure 12:
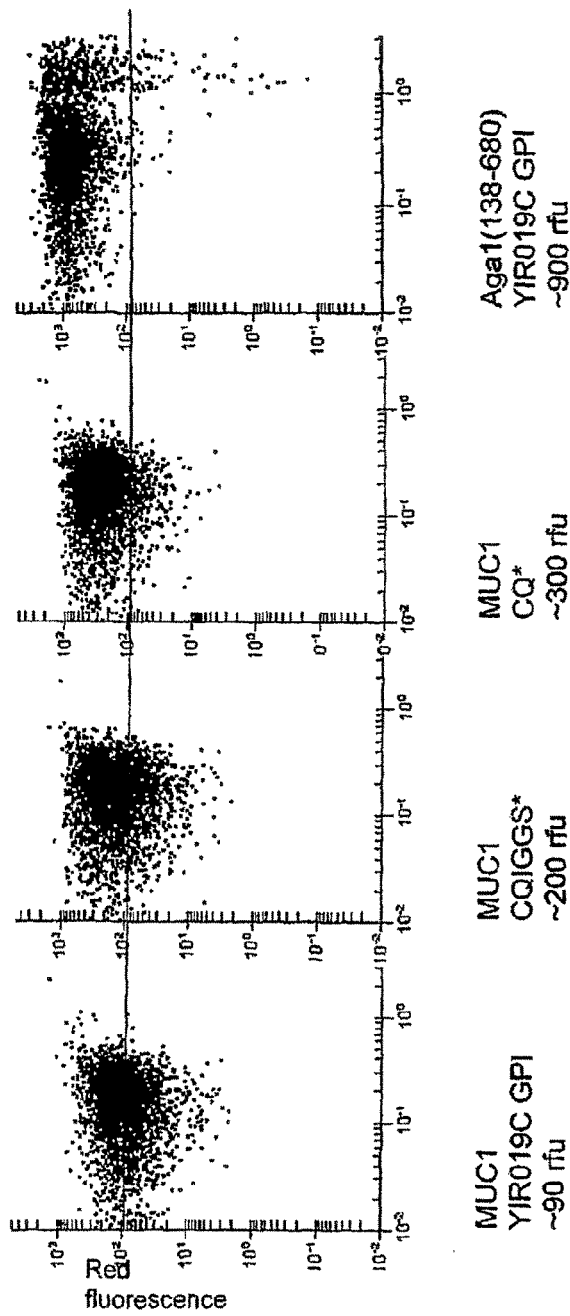
FIG. 12 shows FACS analysis with MUC1 and AGA1.

Unexpectedly, 50% of the clones were truncated by a stop codon in one of the randomized codons effectively deleting the GPI anchor signal. Of these 12 clones, two were determined to have display levels significantly better than pREX1003 and were found to contain a cysteine residue just prior to the stop codon (CQIGGS*(SEQ ID NO.: 34) and CQ* where *=stop codon) (FIG. 12). In all likelihood these construct were crosslinked in to the cell wall via disulphide bonding to a free cysteine residue in a cell wall protein.

Example 6

RGD Library Construction and Screening

For selection of transferrin variants that bind integrin $_{IIb}$ 3 and inhibit platelet aggregation, a library was constructed by inserting peptides comprising three randomized amino acids on either side of the integrin binding sequence Arg-Gly-Asp (RGD) into the Tf scaffold (CXXXRGDXXXC; SEQ ID NO: 77; X representing a randomization position) in the 289-290 amino acid position of Transferrin through a PCR knitting procedure.

Figure 13:
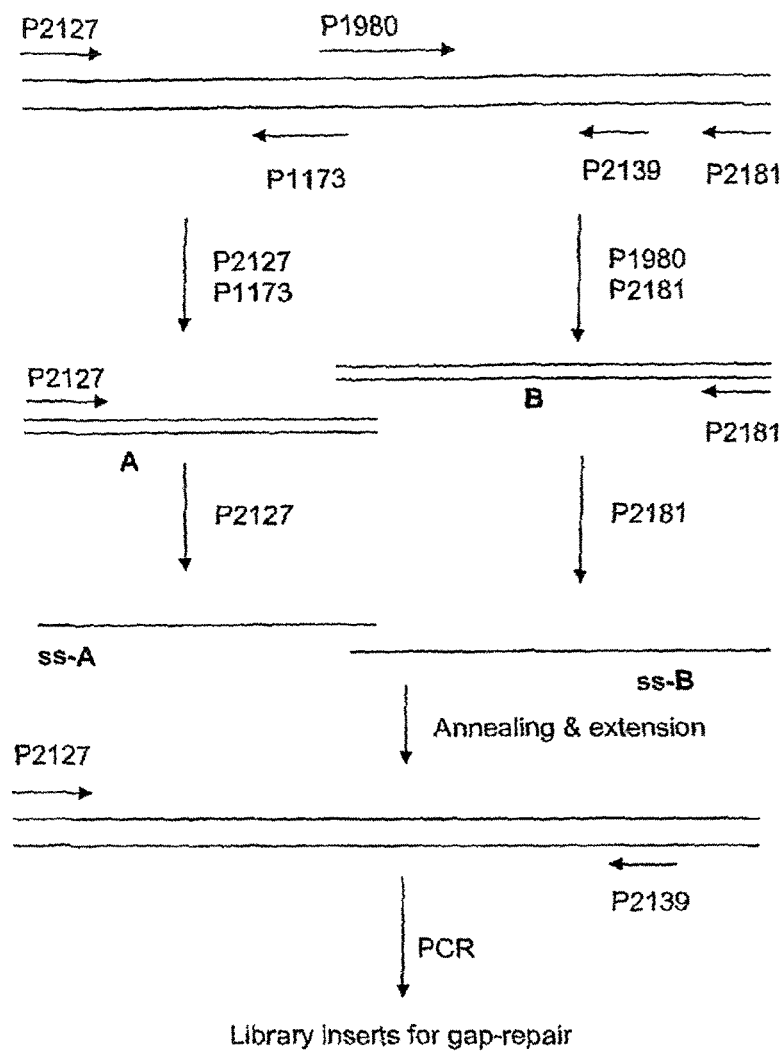
FIG. 13 shows fragments A and B obtained by amplifying pREX 1106 with primers P1980/P2181 and P2127/P1173.

Primers P1980/P2181 and P2127/P1173 were used to amplify pREX1106 (FIG. 11) to obtain fragment A and B (FIG. 13).

```
P1173
289-290 knitting back primer for front fragment
AGGAGAGCTGAATAGTTGG (SEQ ID NO: 78)

P1980
289-290 RGD containing random peptide library
knitting forward primer for back fragment
CCAACTATTCAGCTCTCCTTGT567567567AGAGGAGAC567567
567TGTCATGGGAAGGACCTGCTGTTTAAG (SEQ ID NO: 79)
```

| 5 | 13% T, 32% G, 20% C, 35% A |
| 6 | 24% T, 24% G, 22% C, 30% A |
| 7 | 37% T, 26% G, 37% C |

(Nucleotide mix to minimize stop codon frequency and match amino acid composition to natural protein; Labean, T H and Kauffman, S A, 1993, Protein Science. 2: 1249-1254)

```
P2127
289-290 knitting forward primer for front
fragment
CCTCCTACCTTGATTGCATCAG (SEQ ID NO: 80)

P2181
289-290 knitting back primer for back fragment
GGAGATGAAGAAGTCAAACTTGGG (SEQ ID NO: 81)

P2139
Gap repair GPI lib
GAGGCACTTGATGGTTCAATGG (SEQ ID NO: 82)
```

Primer P1980 introduced the randomized sequence. The amplified DNA fragments were gel purified and further amplified using a single primer (P2181 for fragment A and P2127 for fragment B) to obtain single strand DNA (ss-A and ss-B). ss-A and ss-B were annealed in the presence of dNTP and Klenow enzyme to form a double strand fragment. This annealing product was finally amplified using P2127 and P2139 and gel purified to generate RGD-library inserts. This operation ensured that the library maintained the original complexity of the synthetic oligonucleotide.

The inserts was used to construct a $7\times10^8$ library through gap-repair into BamHI-BspEI digested pREX1106 using the electroporation method provided below. For each gap-repair reaction, 1.4 □g of BamHI/BspEI digested pREX1106 was mixed with 1 □g of the aforementioned RGD-library inserts and electroporated into DS1101 cir° yeast cells.

High Efficiency Electroporation of Yeast (DS1101 cir°) for Library Construction.

1) Inoculate 100 mL of YEP/S (1% w/v yeast extract, 2% w/v peptone, 2% w/v sucrose) to $OD_{600}$=0.2 from a fresh overnight culture of DS1101 cir°.
2) Grow cells at 30° C., 200 rpm to an $OD_{600}$ of 0.8 (about 5 hours).
3) Collect cells by centrifugation at 2,000 rpm for 5 min.
4) Decant the supernatant and resuspend the pellet in 18 mL of TE (10 mM Tris-HCl, pH7.5 and 1 mM EDTA) buffer. Then add 2 mL of 1M Lithium Acetate.
5) Incubate cells at 30° C. in a roller drum for 45 minutes.
6) Add 0.5 mL of 1M DTT.
7) Incubate for 15 minutes at 30° C. in a roller drum.
8) Wash with 80 mL of sterile water at room temperature.
9) Wash the pellet in 100 mL of sterile water at room temperature.
10) Wash the pellet in 10 mL ice-cold 1M sorbitol.
11) Resuspend cells in 60 μL of ice-cold 1M sorbitol (enough for 6 transformations).
12) Keep the cells on ice and mix in sterile microfuge tubes:
　i. 50 μL of competent yeast cells
　ii. 1.4 μg DNA (up to 5 μL)
　iii. 5 μg of ssDNA (0.5 μl 10 mg/mL)
13) Incubate on ice for 5 minutes before pulse. Tap cell/DNA suspension to the bottom of a 0.2 cm ice cold cuvette and pulse once:

| i. | Voltage | 1.5 Kv |
| ii. | Capacitance | 25 □F |
| iii. | Resistance | 200Ω |

14) Immediately add 1 mL of a 50:50 mix of YEP/S and 1M sorbitol, transfer yeast to a microfuge tubes and allow yeast to recover at 30° C. for one hour (May not need to recover, test is needed).
15) Collect cells by centrifugation at 5000 rpm for 1 minute and wash once with 1 mL of 1M sorbitol.
16) Resuspend in 1 mL of 1M sorbitol and spread onto BMM/S plates. Incubate at 30° C.

High affinity Trans-bodies to □$_{IIb}$□3 were selected from the yeast display library on plates coated with integrin purified from human platelets. The purification of $\alpha_{IIb}\beta_3$ integrin was carried out according to Hillman et al. with minor modifications (Hillman et al., 2002, Protein Expr. Purif. 25(3): 494-502). Integrin was diluted (1:30 dilution) in coating buffer (50 mM Borate buffer, pH 9.5) and coated onto a Petridish overnight at 4° C. After rinsing three times with buffer A (20 mM Tris-HCl, pH7.5, 150 mM NaCl, 1 mM $MgCl_2$, 1 mM $CaCl_2$ and 1 mM $MnCl_2$), the plate was blocked for 2 hours at RT with binding buffer+1% BSA. Onto the plate 40 $OD_{600}$ units of overnight yeast RGD library, grown in BMM/S (2% w/v sucrose) at 30° C. 200 rpm, was collected by centrifugation and resuspended in 10 mL binding buffer with 1% BSA and GRGDSP inhibitor peptide (1 $\mu$g/mL for $1^{st}$ selection and 10 $\mu$g/mL for $2^{nd}$ selection), and incubated with coated integrin for 2 hours at RT with gentle shaking. Unbound cells were washed away with 3 washes of binding buffer and bound cells were collected.

Production of Soluble Proteins.

The DNA coding region for the N-lobe containing the RGD sequences was recovered from the yeast display vector and cloned into a yeast expression vector to produce soluble Tf molecules containing the RGD sequences. These were expressed in high cell density fed-batch fermentations and purified by column chromatography. Examples of sequences of selected clones in comparison to the sequences of natural $\alpha_{IIb}\beta_3$ ligands is provided below:

| Library | C | X | X | X | R | G | D | X | X | X | C | |
|---|---|---|---|---|---|---|---|---|---|---|---|---|
| #41 | | N | S | P | | | | T | P | I | | SEQ ID NO: 83 |
| #32 | | I | I | P | | | | R | P | R | | SEQ ID NO: 84 |
| #14 | | Q | G | S | | | | T | P | N | | SEQ ID NO: 85 |
| #16 | | G | F | H | | | | T | P | D | | SEQ ID NO: 86 |
| #34 | | R | Q | H | | | | T | P | A | | SEQ ID NO: 87 |
| #39 | | Y | P | S | | | | F | A | H | | SEQ ID NO: 88 |
| #30 | | N | S | R | | | | V | P | I | | SEQ ID NO: 89 |
| #37 | | H | P | I | | | | T | Y | Y | | SEQ ID NO: 90 |
| Flavoridin | C | R | I | A | | | | F | P | D | D | C | SEQ ID NO: 91 |
| Kistrin | C | R | I | P | | | | M | P | D | D | D | SEQ ID NO: 92 |
| Fibronectin | | V | T | G | | | | S | P | A | | SEQ ID NO: 93 |

(Library row: SEQ ID NO: 77)

Integrin Binding Analysis.

Figure 14:
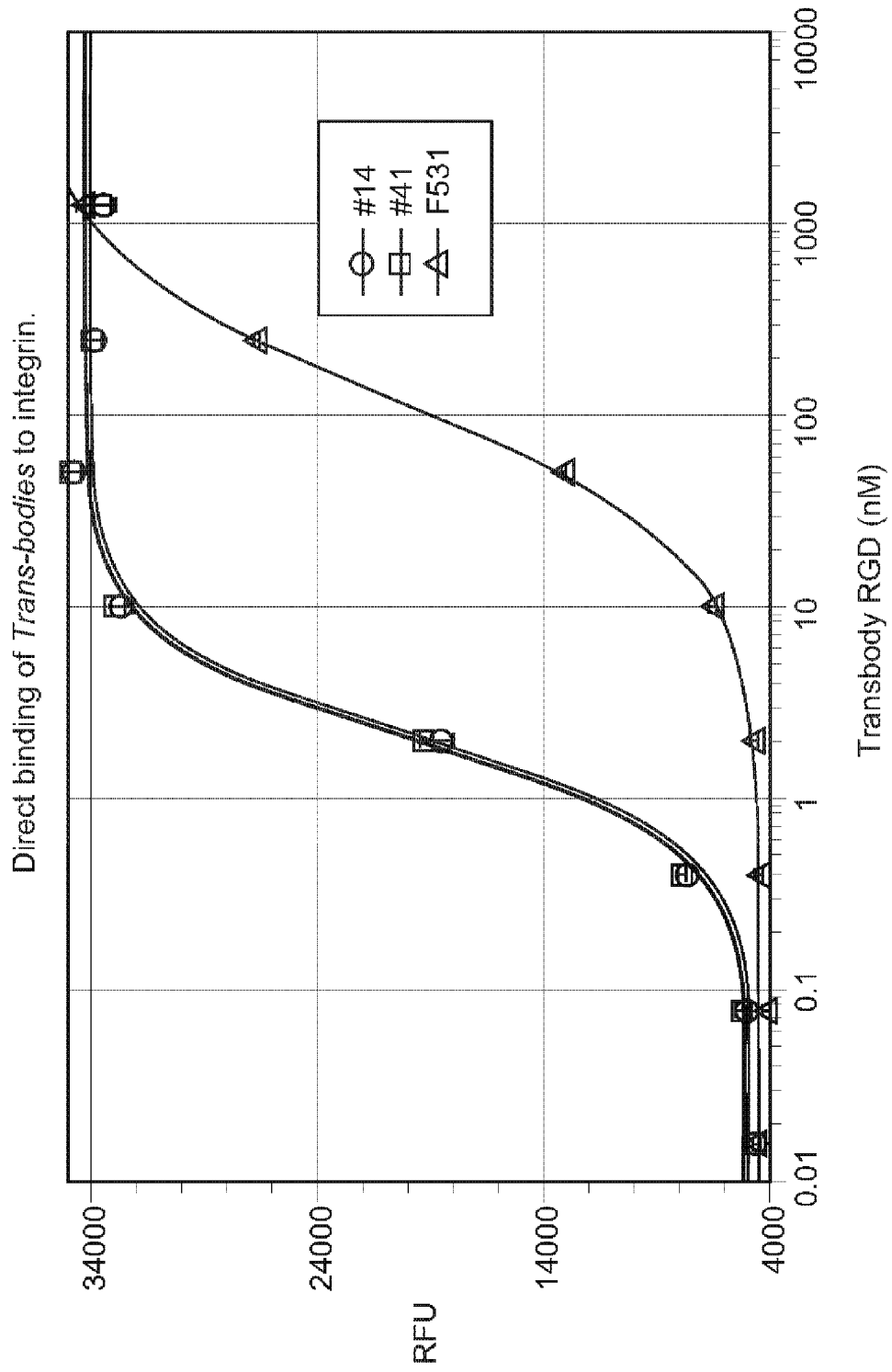
FIG. 14 shows competitive binding analysis of RGD transbody binding in relative florescent units (RFU).

Direct binding of RGD Trans-bodies to integrin was measured by ELISA. Integrin was diluted in coating buffer and coated onto Maxisorb ELISA plates overnight at 4° C. Plates were blocked with buffer A containing 1% BSA and 0.05% Tween-20 (binding buffer) for 2 hr at room temperature with shaking. Trans-bodies diluted in binding buffer were allowed to bind to integrin at 4° C. overnight. Unbound material was washed with buffer A containing 0.05% Tween-20 (wash buffer). Bound material was detected using biotinylated anti-transferrin and streptavidin-HRP in binding buffer, washing with wash buffer following each step. Quantitation of binding was done on a SpectraMax Gemini EM and SoftMax software using QuantaBlue fluorescent substrate. See FIG. 14

Figure 15:
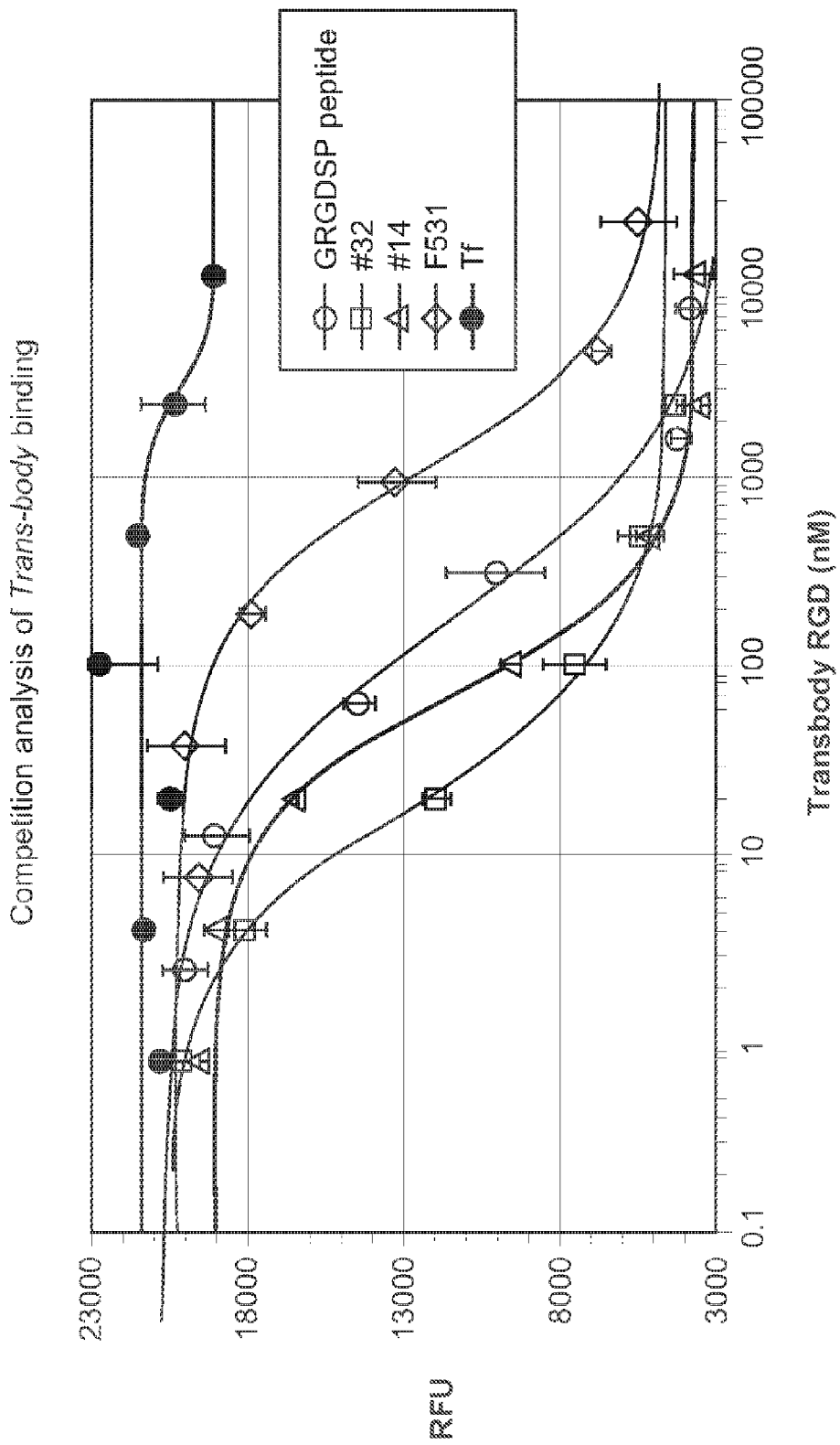
FIG. 15 shows competitive binding analysis of RGD transbody binding in RFU.

Trans-body binding was also assessed in a competition ELISA assay format. Integrin was coated and plates were blocked as above. Trans-body, or control peptide, and biotinylated fibronectin in binding buffer were added to appropriate wells and allowed to bind overnight at 4° C. Plates were washed with wash buffer and bound fibronectin was detected using streptavidin-HRP. Quantitation of binding was done as above. See FIG. 15.

Platelet aggregation analysis.

Figures 16A, 16B, 16C:
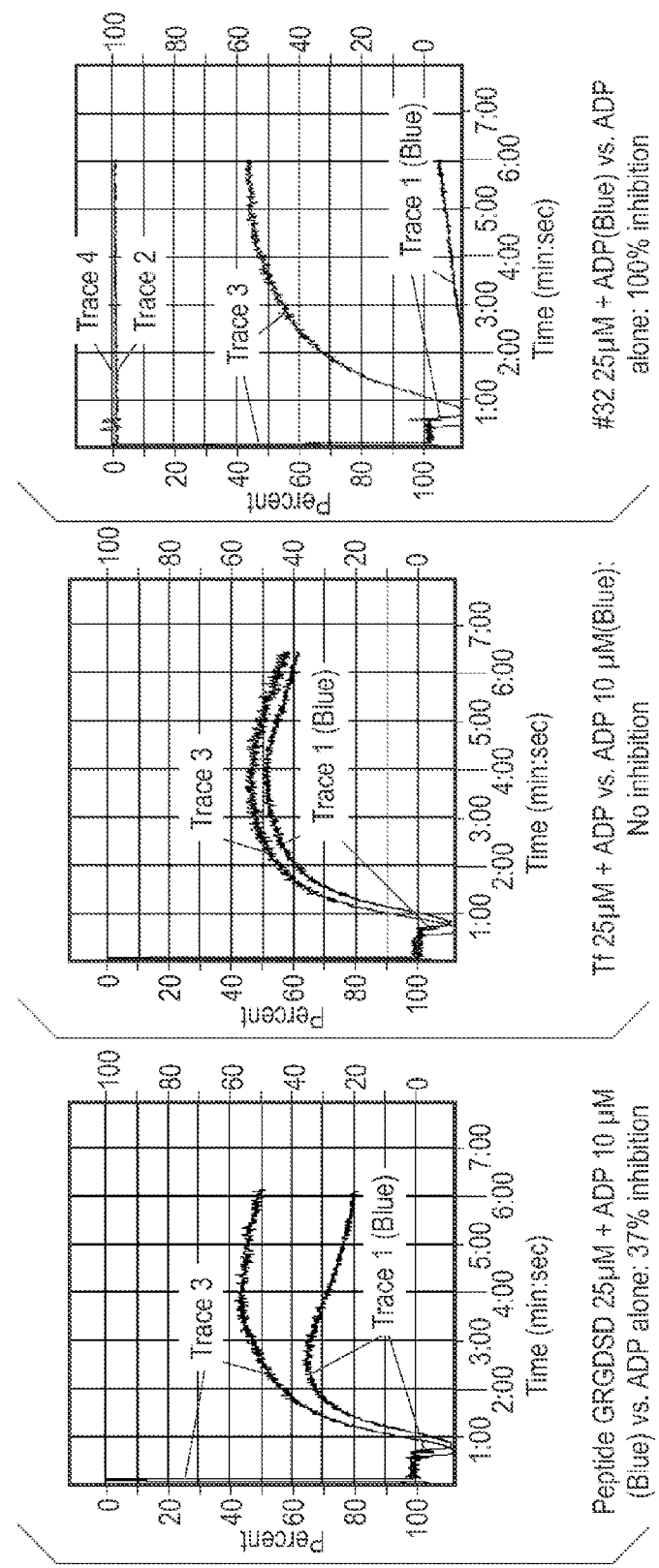
FIG. 16 shows inhibition of mouse platelet aggregation by an RGD trans-body clone. For FIGS. 16(A), 16(B) and 16(C), ADP control is denoted as Trace 3. Samples containing ADP plus peptides (RGD peptide in FIG. 16(A), Tf in FIG. 16(B), and peptide #32 in FIG. 16(C), are each denoted as Trace 1 (Blue) in the respective figures.

Platelet aggregation assays were performed with mouse platelet-rich plasma (PRP). Fresh platelets were obtained from B6 mice. The platelets were diluted to $2.5 \times 10^8$/mL for use. Platelet aggregation was measured with an aggregometer at 37° C. with stirring (900 rpm). Test sample was incubated with PRP for 10 min. prior to the addition of ADP (10 $\mu$M). The extent of platelet aggregation was continuously monitored for 6 min by turbidimetry and expressed as the increase in light transmission. See FIG. 16.

Example 7

MUC3 Stalk Engineering

For display of proteins on the surface of yeast, human MUC3 (hMUC3) protein was optimized as a display stalk. The hMUC3 DNA sequence (Genebank accession #AAC02272) was modified to remove some of the repetitiveness and allow construction by synthetic oligonucleotides codon optimized for yeast. The resulting hMUC3 stalk sequence (see sequence below) was synthesized by GenScript Corporation Piscataway, N.J.

The modified hMUC3 DNA proved to be unstable in *E. coli* when in a yeast display vector. The hMUC3 DNA sequence was further engineered through random mutagenesis and selection of clones that were stable in *E. coli*. The hMUC3 DNA sequence was subjected to 2 rounds of random mutagenesis by error prone PCR, GeneMorph II kit (Stratagene). The resulting PCR fragments were digested with SpeI/HindIII and ligated into SpeI/HindIII digested pREX0855. The ligation mixture was used to transform *E. coli* XL1-Blue. The cells were plated out, grown overnight and all the biomass recovered from the plate. Plasmid DNA was recovered, digested with NotI/XmnI and separated by agarose gel electrophoresis. The correct sized DNA band was cut from gel and purified. The resulting DNA containing the NotI display cassette with hMUC3 stalk was cloned into a pSAC35 based yeast display vector, pREX1003, by gap-repair in yeast.

All resulting yeasts were cultured in BMM/S medium and subjected to panning selection on plates coated with anti-FLAG antibody. An anti-Flag antibody (Sigma F9291) was diluted (1:25 dilution) in coating buffer (50 mM Borate buffer, pH 9.5) and coated onto a Petridish overnight at 4° C. After rinsing three times with binding buffer (PBS-T, 2 mM EDTA, 1% BSA), the plate was blocked for 2 hours at RT with binding buffer. 40 $OD_{600}$ units of overnight yeast culture was collected and suspended in 10 mL binding buffer and incubated with coated antibody for 2 hours at RT with gentle shaking. Unbound cells were washed away with 3 washes using binding buffer and bound cells were collected.

Figure 17:
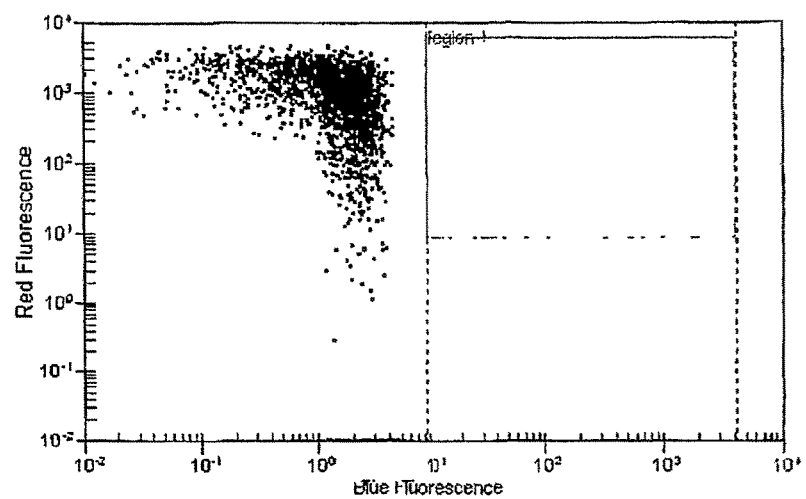
FIG. 17 is a FACS analysis of hMUC3 variants expressed in yeast.

The binders showed a high level of protein display as demonstrated by FACS analysis (FIG. 17). Individual clones were isolated to obtain a hMUC3 DNA sequence that was stable in *E. coli* and gave high level display in yeast.

```
Modified human MUC3 gene
                          (SEQ ID NO.: 76)
TCTACTAGTACACCAAGCTATACTACATCAATTACTAGCACTGA

GACACCATCTCATTCAACTCCTTCTAGTTCGACTTCAATTACAA

CTACAGAGACACCCAGTCACAGCACCCCATCTTACACTAGCTCT

GTCTCCACATCCGAGACTACATCACATTCTACTCCATCAGAAAC

AAGCTCCAGTAGAACAACAGAAAGCACCTCTTATAGTTCACCTA

GCTCCACTTCATCTAACACAATTACTGAGACAAGCTCACACTCC

ACTCCTAGTACTGCTACTTCTATTTCCTCGACCGAAACACCTAG

TTCAAGTACACCATCTGTATCATCGTCCATTACTGTTACTGAGA

GTTCATCTCATAGCACTCCTGGAGCTACTTCCACTTTGACATCG

AGTGAAACTTCTACTTGGTCAACACCATCTAGCACAAGTTCTAT

TATGTCAAGCTCCTACACTTCAGCTGACACTCCATCTGAAACAT

CAGTTTATACTTCCAGCGAAACCCCATCGTCCTCAAGCCCAACT

AGCACATCTTTGATTTCTAGTTCGAAGTCAACATCGACCAGTAC

ACCTTCGTTTACTTCTTCGATTACTAGCACTGAGACCTCCTCAT

ATTCTGCTAGTTCCTATACACCTTCAGTTAGTAGCACAGCAAGT

TCTAGCAAGAACACAACGAGTTCCACTGCTTCTATAAGCAGTAC

AGAGACTGTTAGTTCATCGACTAGCTCTGTCTCTAGTACTATTC

CTTCTTCTCAATCCACAAGTTATTCTACACCATCATTCTCCAGT

TCGGCAACAAGCAGTGTTACTCCATTGCATTCAACACCATCTCT

ACCATCTTGGGTTACTACAAGTAAGACCACATCACATATTACAC

CAGGTCTGACTTCGTCCATGTCTTCGAGCGAGACCTATAGCCAT

AGTACTCCAGGTTTTACAAGCTCTATTACTTCGACAGAATCGAC

AAGTGAGTCAACTCCATCATTGTCCAGTTCTACAATTTATAGTA

CTGTTTCAACATCTACTACAGCTATTACTTCACATTTTACAACT

TCTGAGACAGCTGTTACTCCAACACCAGTTACACCCTCTAGCTT

GAGTACAGATATCCCAACTACAAGTTTGAGAACTTTGACTCCTT

CCTCTGTTGGTACCTCGACTTCCTTGACAACTACAACTGACTTT

CCATCAATTCCAACAGACATTAGCACTTTGCCAACAAGAACTCA

TATTATTTCAAGCTCACCATCTATTCAATCAACAGAGACTAGCA

GTTTGGTTGGTACTACATCTCCAACTATGTCAACAGTTAGAATG

ACTTTGAGAATTACAGAGAACACTCCAATTTCTTCATTCAGTAC

TTCCATTGTTGTTATTCCAGAGACACCAACTCAAACACCACCAG

TTTTGACTTCTGCTACAGGTACTCAAACATCACCAGCTCCAACT

ACAGTTACTTTTGGTTCTACTGACTCATCTACATCAACTTTGCA

TAAGCTTTTG
```

Example 8

Randomization of Surface Exposed Transferrin Amino Acid Residues

Transferrin fusion protein libraries can be created by randomization of surface exposed amino acid residues, e.g., 6 surface exposed residues, i.e., not inserts, at several points within the Tf molecule. These residues do not need to be sequential but would be preferably grouped in a region with the side chains projecting away from the body of the molecule into the solvent phase. A library with 6 surface exposed residues would only require ~$10^7$ proteins, and as such would only require 20 to 40 transformations per library (depending on the quality of the primer).

Examples of three possible sites are:

| Site I | | Site II | | Site III | |
|--------|--------|---------|--------|----------|--------|
| Y85    |        | K276    |        | H207     |        |
| G86    |        | D277    |        | S208     |        |
| S87    |        | K280    |        | F211     |        |
| E89    |        | Q283    |        | E212     |        |
| D90    |        | S286    |        | A215     |        |
| Q92    |        | D297    |        | N216(Optional) | |
|        |        | (Optional S298) |  | K217(Optional) | |

Example 9

Expression of Transferrin Fusion Protein on Surface of Mammalian Cell

Materials & Methods

HEK-293 cells were grown and maintained in DMEM (HyClone) supplemented with 10% fetal bovine serum (HyClone), L-glutamine (GIBCO-BRL), & HEPES (GIBCO-BRL).

The human placental alkaline phosphatase (ALPP) GPI DNA sequence was generated by annealing primers P0926 and P0927 and then extending with Taq DNA polymerase.

```
P0926
ACTAAGCTTGACCTGGCTCCACAAATTGCTGGCTATACCGACGCCGC
GCATCCGGGTAGATCCGTGGTCCCAGCTTTGCTTCCTCT
(SEQ ID NO: 94)

P0927
TTATCTAGATTATTATGGAGCAGTGGCAGTTTCCAACAGTAACAGAG
TACCGGCCAGCAGAGGAAGCAAAGCTGGGAC (SEQ ID NO: 95)
```

Figure 18:
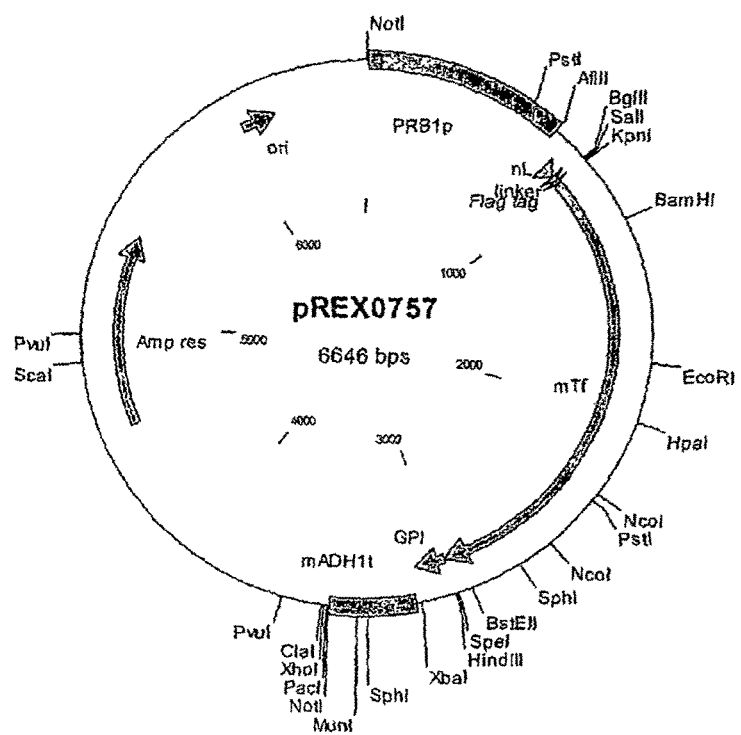
FIG. 18 provides the vector map for pREX0757.
Figure 19:
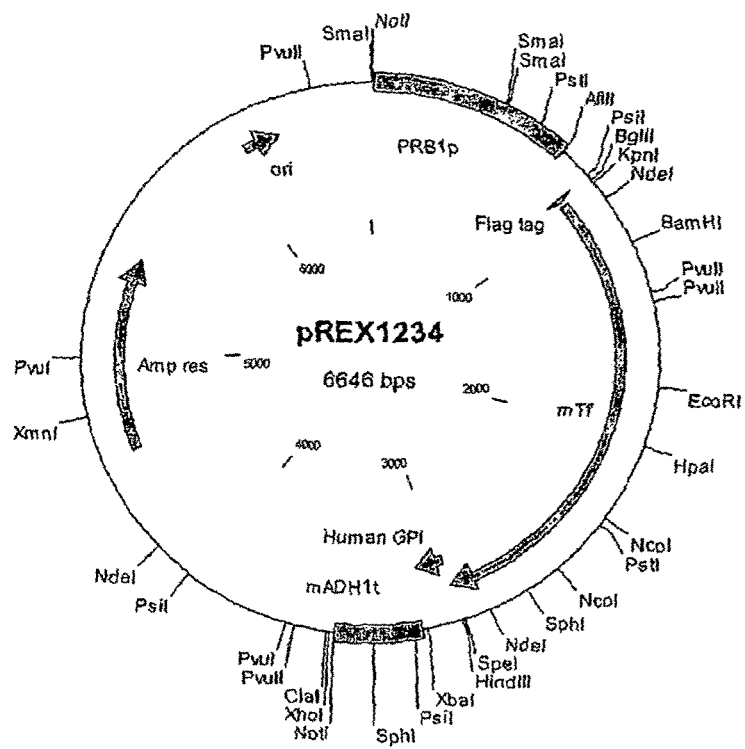
FIG. 19 provides the vector map for pREX1234.

The PCR reaction conditions were 94° C. for 1 min., 25 cycles 94° C. for 40 sec, 55° C. for 40 sec and 72° C. for 2 min. followed by a 7 min extension at 72° C. The PCR product was digested with HindIII/XbaI, cloned into the HindIII/XbaI sites of pREX0757 (FIG. 18), which removed a yeast GPI sequence, and then sequenced. The resulting plasmid, pREX1234, (FIG. 19) contained modified transferrin (mTf) with a FLAG Tag at the N-terminus and the human GPI sequence at the C-terminus. This mTf cassette was modified at the 5' and 3' ends for cloning into the mammalian expression vector by PCR with primers P2225 and P2226 under the following conditions: 94° C. for 1 min., 25 cycles 94° C. for 40 sec, 55° C. for 40 sec and 72° C. for 2 min followed by a 7 min extension at 72° C.

```
P2225
CACCATGAGGCTCGCCGTGGGAGCCCTG
(SEQ ID NO: 96)
```

-continued

P2226
TTATTATGGAGCAGTGGCAGTTTC
(SEQ ID NO: 97)

Figure 20:
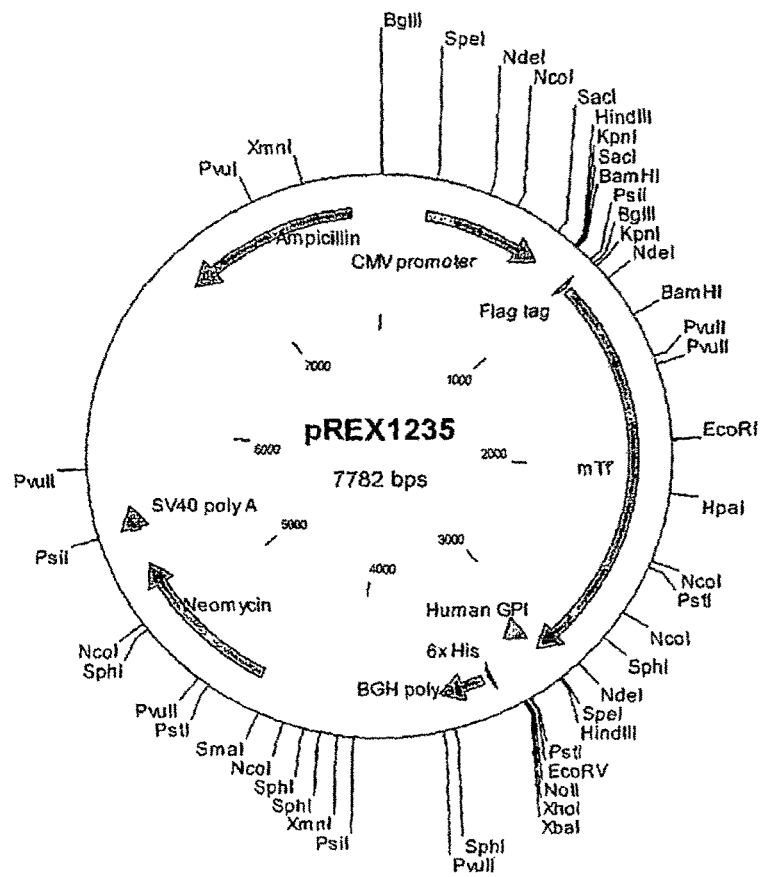
FIG. 20 provides the vector map for pREX1235.

This PCR product was cloned into pcDNA3.1 (Invitrogen, Carlsbad, Calif.) to generate pREX1235 (FIG. 20). The sequence of the mTf cassette in pREX1235 was confirmed by DNA sequencing.

HEK-293 cells were transfected with pREX 1235 using FuGENE 6 (Roche) according to the manufacturer's protocol. Cells were washed in 1× phosphate-buffered saline (1×PBS) and lysed overnight at 4° C. with cell lysis buffer (20 mM Tris-HCl at pH 7.4, 150 mM NaCl, 1% Triton X-100, 1 mM EDTA) and a mixture of the Halt™ phosphatase inhibitor cocktail (Pierce) and a protease inhibitor cocktail (Sigma). Cells were pelleted for 30 min at 14,000 rpm at 4° C. Supernatant was collected and allowed to bind anti-Flag agarose beads (Sigma) for 2 h at 4° C. Pellets were washed once in lysis buffer, two times in Tris-buffered saline (TBS) (20 mM Tris-HCl at pH 7.4, 150 mM NaCl)+0.5% Triton X-100, and once in 1×PBS. Samples were eluted in NuPAGE® LDS sample loading buffer+sample reducing agent (Invitrogen). The recovered protein was run on a NuPAGE™ 4-12% Bis-Tris gel (Invitrogen) and transferred to a PVDF (Invitrogen) membrane with NuPAGE® Transfer buffer as per manufacturer's instructions. Blots were blocked in 5% nonfat dry milk in PBS-T (1×PBS+0.2% Tween-20) for 1 h at room temperature and probed with biotinylated primary antibodies against either FLAG (1:1000 mouse anti-FLAG BioM2; Sigma) or human transferrin (1:4000 biotinylated chicken anti-human transferrin; Accurate Chemical & Scientific) for 2 h at room temperature (RT) followed by incubation with strepavidin-horse-radish peroxidase (SA-HRP) (1:2500 ImmunoPure®Strepavidin Horseradish, Peroxidase Conjugated; Pierce) for 1 h at RT. Alternatively, for surface biotinylation experiments, blots were probed with only SA-HRP (1:2500; Pierce). All blots were developed using the SuperSignal West Dura Extended Duration Substrate (Pierce) and visualized on the Fluor-S™ MultiImager (Bio-Rad) using the Quantity One Software (v.4.5.0; Bio-Rad).

HEK-293 cells were transfected for 24 h as described above. Cells were washed three times in sterile, ice-cold 1×PBS. Cells were then treated with 0.5 mg/mL of Sulfo-NHS-LC-Biotin reagent (Pierce) in 1×PBS and incubated on a rocker platform for 2 hr at 4° C. Following surface biotinylation, cells were washed three times with quench buffer (1×PBS+100 mM glycine) and resuspended in cell lysis buffer for immunoprecipitation and immunoblotting as described above.

HEK-293 cells were transfected for 24 h as described above. The cells were washed once in sterile 1×PBS, then resuspended in additional 1×PBS and counted. $4.25 \times 10^5$ cells per sample were transferred to 1.5 mL eppendorf tubes. Cells were pelleted at 4000 rpm for 3 min at 4° C. Cells were then blocked in 1×PBS-T (0.05% Tween-20) for 30 min at RT, spun down, resuspended in primary antibody (1:25-1:625 mouse anti-FLAG BioM2; Sigma), and allowed to incubate for 30 min at RT. Cells were washed twice in 1×PBS-T, resuspended in secondary antibody (1:100 goat anti-mouse-APC; Molecular Probes), and allowed to incubate for 30 min at RT. Following two additional washes in 1×PBS-T, cells were resuspended in Cell Buffer (Agilent) to bring cells to a final concentration of $2 \times 10^6$ cells/mL and loaded onto a cell fluorescence chip (Cell Fluorescence LabChip® Kit, Agilent) as per manufacturer's instructions. All FACS analyses were performed using the Agilent 2100 bioanalyzer and 2100 software.

Results.

Figure 21:
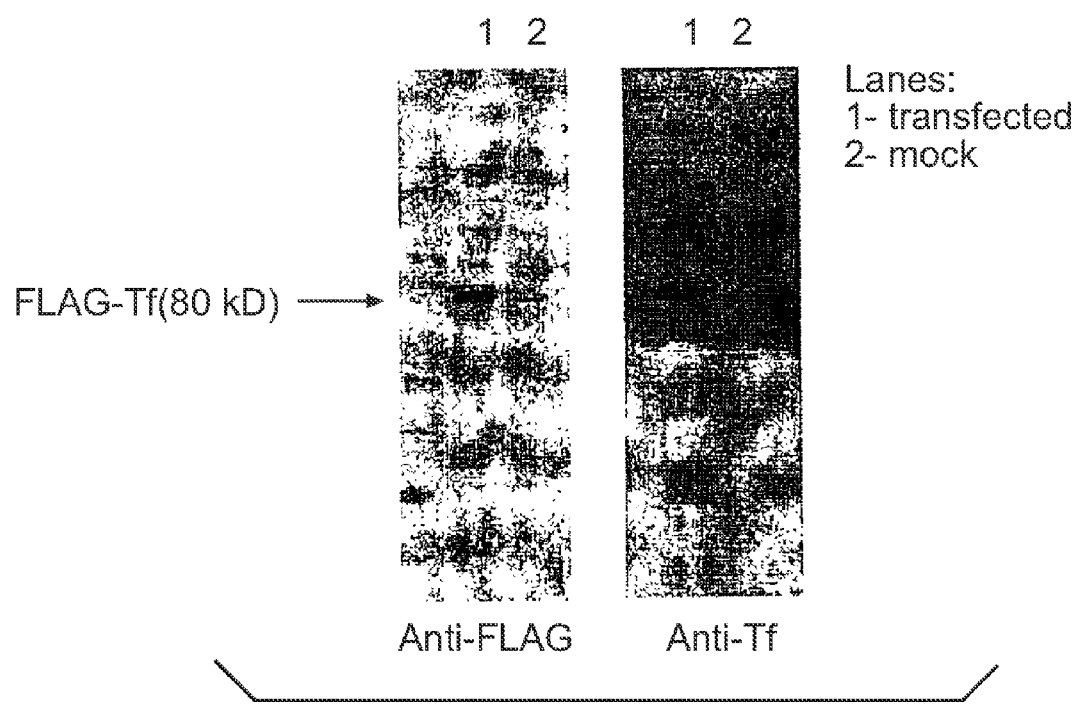
FIG. 21 is a western blot prepared using lysates from mammalian cells expressing Flag-tagged transferrin and probed with anti-Flag or anti-transferrin antibodies.
Figure 22:
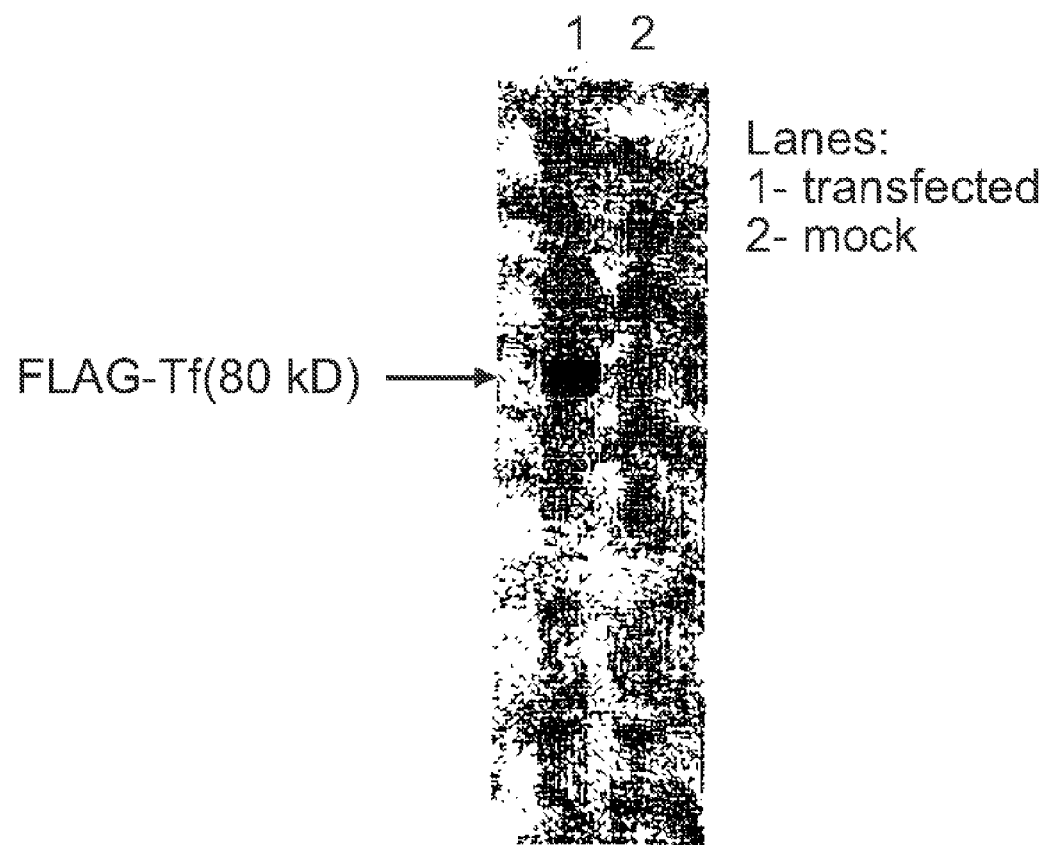
FIG. 22 is a western blot of exposed plasma membrane proteins.

Lysates from cells transfected with either pREX1235 or mock-transfected cells were subjected to immunoprecipitation with anti-FLAG-agarose beads and subsequent western blotting. Probing of western blots with either anti-FLAG or anti-transferrin antibodies clearly demonstrates the presence of both transferrin and FLAG moieties (FIG. 21).

pREX1235 or mock-transfected cells were surface-biotinylated prior to lysis and subjected to immunoprecipitation with anti-FLAG-agarose and western blotting using strepavidin-HRP. Surface-biotinylation ensures that only exposed plasma membrane proteins will be detected in western blotting. A FLAG-precipitable protein of the predicted molecular weight was observed, demonstrating that the FLAG-transferrin fusion is expressed on the cell surface (FIG. 22).

Figure 23:
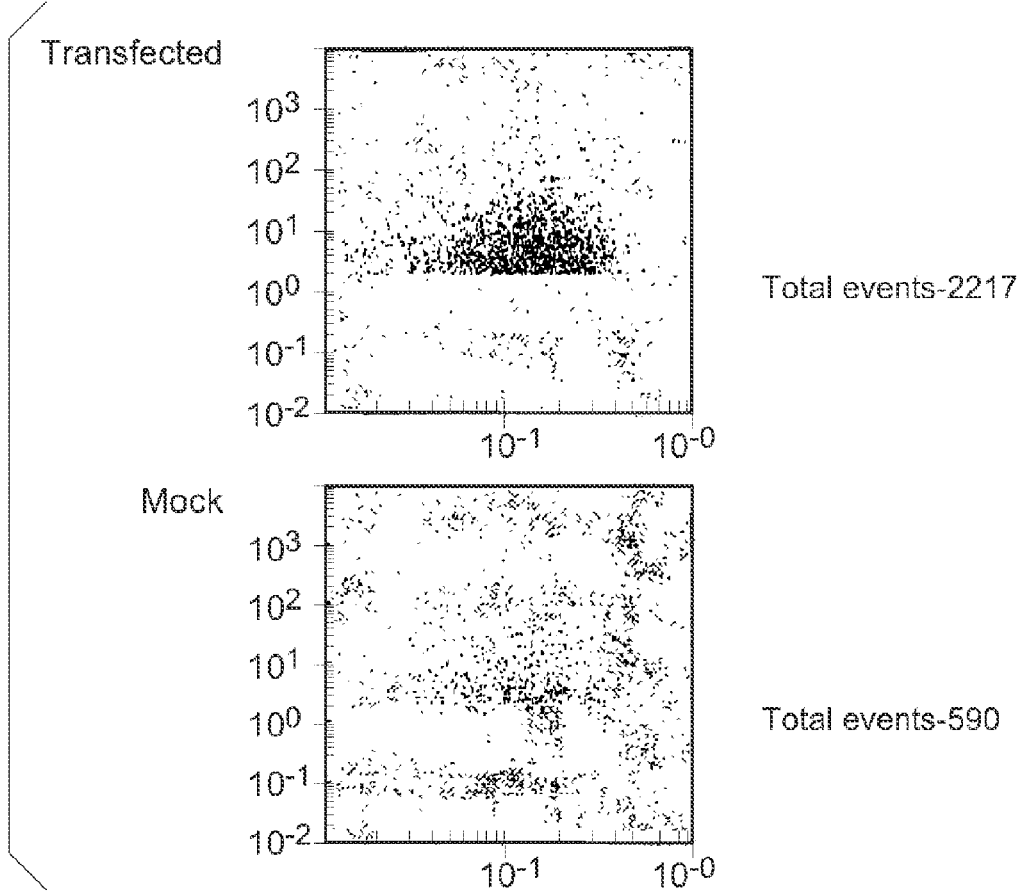
FIG. 23 is a FACS analysis of pREX1235.

Additionally, transfected cells were subjected to fluorescence-activated cell sorting (FACS) analysis. A 4-fold increase in staining was observed in pREX1235-transfected cells relative to mock-transfected cells, clearly demonstrating cell-surface expression of the FLAG-transferrin fusion (FIG. 23).

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

We claim:

1. A fusion protein comprising a stalk moiety comprising a mucin 3 (MUC3) variant encoded by a nucleic acid comprising at least 95% identity to the sequence of SEQ ID NO: 76.

2. The fusion protein of claim 1, wherein the fusion protein further comprises a glycosyl-phosphatidyl-inositol (GPI).

3. The fusion protein of claim 1 wherein the stalk moiety is encoded by nucleic acid comprising at least 98% identity to SEQ ID NO: 76.

4. The fusion protein of claim 1, wherein the MUC3 variant is encoded by a nucleic acid comprising the sequence of SEQ ID NO: 76.

\* \* \* \* \*